(12) United States Patent
Adje et al.

(10) Patent No.: US 7,482,484 B2
(45) Date of Patent: Jan. 27, 2009

(54) CARBOXYLIC ACIDS AND DERIVATIVES FOR THE TREATMENT OF AND PREVENTING DIABETES AND DYSLIPIDAEMIA

(75) Inventors: Nathalie Adje, Genas (FR); Michel Brunet, Toussieu (FR); Didier Roche, Lyons (FR); Jean-Jacques Zeiller, Lyons (FR); Stéphane Yvon, Ste Foy les Lyons (FR); Valérie Guyard-Dangremont, Saint Maurice de Gourdans (FR); Francis Contard, Lyons (FR); Daniel Guerrier, Saint Genis Laval (FR); Gérard Ferrand, Lyons (FR); Yves Bonhomme, Charbonnières les Bains (FR)

(73) Assignee: Merck Patent GmbH, Darmstadt (DE)

( * ) Notice: Subject to any disclaimer, the term of this patent is extended or adjusted under 35 U.S.C. 154(b) by 276 days.

(21) Appl. No.: 10/542,028

(22) PCT Filed: Dec. 16, 2003

(86) PCT No.: PCT/EP03/14296

§ 371 (c)(1),
(2), (4) Date: Jul. 12, 2005

(87) PCT Pub. No.: WO2004/063148

PCT Pub. Date: Jul. 29, 2004

(65) Prior Publication Data

US 2006/0111445 A1    May 25, 2006

(30) Foreign Application Priority Data

Jan. 13, 2003 (FR) .................... 03 00318

(51) Int. Cl.
*C07C 62/00* (2006.01)
*C07C 229/40* (2006.01)
*C07C 251/20* (2006.01)

(52) U.S. Cl. .............. 562/466; 562/430; 562/440; 562/429; 562/433; 562/427; 560/9; 560/11; 560/19; 560/55

(58) Field of Classification Search ............... 562/427, 562/429, 430, 433, 440, 466; 560/9, 11, 560/12, 19, 55, 59
See application file for complete search history.

(56) References Cited

U.S. PATENT DOCUMENTS

| 5,128,362 | A | 7/1992 | DeBernardis et al. |
|---|---|---|---|
| 5,750,524 | A | 5/1998 | Mera et al. |
| 5,780,465 | A | 7/1998 | Cressman et al. |
| 5,922,771 | A | 7/1999 | Fukatsu et al. |
| 6,713,515 | B2 * | 3/2004 | Iotzova et al. ............... 514/569 |
| 2003/0055265 | A1 | 3/2003 | Binggeli et al. |

FOREIGN PATENT DOCUMENTS

| EP | 0773019 | 5/1997 |
|---|---|---|
| JP | 53012421 | 2/1978 |
| WO | WO 02092084 | 11/2002 |

OTHER PUBLICATIONS

Brown et al. J. Med. Chem. 1989, 32, 807-826.*
Database CA 'Online! Chemical Abstracts Service, Columbus, Ohio, US: Litvinova, L.A. et al.: "Synthesis and Antiviral Activity of 2, 7-BIS(Alkoxycarbonylmethoxy)-9-Fluorenones" Retrieved From STN, vol. 23, No. 6, 1989, pp. 702-704.
Database Crossfire Beilstein 'Online! Beilstein Institut Zur Foerderung Der Chemischen Wissenchaten, Frankfurt Am Main, De.
Database Crossfire Beilstein 'Online! Beilstein Institut Zur Foerrderung Der Chemischen Wissenchaften, Franfurt Am Main, De.
Database CA 'Online! Chemical Abstracts Service, Columbus, Ohio, US; Merchant, Jaysukhal R. et al. "Synthesis of Some Indan-1-Ones".
Journal of the Chemical Society, Perkin Transactions 1: Organic and Bio-Organic Chemistry (1972-1999).
Database CA 'Online! Chemical Abstracts Service, Columbus, Ohio, US: Hiroya, Kou et al: "An Alternative Route to a Benzofuran Natural Product Dehydrotremetone".

* cited by examiner

*Primary Examiner*—Yvonne Eyler
*Assistant Examiner*—Yevegeny Valenrod
(74) *Attorney, Agent, or Firm*—Millen, White, Zelano, Branigan, P.C.

(57) ABSTRACT

Disclosed are Compounds of formula I

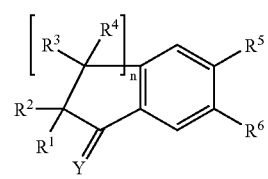

And methods of use thereof for the treatment of dyslipidaemia, atherosclerosis and diabetes.

29 Claims, No Drawings

CARBOXYLIC ACIDS AND DERIVATIVES FOR THE TREATMENT OF AND PREVENTING DIABETES AND DYSLIPIDAEMIA

This application is a National Phase of PCT/EP2003/014296 filed Dec. 16, 2003.

The present invention relates to carboxylic acid derivatives that can be used in the treatment of dyslipidaemia, atherosclerosis and diabetes, to pharmaceutical compositions comprising them and to processes for the preparation of these compounds.

The invention also relates to the use of these compounds for the production of medicaments for the treatment of dyslipidaemia, atherosclerosis and diabetes.

In most countries, cardiovascular disease remains one of the major diseases and the main cause of death. About one third of men develop a major cardiovascular disease before the age of 60, with women showing a lower risk (ratio of 1 to 10). With advancing years (after the age of 65, women become just as vulnerable to cardiovascular diseases as men), this disease increases even more in scale. Vascular diseases, such as coronary disease, strokes, restenosis and peripheral vascular disease remain the prime cause of death and handicap worldwide.

Whereas the diet and lifestyle can accelerate the development of cardiovascular diseases, a genetic predisposition leading to dyslipidaemia is a significant factor in cardiovascular accidents and death.

The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis was mainly focused on the metabolism of cholesterol and on the metabolism of triglycerides.

However, since the studies of Randle et al. (Lancet, 1963, 785-789), a novel concept has been proposed: a glucose-fatty acid cycle or Randle cycle, which describes the regulation of the equilibrium between the metabolism of lipids in terms of triglycerides and cholesterol, and the oxygenation of glucose. Following this concept, the inventors have developed a novel programme, the aim of which is to find novel compounds acting simultaneously on lipid metabolism and glucose metabolism.

Fibrates are well-known therapeutic agents with a mechanism of action via the "Peroxisome Proliferator Activated Receptors". These receptors are the main regulators of lipid metabolism in the liver (PPARα isoform). In the last 10 years, thiazolidinediones have been described as powerful hypoglycaemiant agents in man and animals. It has been reported that thiazolidinediones are powerful selective activators of another isoform of PPARs: PPARγ (Lehmann et al., J. Biol. Chem., 1995, 270, 12953-12956).

The inventors have discovered a novel class of compounds that are powerful activators of the PPARα and PPARγ isoforms. As a result of this activity, these compounds have a substantial hypolipidaemiant and hypoglycaemiant effect.

The compounds of the invention have the formula I:

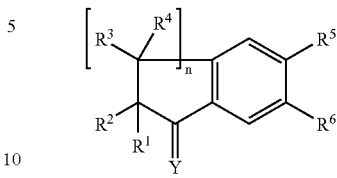

in which:

n is an integer chosen from 1, 2 and 3;

Y represents O; N—OR$^9$, in which R$^9$ represents H or a saturated hydrocarbon-based aliphatic group; CR$^{10}$R$^{11}$, in which R$^{10}$ and R$^{11}$, which may be identical or different, represent H or a saturated hydrocarbon-based aliphatic group;

R$^1$ and R$^2$, which may be identical or different, represent H or a saturated aliphatic hydrocarbon-based chain; or alternatively R$^1$ and R$^2$ together form an optionally substituted saturated aliphatic hydrocarbon-based chain; the radicals R$^3$ and R$^4$, which may be identical or different, take any of the meanings given above for R$^1$ and R$^2$, or alternatively R$^1$ and the group R$^4$ borne by the carbon alpha to CR$^1$R$^2$ represent nothing and a double bond links the CR$^1$R$^2$ carbon to the alpha CR$^3$R$^4$ carbon; or alternatively one of the radicals R$^1$ and R$^2$ forms with one of the radicals R$^3$ and R$^4$ an optionally substituted saturated or unsaturated aliphatic hydrocarbon-based chain, such as alkylene or alkenylene;

one of the radicals R$^5$ and R$^6$ represents W, and the other represents Z which is chosen from an optionally substituted saturated or unsaturated aliphatic hydrocarbon-based radical; an optionally substituted, saturated, unsaturated and/or aromatic carbocyclic or heterocyclic radical; a radical -alk-Cy, in which alk represents an alkylene chain and Cy represents an optionally substituted saturated, unsaturated and/or aromatic heterocyclic or carbocyclic radical;

W represents —XL-CO$_2$R$^7$; —X-L-Tet, in which X and L are as defined below and Tet represents optionally substituted tetrazole;

R$^7$ represents H, a saturated or unsaturated aliphatic hydrocarbon-based group, an optionally substituted, saturated, unsaturated and/or aromatic carbocyclic group, or an optionally substituted, saturated, unsaturated and/or aromatic heterocyclic group;

X represents O; NR$^8$, in which R$^8$ represents H; a saturated aliphatic hydrocarbon-based group; a group —CO—R' or —SO$_2$—R', in which R' takes any of the meanings given above for R$^7$ with the exception of H; or an optionally substituted aromatic carbocyclic group;

S(O)$_m$, in which m is chosen from 0, 1 and 2;

L represents a saturated or unsaturated aliphatic hydrocarbon-based chain, which is optionally substituted and/or optionally interrupted by optionally substituted arylene; and the pharmaceutically acceptable derivatives, salts, solvates and stereoisomers thereof, and also mixtures thereof in all proportions.

Among the derivatives of the compounds of the formula I that are intended in particular are the salts.

Examples of salts include the pharmaceutically acceptable salts formed with a pharmaceutically acceptable organic or mineral base or with a pharmaceutically acceptable organic or mineral acid.

Examples of salts with organic or mineral bases that may be mentioned include the salts form with metals and especially alkali metals, alkaline-earth metals and transition metals (such as sodium, potassium, calcium, magnesium or aluminium), or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

Examples of salts with organic or mineral acids include the hydrochloride, hydrobromide, sulfate, hydrogen sulfate, dihydrogenphosphate, citrate, maleate, fumarate, 2-naphthalenesulfonate and para-toluenesulfonate.

The invention also covers the salts allowing a suitable separation or crystallisation of the compounds of the formula I, such as picric acid, oxalic acid or an optically active acid, for example tartaric acid, dibenzoyltartaric acid, mandelic acid or camphorsulfonic acid. However, a preferred subgroup of salts consists of salts of the compounds of the formula I with pharmaceutically acceptable acids or bases.

The formula I also includes all the types of geometrical isomers and stereoisomers of the compounds of the formula I.

Thus, the invention is also directed towards the optically active forms (stereoisomers), enantiomers, racemic mixtures, diastereoisomers, hydrates and solvates of these compounds. The term "solvate" is thus defined as covering the adducts of the compounds with inert solvent molecules, formed as a result of their mutual forces of attraction. Such solvates may be, for example, monohydrates, dihydrates, or alcoholates.

The term "pharmaceutically acceptable derivative" includes, for example, the salts of the compounds of the invention and the compounds also referred to as "prodrugs". The term "prodrug derivative" is defined as being the compounds of the formula I modified with, for example, alkyl or acyl, sugar or oligopeptide groups, which are rapidly cleaved in the body to form the active compounds according to the invention. They also include the biodegradable polymer derivatives of the compounds according to the invention.

The invention also relates to mixtures of the compounds of the formula I according to the invention, for example mixtures of two diastereoisomers in ratios, such as 1:1, 1:2, 1:3, 1:4, 1:5, 1:10, 1:100 or 1:1000. They are preferably mixtures of stereoisomeric compounds.

The term "aliphatic hydrocarbon-based group" means a hydrocarbon-based group having a linear or branched chain, preferably containing from 1 to 14 carbon atoms, preferentially from 1 to 10 and better still from 1 to 6 carbon atoms, for example from 1 to 4 carbon atoms.

Examples of saturated hydrocarbon-based aliphatic groups are alkyl radicals, such as methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

If the hydrocarbon-based aliphatic group is unsaturated, it may comprise one or two unsaturations. The unsaturations are either of ethylenic type or of acetylenic type. The unsaturated chains contain at least two carbon atoms.

Alkenyl and alkynyl groups are examples of unsaturated aliphatic hydrocarbon-based groups.

Examples of unsaturated aliphatic hydrocarbon-based groups of alkenyl type include allyl, vinyl and —CH=CH—CH$_3$.

Examples of alkynyl groups include —(CH$_2$)$_n$—C≡C—R, n being an integer between 0 and 10 and R representing —(CH$_2$)$_m$—CH$_3$, in which m is an integer between 0 and 10, or alternatively R represents H.

The expression "saturated or unsaturated aliphatic hydrocarbon-based chain" means a divalent radical derived from a saturated, or unsaturated, aliphatic hydrocarbon-based group as defined above by replacement of a hydrogen atom with a bond.

The saturated aliphatic hydrocarbon-based chains are termed "alkylene" if they contain no double bonds.

The unsaturated aliphatic hydrocarbon-based chains are termed "alkenylene" if they contain one or more unsaturations of ethylenic type.

In the context of the invention, the expression "saturated, unsaturated and/or aromatic cyclic (carbocyclic or heterocyclic) radical" means that the same radical may comprise a saturated portion and/or an unsaturated portion and/or an aromatic portion.

The carbocyclic and heterocyclic radicals include mono- and polycyclic radicals; these radicals preferably denote mono-, bi- or tricyclic radicals. In the case of polycyclic radicals, it should be understood that these radicals consist of monocycles fused in pairs (for example ortho-fused or peri-fused), i.e. containing at least two carbon atoms in common. Each monocycle is preferably 3-to 8-membered and better still 5-to 7-membered.

The heterocyclic groups comprise hetero atoms generally chosen from O, N and S optionally in oxidised form (in the case of S and N).

Each of the monocycles constituting the heterocycle preferably comprises from 1 to 4 hetero atoms and better still from 1 to 3 hetero atoms.

Examples of aromatic monocyclic heterocyclic groups include 5-to 7-membered monocyclic heteroaryls, such as pyridine, furan, thiophene, pyrrole, imidazole, thiazole, isoxazole, isothiazole, furazane, pyridazine, pyrazine, thiazines, oxazole, pyrazole, oxadiazole, triazole and thiadiazole.

Examples of unsaturated monocyclic heterocyclic groups include unsaturated derivatives of the aromatic and saturated monocyclic heterocycles mentioned above.

Examples of unsaturated 7-membered heterocycles include trithiatriazepines and trithiadiazepines. Examples of saturated 5-to 7-membered monocyclic heterocycles especially include tetrahydrofuran, dioxolane, imidazolidine, pyrazolidine, piperidine, dioxane, morpholine, dithiane, thiomorpholine, piperazine, trithiane, oxepine and azepine.

Examples of aromatic bicyclic heterocyclic groups in which each monocycle is 5-to 7-membered include indolizine, indole, isoindole, benzofuran, benzopyran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazine (such as pyrazolo-1,3,4-triazine), pyrazolopyrimidine and pteridine.

The saturated and unsaturated derivatives of these groups are examples of saturated and, respectively, unsaturated bicyclic heterocyclic groups.

Examples of aromatic tricyclic heterocyclic groups include those consisting of 5-to 7-membered monocycles, such as acridine or le carbazole. The saturated and unsaturated derivatives of these groups are examples of saturated and, respectively, unsaturated tricyclic heterocyclic groups.

The aromatic carbocyclic radicals are preferably $C_6$-$C_{18}$.

Among these radicals that may especially be mentioned are phenyl, naphthyl, anthryl and phenanthryl radicals.

The arylene radicals are divalent radicals derived from the corresponding $C_6$-$C_{18}$ aryl groups by replacement of a hydrogen atom with a bond. Phenylene is the preferred arylene group.

Saturated carbocyclic radicals are especially cycloalkyl radicals, preferably $C_3$-$C_{18}$ and better still $C_3$-$C_{10}$ cycloalkyl radicals, such as cyclopropyl, cyclobutyl, cyclopentyl, cyclohexyl, cycloheptyl, cyclooctyl, adamantyl or norbornyl.

The unsaturated carbocyclic groups comprise one or more, preferably 1 to 3, ethylenic double bonds and generally consist of from 6 to 18 and better still from 6 to 10 carbon atoms. Examples of these are cycloalkenyl radicals, and especially cyclohexenyl radicals.

Some of the compounds of the invention bear a double bond between the carbon $CR^1R^2$ and the carbon $CR^3R^4$ alpha to $CR^1R^2$. Thus, if n=1, the compounds in question have the formula:

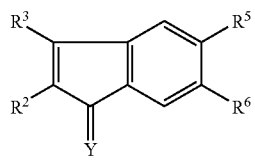

If n=2, the compounds in question have the formula:

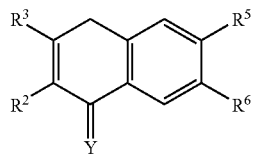

If either $R^1$ or $R^2$ forms with either $R^3$ or $R^4$ a saturated hydrocarbon-based chain, it is preferred for the groups $R^1$ (or $R^2$) and $R^3$ (or $R^4$) to be on two adjacent carbons. The resulting compound has, for example, the formula:

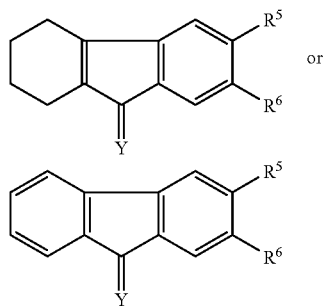

If L is an optionally substituted saturated or unsaturated aliphatic hydrocarbon-based chain, interrupted by optionally substituted arylene, L may represent:

- ◆ -aa-AA-
- ◆ -AA-aa-
- ◆ -aa$_1$-AA-aa$_2$-; or
- ◆ -AA$_1$-aa-AA$_2$- in which aa, aa$_1$ and aa$_2$ independently represent an optionally substituted, saturated or unsaturated hydrocarbon-based chain; AA, AA$_1$ and AA$_2$ independently represent optionally substituted arylene.

Preferably, $R^1$, $R^2$, $R^3$ and $R^4$ represent H or alkyl, for example methyl.

Advantageously, n represents 1 or 2.

Preferred meanings of $R^7$ are H and alkyl, preferably ethyl or methyl.

Preferably, L represents alkylene, alkenylene or -alk°-Ar°-, in which alk° represents alkylene and Ar° represents phenylene, such as:

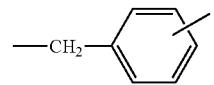

A preferred subgroup of compounds of the invention consists of the compounds for which L represents $C_1$-$C_4$ alkylene, such as propylene or methylene; aa$_3$-C(CH$_3$)$_2$—, in which -aa$_3$- represents nothing or alternatively represents a $C_1$-$C_4$ alkylene radical;

-aa$_4$-C(CH$_3$)(C$_2$H$_5$)—, in which -aa$_4$ is as defined for -aa$_3$-;

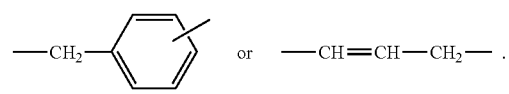

Advantageously, Z represents alkyl optionally substituted by one or more radicals T; alkenyl optionally substituted by one or more radicals T; alkynyl optionally substituted by one or more radicals T; phenyl optionally substituted by one or more radicals T; cycloalkyl optionally substituted by one or more radicals T; monocyclic or bicyclic heteroaryl optionally substituted by one or more radicals T; -alk$^1$-Cy$^1$-, in which alk$^1$ represents alkylene, preferably —CH$_2$— and Cy$^1$ represents phenyl optionally substituted by one or more radicals T, or alternatively Cy$^1$ represents cycloalkyl, optionally substituted by one or more radicals T; T representing cyano, optionally halogenated alkyl, such as perhaloalkyl, optionally halogenated alkoxy or a halogen atom.

A preferred subgroup of compounds consists of the compounds defined above for which Z represents alkyl optionally substituted by cyano; phenyl optionally substituted by optionally halogenated alkyl (such as trifluoromethyl) or with optionally halogenated alkoxy; phenylalkyl, in which phenyl is substituted by one or more halogen atoms, alkyl or alkoxy; optionally halogenated monocyclic or bicyclic heteroaryl (such as trifluoromethyl) or with optionally halogenated alkoxy; alkynyl; or cycloalkylalkyl.

In a more particularly preferred manner, Z represents $C_1$-$C_{12}$ alkyl; $C_2$-$C_{13}$ cyanoalkyl; phenyl substituted by one or more halogen(s), optionally halogenated alkyl, or alkoxy; heteroaryl substituted by one or more halogen(s), optionally halogenated alkyl, or alkoxy; benzyl or phenethyl optionally substituted by one or more halogen, alkyl or alkoxy; norbornyl; —(CH$_2$)$_m$—C≡C—P°, in which m is an integer between 0 and 3 and P° represents $C_1$-$C_6$ alkyl; cyclohexylmethyl.

Another subgroup of preferred compounds is the group consisting of the compounds of the formula I in which n=1; $R^1$, $R^2$, $R^3$ and $R^4$ represent a hydrogen atom; Y represents O; $R^5$ represents $(C_1-C_{10})$alkyl; $(C_2-C_{10})$alkynyl; -alk$^1$-Cy$^1$, in which alk$^1$ represents $(C_1-C_3)$alkylene and Cy$^1$ represents phenyl optionally substituted by one or more radicals T, in which T is as defined above; $R^6$ represents W, in which X represents O or NH; and L represents $(C_1-C_3)$alkylene.

Among these compounds, the following are especially preferred:
→those for which X represents NH; and $R^5$ represents $(C_1-C_{10})$alkyl;
→those for which X represents O; $R^5$ represents $(C_1-C_{10})$alkyl; $(C_2-C_{10})$alkynyl; or
-alk$^1$-Cy$^1$, in which alk$^1$ represents $(C_1-C_3)$alkylene and Cy$^1$ represents phenyl.

Table α below collates 12 preferred subgroups of the invention according to the values of n and of Y.

TABLE α

|   | n | | |
|---|---|---|---|
| Y | 1 | 2 | 3 |
| O | 1 | 2 | 3 |
| —N—OH | 4 | 5 | 6 |
| —N—O-alkyl | 7 | 8 | 9 |
| CR$^{10}$R$^{11}$ | 10 | 11 | 12 |

Table β below moreover defines the preferred subgroups 13 to 40 of the invention according to the values of X and of $R^7$ if, in formula I, W represents —X-L-CO$_2$R$^7$.

TABLE β

| | X | | | | | | |
|---|---|---|---|---|---|---|---|
| $R^7$ | O | NH | N-alkyl | NCR' | NSO$_2$R' | N-carbocyclic group | —S(O)$_m$ |
| H | 13 | 14 | 15 | 16 | 17 | 18 | 19 |
| hydrocarbon-based aliphatic | 20 | 21 | 22 | 23 | 24 | 25 | 26 |
| carbocyclic | 27 | 28 | 29 | 30 | 31 | 32 | 33 |
| heterocyclic | 34 | 35 | 36 | 37 | 38 | 39 | 40 |

Table γ collates the preferred subgroups 41 to 47 of compounds of the formula I for which W represents —X-L-Tet, according to the values of X.

TABLE γ

| | X | | | | | | |
|---|---|---|---|---|---|---|---|
| | O | NH | N-alkyl | NCOR' | NSO$_2$R' | N-carbocyclic group | —S(O)$_m$ |
| Preferred subgroup No | 41 | 42 | 43 | 44 | 45 | 46 | 47 |

Matrix δ below moreover defines preferred subgroups derived from the subgroups 1 to 47 defined above. More specifically, the elements of this matrix, which each represent preferred subgroups of the invention, are defined in the form of a couple, each member of the couple indicating the origin of the subgroup and thereby defining n, Y and W.

$$\delta \begin{pmatrix} (1,13) & (1,14) & \cdots & (1,i) & \cdots & (1,47) \\ (2,13) & (2,14) & \cdots & (2,i) & \cdots & (2,47) \\ (3,13) & (3,14) & \cdots & (3,i) & \cdots & (3,47) \\ (4,13) & (4,14) & \cdots & (4,i) & \cdots & (4,47) \\ (5,13) & (5,14) & \cdots & (5,i) & \cdots & (5,47) \\ (6,13) & (6,14) & \cdots & (6,i) & \cdots & (6,47) \\ (7,13) & (7,14) & \cdots & (7,i) & \cdots & (7,47) \\ (8,13) & (8,14) & \cdots & (8,i) & \cdots & (8,47) \\ (9,13) & (9,14) & \cdots & (9,i) & \cdots & (9,47) \\ (10,13) & (10,14) & \cdots & (10,i) & \cdots & (10,47) \\ (11,13) & (11,14) & \cdots & (11,i) & \cdots & (11,47) \\ (12,13) & (12,14) & \cdots & (12,i) & \cdots & (12,47) \end{pmatrix}$$

in which i represents one of the subgroups 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 46 and 47 defined in Tables β and γ.

The matrix ε defined below also collates additional subgroups derived from the subgroups (1,13) 2 (12,47) defined in matrix δ et and also characterised by the meaning taken by Z.

These subgroups are designated by the trinomials (l, i, k), in which (l, i) defines the subgroup from which is derived the subgroup (l, i, k), (l, i) being a subgroup of the matrix δ and k, which represents a, b or c, defines the meaning taken by Z in the subgroup (l, i, k), it being understood that:

a represents a saturated or unsaturated aliphatic hydrocarbon-based group;

b represents an optionally substituted, saturated, unsaturated and/or aromatic carbocyclic or heterocyclic radical; and c represents alk-Cy, in which alk and Cy are as defined above.

$$\varepsilon \begin{pmatrix} \begin{pmatrix} 1,13,a \\ 1,13,b \\ 1,13,c \end{pmatrix} & \begin{pmatrix} 1,14,a \\ 1,14,b \\ 1,14,c \end{pmatrix} & \cdots & \begin{pmatrix} 1,i,a \\ 1,i,b \\ 1,i,c \end{pmatrix} & \cdots & \begin{pmatrix} 1,47,a \\ 1,47,b \\ 1,47,c \end{pmatrix} \\ \begin{pmatrix} 2,13,a \\ 2,13,b \\ 2,13,c \end{pmatrix} & \begin{pmatrix} 2,14,a \\ 2,14,b \\ 2,14,c \end{pmatrix} & \cdots & \begin{pmatrix} 2,i,a \\ 2,i,b \\ 2,i,c \end{pmatrix} & \cdots & \begin{pmatrix} 2,47,a \\ 2,47,b \\ 2,47,c \end{pmatrix} \\ \begin{pmatrix} 3,13,a \\ 3,13,b \\ 3,13,c \end{pmatrix} & \begin{pmatrix} 3,14,a \\ 3,14,b \\ 3,14,c \end{pmatrix} & \cdots & \begin{pmatrix} 3,i,a \\ 3,i,b \\ 3,i,c \end{pmatrix} & \cdots & \begin{pmatrix} 3,47,a \\ 3,47,b \\ 3,47,c \end{pmatrix} \\ \begin{pmatrix} 4,13,a \\ 4,13,b \\ 4,13,c \end{pmatrix} & \begin{pmatrix} 4,14,a \\ 4,14,b \\ 4,14,c \end{pmatrix} & \cdots & \begin{pmatrix} 4,i,a \\ 4,i,b \\ 4,i,c \end{pmatrix} & \cdots & \begin{pmatrix} 4,47,a \\ 4,47,b \\ 4,47,c \end{pmatrix} \\ \begin{pmatrix} 5,13,a \\ 5,13,b \\ 5,13,c \end{pmatrix} & \begin{pmatrix} 5,14,a \\ 5,14,b \\ 5,14,c \end{pmatrix} & \cdots & \begin{pmatrix} 5,i,a \\ 5,i,b \\ 5,i,c \end{pmatrix} & \cdots & \begin{pmatrix} 5,47,a \\ 5,47,b \\ 5,47,c \end{pmatrix} \\ \begin{pmatrix} 6,13,a \\ 6,13,b \\ 6,13,c \end{pmatrix} & \begin{pmatrix} 6,14,a \\ 6,14,b \\ 6,14,c \end{pmatrix} & \cdots & \begin{pmatrix} 6,i,a \\ 6,i,b \\ 6,i,c \end{pmatrix} & \cdots & \begin{pmatrix} 6,47,a \\ 6,47,b \\ 6,47,c \end{pmatrix} \\ \begin{pmatrix} 7,13,a \\ 7,13,b \\ 7,13,c \end{pmatrix} & \begin{pmatrix} 7,14,a \\ 7,14,b \\ 7,14,c \end{pmatrix} & \cdots & \begin{pmatrix} 7,i,a \\ 7,i,b \\ 7,i,c \end{pmatrix} & \cdots & \begin{pmatrix} 7,47,a \\ 7,47,b \\ 7,47,c \end{pmatrix} \\ \begin{pmatrix} 8,13,a \\ 8,13,b \\ 8,13,c \end{pmatrix} & \begin{pmatrix} 8,14,a \\ 8,14,b \\ 8,14,c \end{pmatrix} & \cdots & \begin{pmatrix} 8,i,a \\ 8,i,b \\ 8,i,c \end{pmatrix} & \cdots & \begin{pmatrix} 8,47,a \\ 8,47,b \\ 8,47,c \end{pmatrix} \\ \begin{pmatrix} 9,13,a \\ 9,13,b \\ 9,13,c \end{pmatrix} & \begin{pmatrix} 9,14,a \\ 9,14,b \\ 9,14,c \end{pmatrix} & \cdots & \begin{pmatrix} 9,i,a \\ 9,i,b \\ 9,i,c \end{pmatrix} & \cdots & \begin{pmatrix} 9,47,a \\ 9,47,b \\ 9,47,c \end{pmatrix} \\ \begin{pmatrix} 10,13,a \\ 10,13,b \\ 10,13,c \end{pmatrix} & \begin{pmatrix} 10,14,a \\ 10,14,b \\ 10,14,c \end{pmatrix} & \cdots & \begin{pmatrix} 10,i,a \\ 10,i,b \\ 10,i,c \end{pmatrix} & \cdots & \begin{pmatrix} 10,47,a \\ 10,47,b \\ 10,47,c \end{pmatrix} \\ \begin{pmatrix} 11,13,a \\ 11,13,b \\ 11,13,c \end{pmatrix} & \begin{pmatrix} 11,14,a \\ 11,14,b \\ 11,14,c \end{pmatrix} & \cdots & \begin{pmatrix} 11,i,a \\ 11,i,b \\ 11,i,c \end{pmatrix} & \cdots & \begin{pmatrix} 11,47,a \\ 11,47,b \\ 11,47,c \end{pmatrix} \\ \begin{pmatrix} 12,13,a \\ 12,13,b \\ 12,13,c \end{pmatrix} & \begin{pmatrix} 12,14,a \\ 12,14,b \\ 12,14,c \end{pmatrix} & \cdots & \begin{pmatrix} 12,i,a \\ 12,i,b \\ 12,i,c \end{pmatrix} & \cdots & \begin{pmatrix} 12,47,a \\ 12,47,b \\ 12,47,c \end{pmatrix} \end{pmatrix}$$

it being understood that i is as defined above.

Among the preferred subgroups of the matrix ε, a distinction is made between the compounds for which $R^5$=W and those for which $R^6$=W.

The compounds of the formula I can be prepared by performing a process comprising the reaction of a compound of the formula II:

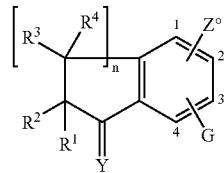

in which
$R^1$, $R^2$, $R^3$, $R^4$, n and Y are as defined above for formula I, G represents —XH, in which X is S or O; $NHCOCF_3$ or $NHR^8$, $R^8$ being as defined above for formula I, and Z° is a radical that is a precursor of Z, or alternatively Z° represents Z, Z being as defined above for formula I, Z° and G being in positions 2 and 3 of the phenyl nucleus;

with a compound of the formula III:

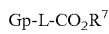

Gp-L-CO$_2$R$^7$     III in which $R^7$ and L are as defined above for formula I and Gp represents a leaving group, in the presence of a base.

The expression "Z° and G are in position 2 or 3 of the phenyl nucleus" means that either Z° or G is in position 2 and the other is in position 3. More generally, if two substituents are in positions 2 and 3, this means that one of the substituents is in position 2 and the other in position 3.

The reaction of II with III leads to the formation of a compound of the formula IV:

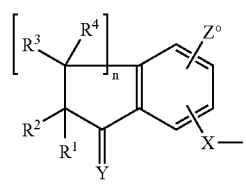

Gp may represent, for example, a halogen atom, preferably bromine, an optionally halogenated alkylsulfonyloxy group or an arylsulfonyloxy group optionally substituted by alkyl (such as mesyloxy, $CF_3$—$SO_2$—O— or p-tolylsulfonyloxy).

If Z° represents a precursor of Z, in formula II, it is preferably a halogen atom, such as I or Br or an —$OSO_2CF_3$ group.

Examples of bases include mineral bases, such as $K_2CO_3$, $Na_2CO_3$, $KHCO_3$, $NaHCO_3$ or $Cs_2CO_3$ or alternatively an organic base, such as an alkali metal alkoxide, such as sodium or potassium ethoxide, or sodium or potassium methoxide.

A stoichiometric amount of base (relative to the amount of compound III) is generally sufficient.

If $R^7$ is other than a hydrogen atom, the molar ratio of the base to compound III preferably ranges between 1 and 5 and better still between 1 and 3, for example between 1 and 2.

If $R^7$ is a hydrogen atom, the process may be performed in the presence of a large excess of base.

The reaction solvent is preferably a polar, water-miscible solvent, such as acetone or a lower $C_1$-$C_4$alkanol, for example ethanol, or dimethylformamide.

The reaction temperature is preferably maintained between 35° C. and 150° C., for example between 40 and 100° C.

The molar ratio of the compound of the formula III to the compound of the formula II ranges between 1 and 20 equivalents and preferably between 1 and 5 equivalents.

The compounds of the formula I in which Z represents Cy, in which Cy denotes an aryl or heteroaryl group can be obtained by reacting the compounds of the formula IV in which Z° represents Hal, of the formula IVa:

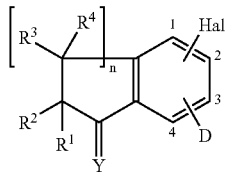

in which D represents —NHCOCF$_3$ or —X-L-CO$_2$R$^7$, and L, R$^7$, Y, X, R$^1$, R$^2$, R$^3$, R$^4$ and n are as defined for formula I, and Hal represents a halogen atom, such as Br or I, -Hal and D being in position 2 or 3 of the phenyl nucleus, with an aryl-boronic or heteroarylboronic acid of the formula V:

Cy B(OH)$_2$  (V)

in which the group Cy optionally bears one or more substituents, for example one or more substituents T as defined above, in the presence of a palladium 0 complex and a mineral or organic base.

If D represents —NHCOCF$_3$, the product resulting directly from this reaction has the formula IIa:

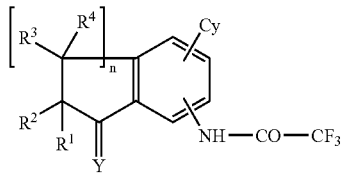

in which R$^1$, R$^2$, R$^3$, R$^4$, n and the group Cy are as defined above, and must be converted into a compound of the formula I, for example by performing the process described above.

A palladium 0 complex that will be used more particularly is tetrakis(triphenylphosphine)palladium.

Examples of mineral bases that will be mentioned include Na$_2$CO$_3$, K$_2$CO$_3$, NaHCO$_3$, KHCO$_3$, NaOH and KOH.

Examples of organic bases that may be mentioned include alkali metal alkoxides, such as sodium methoxide or ethoxide.

The reaction is preferably performed in an aromatic hydrocarbon, such as toluene, a xylene or benzene; an aliphatic hydrocarbon, such as heptane or hexane; a halogenated aromatic hydrocarbon; a C$_1$-C$_4$ lower alcohol, such as ethanol or methanol; a cyclic ether, such as tetrahydrofuran; or an amide, such as dimethylformamide.

The reaction temperature is advantageously maintained between 80 and 150° C., for example between 90 and 120° C.

According to one preferred embodiment of the invention, the molar ratio of compound V to compound IVa is between 1 and 20 and preferably between 1 and 15.

A catalytic amount of the palladium 0 complex is usually sufficient. By way of example, the molar ratio of compound IVa to the palladium complex ranges between 10 and 1000.

The base is present in the reaction medium in a proportion of from 1 to 5 equivalents and preferably 2 to 4 equivalents relative to the amount of starting compound IVa.

The compounds of the formula I in which Z represents —CH$_2$-π, in which π represents alkyl, alkenyl, alkynyl or Cy$^1$, Cy$^1$ being as defined above for Cy in formula I, or alternatively -alk$^2$-Cy$^1$, alk$^2$ representing alkylene and Cy$^1$ being as defined above, can be obtained by reacting a compound of the formula IVa as defined above with a compound of the formula VII (π-CH$_2$—)ZnBr or (π-CH$_2$)ZnCl  VII in which π is as defined above, in the presence of a palladium complex, such as bis(triphenylphosphine)dichloropalladium.

The reaction is advantageously performed in a polar aprotic solvent, for instance dimethylformamide.

Preferably, the molar ratio of compound VII to compound IVa ranges between 1 and 5 and preferably between 1 and 4.

The reaction temperature is preferably between 15 and 50° C.

The reaction solvent is preferably a polar aprotic solvent, such as dimethylformamide (DMF); an ether, such as dioxane, tetrahydrofuran (THF), diethyl ether or dimethoxyethane; or a mixture thereof, a DMF/THF mixture being preferred.

The palladium complex is used in catalytic amount, preferably in a proportion of from 0.01 to 0.1 equivalent relative to the amount of compound VII used.

The compounds of the formula I in which Y represents N—OH can be prepared from the corresponding compounds of the formula I in which Y represents O, via the action of hydroxylamine.

Conventionally, a compound of the formula VIII:

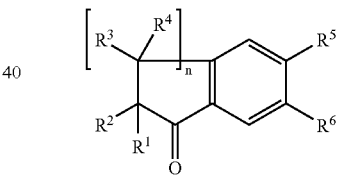

in which R$^1$, R$^2$, R$^3$, R$^4$, R$^5$, R$^6$ and n are as defined above for formula I, is reacted with a hydroxylamine salt in the presence of an alkali metal salt.

The reaction temperature is preferably between 50 and 120° C., for example between 70 and 90° C.

A hydroxylamine salt that may be mentioned is the hydrochloride or the hydrobromide.

An alkali metal salt that may be mentioned is sodium acetate.

Usually, the molar ratio of the hydroxylamine salt to the compound of the formula VIII ranges between 1 and 3 and better still between 1 and 2.

The amount of sodium acetate preferably ranges between 1 and 5 molar equivalents and better still between 2 and 3 molar equivalents relative to the amount of compound VIII used.

The solvent that can be used is, for example, a C$_1$-C$_4$ lower alkanol, such as ethanol.

The compounds of the formula I in which Y represents CR$^{10}$R$^{11}$, in which R$^{10}$ and R$^{11}$ are as defined above can be prepared from the corresponding compounds of the formula I in which Y represents O.

To do this, a compound of the formula VIII:

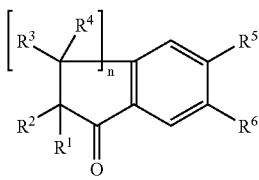

in which $R^1$, $R^2$, $R^3$, $R^4$, n, $R^5$ and $R^6$ are as defined above, is reacted with a compound of the formula IX:

$(C_6H_5)_3P^+CR^{10}R^{11}H, Br^-$  IX in which $R^{10}$ and $R^{11}$ are as defined above, in the presence of a base.

According to one preferred embodiment, the base is an alkali metal hydride, such as NaH.

This reaction is advantageously performed in a polar aprotic solvent, such as an ether, for instance tetrahydrofuran, dioxane or a diethyl ether; dimethyl sulfoxide; or an amide, such as acetamide or dimethylformamide. Preferably, the solvent is a mixture of tetrahydrofuran and dimethyl sulfoxide.

The reaction temperature ranges between −10 and +15° C., for example between 0 and 10° C.

The molar ratio of compound IX to compound VIII is preferably between 1 and 5, for example between 1 and 3 and preferably between 1 and 2.

The compounds of the formula I in which $R^7$ represents H are readily obtained from corresponding compounds of the formula I in which $R^7$ represents alkyl.

This reaction can be performed by saponification of a compound of the formula I in which $R^7$ represents alkyl, preferably methyl or ethyl, using a strong mineral base, such as NaOH or KOH.

This reaction is preferably performed in a water-miscible solvent, for example a $C_1$-$C_4$ lower alkanol, such as methanol or ethanol, as a mixture with water.

The base is preferably used in a proportion of from 1 to 5 equivalents relative to the amount of the ester of the formula I used.

For the preparation of compounds of the formula I in which $R^1$ and/or $R^2$ represents alkyl, the corresponding compound of the formula I in which $R^1$ and $R^2$ represent H can be reacted, in, a known manner, with an alkylating agent.

An example of an alkylating agent that can be used is an alkyl iodide, such as methyl iodide, while at the same time working in the presence of a hydride, such as sodium hydride.

The solvent is preferably a polar aprotic solvent, such as dimethylformamide.

By way of illustration, the molar ratio of the alkyl iodide to the starting compound of the formula I in which $R^1$ and $R^2$ are a hydrogen atom ranges between 1 and 10 and preferably between 3 and 8.

The amount of base that needs to be used preferably ranges between 1 and 5 equivalents relative to the starting compound of the formula I.

This base is advantageously an alkali metal hydride, such as sodium hydride.

This reaction is usually performed at a temperature of between 0° and 100° C., for example between 20 and 60° C.

This alkylation step can be performed in a similar manner starting with an intermediate compound, during the synthesis of the compound of the formula I.

The compounds of the formula I in which Z represents a saturated aliphatic hydrocarbon-based radical can be obtained from the corresponding compounds of the formula I in which Z represents an unsaturated aliphatic hydrocarbon-based radical, by simple catalytic hydrogenation under a hydrogen atmosphere in the presence of a catalyst, such as palladium-on-charcoal.

By way of example, a compound of the formula I in which Z is an aliphatic hydrocarbon-based radical comprising a triple bond or a double bond can be converted via catalytic hydrogenation into the corresponding compound of the formula I in which Z is a saturated hydrocarbon-based radical.

Typical reaction conditions are:

an $H_2$ pressure of from 1.5 to 5 bar;

a catalyst: 5 to 10% palladium-on-charcoal;

a solvent, such as a $C_1$-$C_4$ lower alkanol, for instance ethanol;

a reaction temperature of between 15 and 60° C.

The compounds of the formula II:

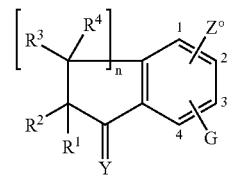

in which $R^1$, $R^2$, $R^3$, $R^4$, $Z°$, n and G are as defined above, Y represents O and n represents 1, can be prepared by cyclisation of the corresponding compounds of the formula X:

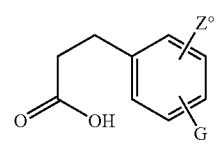

in which $Z°$ and G are as defined above, in the presence of an acid, at a temperature of between 40 and 180°, or even between 50 and 150° C., preferably between 70 and 130° C.

A suitable acid is polyphosphoric acid.

The molar amount of polyphosphoric to compound X preferably ranges between 4 and 50 equivalents.

The reaction is advantageously performed in a solvent, such as an optionally halogenated aliphatic hydrocarbon, such as hexane, heptane, dichloromethane, tetrachloromethane or chloroform, or an optionally halogenated aromatic hydrocarbon, such as toluene, benzene, xylene or a chlorobenzene.

The compounds of the formula II in which $R^1$, $R^2$, $R^3$, $R^4$ and $Z°$ are as defined above, and G represents methoxy, Y represents O and n represents I can be prepared by cyclisation of a compound of the formula X in which G represents —O—$CH_3$, under the same conditions as described above for the cyclisation of compound X.

The compounds of the formula II:

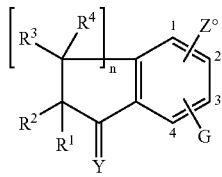

in which $R^1$, $R^2$, $R^3$, $R^4$, n, $Z°$ and G are as defined above and Y represents O and n=1, can be obtained by cyclisation of a corresponding compound of the formula XI:

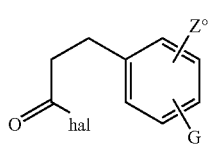

in which hal is a halogen atom, and $Z°$ and G are as defined above, in the presence of a Lewis acid, such as $AlCl_3$ or a mineral acid.

The reaction is usually performed at a temperature of between 15° C. and 100° C.

Preferably, the molar ratio of $AlCl_3$ to the compound of the formula XI ranges between 1 and 5 and better still between 2 and 4.

The solvent is preferably a halogenated aliphatic hydrocarbon, such as dichloromethane.

The compound of the formula XI can be simply prepared from the corresponding acid of the formula X via the action of $SOCl_2$. This reaction is usually performed at a temperature of between 40 and 80° C.

According to one preferred embodiment, the solvent is a halogenated aliphatic hydrocarbon as defined above.

This same cyclisation reaction can be performed using a compound of the formula XI in which G represents —$OCH_3$. In this case, it leads to the corresponding compound of the formula II in which G represents —$OCH_3$.

The compounds of the formula X are commercially available or prepared simply by carrying out conventional processes using commercially available products.

The compounds XII of the general formula II in which $Z°$, in position 2, represents I and G, in position 3, represents —OH, can be obtained from the corresponding compounds of the formula XIII by carrying out reaction scheme 1.

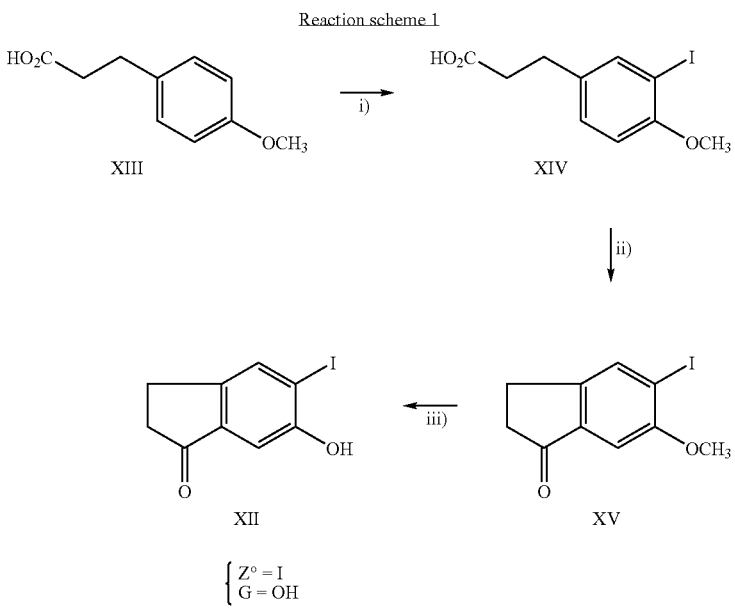

In step i), a compound of the formula XIII is reacted with ICl in acetic acid medium.

Preferably, the amount of ICl ranges between 1 and 3 equivalents and preferably between 1 and 2 equivalents.

The reaction temperature is between 50 and 120° C., for example between 80 and 100° C.

In step ii), cyclisation of the compound of the formula XIV is carried out by performing a process similar to the one described in the case of the compound of the formula X.

In this case, it is possible to work at a temperature of between 40° C. and 180° C.

In step iii), the compound of the formula XV is treated, at a temperature of between 40° C. and 180° C. and preferably between 60° C. and 140° C., with a Lewis acid, such as $AlCl_3$. Advantageously, the $AlCl_3$ is used in a proportion of from 1 to 10 equivalents, for example from 1 to 5 equivalents, relative to the amount of compound XV present in the medium.

The reaction solvent is preferably an aromatic solvent, such as toluene, benzene or xylene.

The compounds of the formula X in which G, in position 3, represents —OCH$_3$, can be obtained by performing a process comprising the steps of reaction scheme 2:

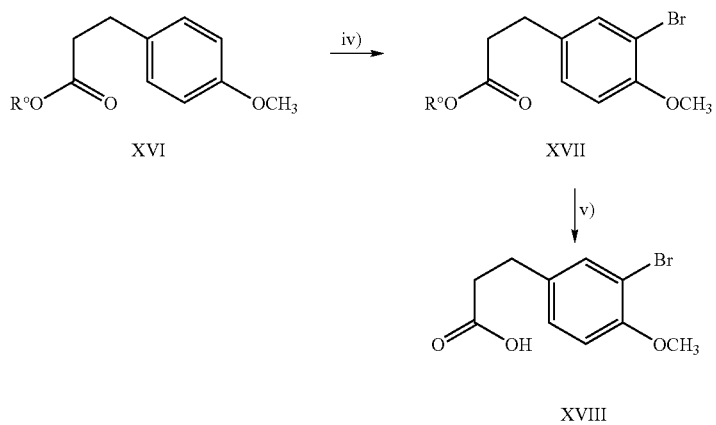

Reaction scheme 2

R° being C$_1$–C$_4$ lower alkyl

In step iv), bromine is reacted with the compound of the formula XVI.

The reaction solvent is preferably a halogenated aliphatic hydrocarbon chosen from tetrachloromethane, chloroform and dichloromethane.

The reaction temperature is preferably between 15 and 35° C.

The molar ratio of bromine to the compound of the formula XVI usually ranges between 1 and 1.5.

In step v), the compound obtained of the formula XVII is saponified in a conventional manner, for example via the action of KOH or NaOH, for example in a mixture of water and of C$_1$-C$_4$ lower alkanol.

The compounds of the formula II in which G represents —OH, n represents 2, Y represents O and Z° represents 1-alkyl can be obtained by performing the process illustrated in reaction scheme 3:

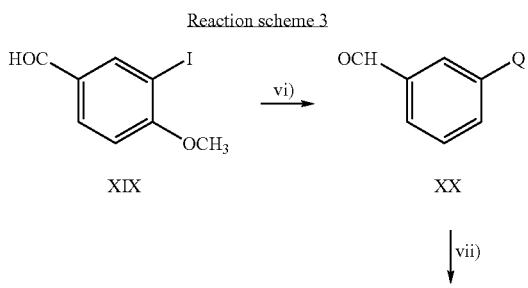

Reaction scheme 3 in which Q represents 1-alkynyl and M represents alkyl.

In step vi), a 1-alkyne is reacted with the compound of the formula XIX in the presence of a palladium complex, copper iodide and a base.

An example of a palladium complex that will advantageously be used is PdCl$_2$(PPh$_3$)$_2$.

The reaction is preferably performed in a solvent, preferably an ether, such as tetrahydrofuran, dioxane, diethyl ether or dimethoxyethane.

The molar ratio of the 1-alkyne to the compound of the formula XIX preferably ranges between 1 and 3 and better still between 1 and 2.

Advantageously, the amount of CuI ranges between 0.05 and 2 equivalents relative to the amount of compound of the formula XIX.

The base that can be used is either triethylamine, 4-dimethylaminopyridine, pyridine, 2,6-di-tert-butylpyridine, 1,8-diazabicyclo[5.4.0]undec-7-ene (DBU), 1,5-diazabicyclo

[4.3.0]non-5-ene (DBN) and 1,4-diazabicyclo[2.2.2]-octane, or a mineral base, such as $K_2CO_3$.

In step vii), the compound of the formula XX is reacted with a phosphonium bromide of the formula:

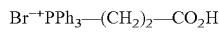

XXIII in the presence of a hydride.

The general working conditions are those recommended in the technique for Wittig reactions.

This reaction is advantageously performed in an ether/dimethyl sulfoxide mixture. A preferred ether that will be used is tetrahydrofuran.

An example of a hydride that may be mentioned is sodium hydride.

The molar ratio of the bromide XXIII to compound XX is usually between 1 and 5, for example between 1 and 3.

In step viii), hydrogenation of compound XXI is performed under the same conditions as described above, followed by cyclisation via the action of a sulfonic acid.

In step ix), the compound of the formula XXII is treated with $AlCl_3$ in an aromatic solvent, such as toluene, under the same conditions as described above for step iii) of reaction scheme 1.

The compound of the formula II in which G represents —SH can be prepared by performing the process illustrated in reaction scheme 4:

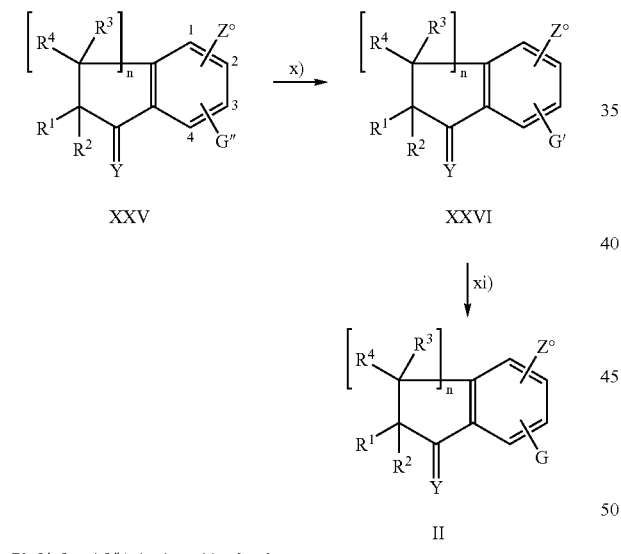

$Z°$, $G'$, G and $G''$ being in position 2 or 3 in which $G''$ represents OH; $G'$ represents —O—$SO_2$—$CF_3$.

The compound of the formula XXV is treated with 1 to 5 equivalents and preferably 1 to 3 equivalents of triflic anhydride in the presence of a base.

A solvent for this reaction that will advantageously be used is pyridine, which also acts as the base.

In step xi), a silanethiol, such as triisopropylsilanethiol is reacted with the compound of the formula XXVI in the presence of a hydrides such as sodium hydride and a palladium 0 complex, such as $Pd(PPh_3)_4$.

An ether, such as tetrahydrofuran, dioxane, diethyl ether or dimethoxyethane will advantageously be used as solvent.

The hydride and the triisopropylsilanethiol are placed in contact at a temperature of between —10° C. and +10° C., and the reaction medium is then brought to a temperature of between 50 and 150° C. and preferably between 70 and 100° C., after addition of compound XXVI.

The amounts of compound XXVI, of hydride and of silanethiol are advantageously stoichiometric.

The compound obtained is treated with tetrabutylammonium fluoride, preferably in an ether, such as dioxane or tetrahydrofuran, in a conventional manner, this reaction allowing the thiol function to be deprotected.

The compounds of the formula I in which X represents SO or $SO_2$ are obtained by oxidation of the corresponding compounds of the formula I in which X represents S.

The oxidising agent is, for example, meta-chloroperbenzoic acid, which is used in the reaction medium in a proportion of from 1 to 5 and preferably 1 to 3 equivalents.

The solvent is preferably a halogenated aliphatic hydrocarbon, such as carbon tetrachloride, dichloromethane or chloroform.

The reaction is advantageously performed at a temperature of from —10° C. to +10° C.

As a variant, this oxidation reaction can be performed using a reaction intermediate during the synthesis of the compounds of the formula I.

The compounds of the formula II in which G represents —NH—CO—$CF_3$ can be prepared from the corresponding compounds of the formula XXVII:

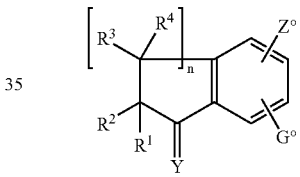

XXVII in which $R^1$, $R^2$, $R^3$, $R^4$, Y, $Z°$ and n are as defined above, and $G°$ represents —$NO_2$, by performing a process comprising the steps consisting in:

a) reacting the compound of the formula XXVII with iron (0) in the presence of ammonium chloride;

b) and then reacting the resulting compound with trifluoroacetic anhydride in acetic medium.

In step a), the process will preferably be performed in the presence of an excess of iron (0). The molar ratio of the iron to compound XXVII ranges especially between 2 and 10 equivalents and better still between 3 and 7 equivalents.

As regards the amount of ammonium chloride, this preferably ranges between 0.1 and 1 equivalent relative to the amount of compound of the formula XXVII.

The reaction temperature is advantageously between 40 and 120° C., for example between 50 and 90° C.

The solvent preferably consists of a mixture of water and of a $C_1$-$C_4$ lower alkanol.

By way of illustration, a mixture of water and ethanol will be selected.

In step b), the process is performed in acetic acid as solvent. The molar ratio of the trifluoroacetic anhydride to the amine obtained after step a) advantageously ranges between 1 and 1.5 equivalents.

The reaction temperature advantageously ranges between —10° C. and +10° C., for example between —5 and 0° C.

The compounds of the formula Xa in which G represents —O—CH₃ and Z° represents alkyl can be obtained by performing the process illustrated in reaction scheme 5.

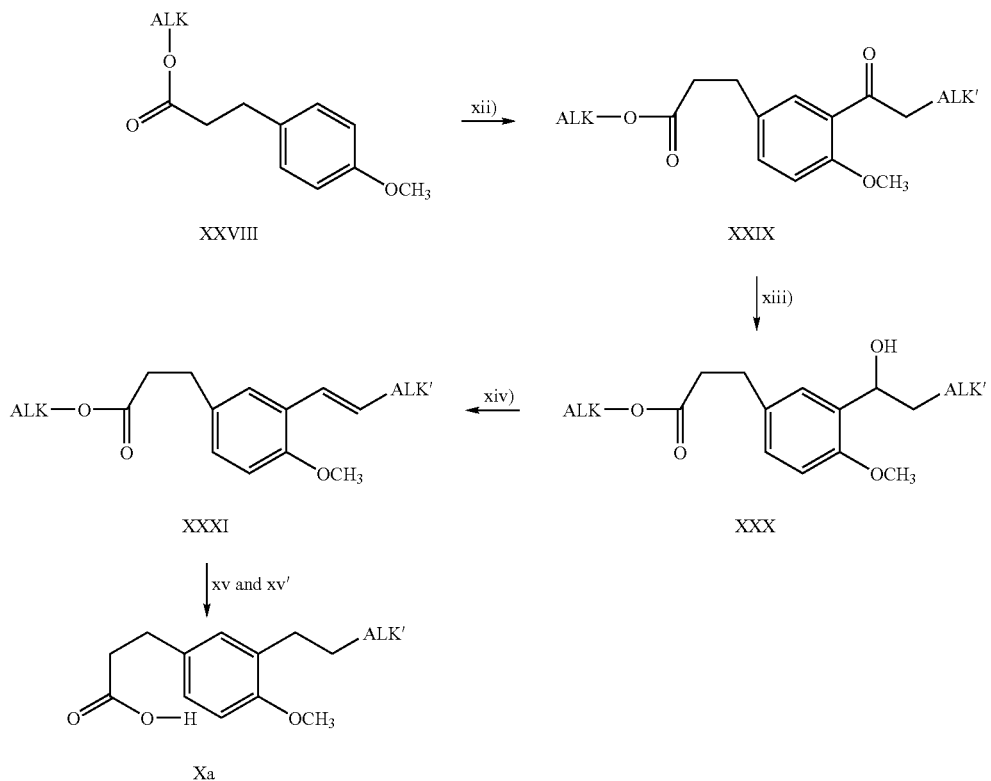

in which ALK and ALK' independently represent lower alkyl, for example $C_1$-$C_4$alkyl.

In step xii), a compound of the formula XXVIII is reacted with an acid chloride of the formula XXXII:

Cl—CO—CH₂-ALK'  XXXII in the presence of a Lewis acid, such as aluminium chloride.

The process is preferably performed in the presence of 1 to 5 equivalents of Lewis acid relative to compound XXVIII.

The solvent is preferably chosen from a halogenated aliphatic hydrocarbon, such as dichloromethane, chloroform or carbon tetrachloride.

The reaction temperature ranges between 25 and 100° C.

The molar ratio between the acid chloride of the formula XXXII and the compound of the formula XXVIII usually ranges between 1 and 5, for example between 1 and 3.

In step xiii), reduction of compound XXIX obtained is performed via the action of a suitable hydride, in a conventional mariner. By way of example, an alkali metal borohydride is used, such as sodium borohydride, and the process is performed in a $C_1$-$C_4$alkanol.

The borohydride and the ketone of the formula XXIX are preferably used in stoichiometric amounts.

In step xiv), compound XXX is dehydrated via the action of a dehydrating agent, such as p-toluenesulfonic acid, while working in an aromatic hydrocarbon, such as toluene. The p-toluenesulfonic acid is used in a proportion of from 0.01 to 1 equivalent.

Next, in step xv), hydrogenation of the double bond is performed via the action of hydrogen, in the presence of palladium-on-charcoal. This reaction is preferably performed under the reaction conditions described above.

The resulting compound is then saponified in a conventional manner, in step xv'). To do this, a mineral base chosen from $K_2CO_3$, $Na_2CO_3$, $NaHCO_3$, $KHCO_3$, KOH and NaOH will preferably be used, and will be reacted with the ester obtained in the preceding step, the reaction preferably taking place in a mixture of lower alkanol (preferably a $C_1$-$C_4$alkanol) and water, such as an ethanol/water or methanol/water mixture. The amount of base preferably ranges between 1 and 5 molar equivalents relative to the initial amount of ester.

The compounds of the formula II in which G represents —XH in which X is O can be prepared from the corresponding compounds of the formula XXXIII:

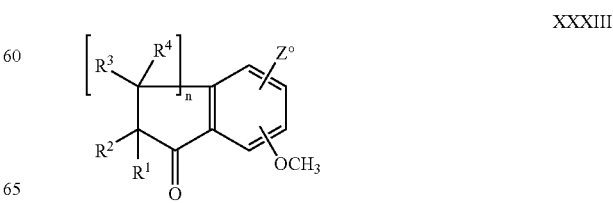

in which $R^1$, $R^2$, $R^3$, $R^4$, n and $Z°$ are as defined above, by reacting these compounds with a strong Lewis acid, such as aluminium chloride.

This reaction is performed, for example, in a polar aprotic solvent, for instance an aromatic hydrocarbon, such as benzene or toluene.

The molar ratio of $AlCl_3$ to the compound of the formula XXXIII preferably ranges between 1 and 5 and preferentially between 2 and 3.

This reaction is advantageously performed at a temperature of between 50° and 120° C., for example between 90° and 110° C.

The compounds of the formula XXXIII can be readily prepared by performing the following reaction scheme:

Reaction scheme 6

XXXIV → XXXV

↓ xvii)

XXXIII

In step xvi), the compound of the formula XXXIV is reacted with triflic anhydride. This reaction is advantageously performed in a solvent of polar aprotic type in the presence of a base, such as a base chosen from pyridine, 4-dimethylaminopyridine, 2,6-di-tert-butylpyridine, 1,8-diazabicyclo[5.4.0]undec-7-ene (DBU), 1,5-diazabicyclo[4.3.0]non-5-ene (DBN) and 1,4-diazabicyclo-[2.2.2]octane. If the selected base is pyridine, it may advantageously be used as solvent.

The molar ratio of the triflic anhydride to the compound of the formula XXXIV advantageously ranges between 1 and 2 equivalents.

The reaction is preferably performed at a temperature of between −10° and +15°, for example between −5° and +5° C.

In step xvii), compound XXXV obtained in the preceding step is reacted with a compound of the formula XXXVI:

Z°-ZnBr                                                                 XXXVI in which Z° is as defined above, in the presence of a palladium complex. A palladium complex that may be mentioned is dichlorobis(triphenylphosphine)palladium.

This reaction is preferably performed in a polar aprotic solvent, such as dimethylformamide, acetamide, dimethylacetamide, formamide or hexamethylphosphorylamide. Usually, a molar ratio of compound XXXVI to compound XXXV of between 1 and 3 equivalents and preferably between 1 and 2 equivalents is used. The reaction temperature will preferably be maintained between 15° and 50° C. and better still between 20° and 40° C.

The solvent that can be used for this reaction is preferably a polar aprotic solvent, such as an ether, or dimethylformamide. Ethers that may be mentioned include cyclic ethers, such as dioxane or tetrahydrofuran, or a linear ether, such as diethyl ether, di-tert-butyl ether or a glyme, such as diglyme. The solvent is preferably tetrahydrofuran.

Some of the intermediate compounds described above are novel.

The invention relates to these novel intermediate compounds. Among the preferred intermediate compounds of the invention, the following subgroups will be distinguished:

1) a compound of the formula II

II in which:

$R^1$ and $R^2$ are chosen independently from a hydrogen atom and a $C_1$-$C_6$alkyl group, such as methyl; $Z°$ represents I, Br or a $C_1$-$C_{10}$alkyl group; and G represents —OH; —SH; —$NH_2$; —$OCH_3$; —NH—CO—$CH_3$; —NH—CO—$CF_3$;

2) a compound of the formula II chosen from:
2,2-dimethyl-5-n-hexyl-6-hydroxyindan-1-one;
5-n-hexyl-6-hydroxyindan-1-one;
5-n-hexyl-6-mercaptoindan-1-one;
5-iodo-6-methoxyindan-1-one;
5-bromo-6-aminoindan-1-one;
5-bromo-6-hydroxyindan-1-one;
2,2-dimethyl-5-n-hexyl-6-methoxyindan-1-one; and
5-bromo-6-trifluoromethylcarbonylaminoindan-1-one;

3) a compound of the formula $IVb^2$:

$IVb^2$ in which:

$R^1$ and $R^2$ are chosen independently from a hydrogen atom and a $C_1$-$C_6$alkyl group, such as —$CH_3$; Halo represents a halogen atom, such as an iodine atom; L and $R^7$ are as defined above, it being understood that Hal° and —O-L-$CO_2R^7$ are in position 2 or 3.

4) a compound of the formula $IVb^2$ in which $R^1$ and $R^2$ are hydrogen atoms;

Hal° represents a bromine or iodine atom and is in position 2; and —O-L-$CO_2R^7$ is in position 3;

5) a compound of the formula XXVIIa:

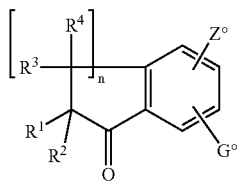

XXVIIa in which
R$^1$ and R$^2$ represent a hydrogen atom or a (C$_1$-C$_6$)alkyl group, such as —CH$_3$;
Z° is as defined above for formula II; and G° represents NO$_2$;
6) 5-bromo-6-nitroindan-1-one;
7) a compound of the formula XX:

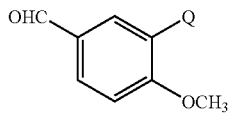

XX in which Q represents C$_2$-C$_{10}$ 1-alkynyl, preferably 1-hexynyl;
8) an intermediate compound in the preparation of the compounds of the formula I, chosen from:
5-methoxy-6-trifluoromethylsulfonyloxyindan-1-one;
5-methoxy-6-bromoindan-1-one; and
5-hydroxy-6-bromoindan-1-one.

According to another of its aspects, the invention relates to a pharmaceutical composition comprising at least one compound of the formula I in combination with at least one pharmaceutically acceptable excipient.

These compositions can be administered orally in the form of tablets, gel capsules or granules with immediate release or controlled release, intravenously in the form of an injectable solution, or transdermally in the form of a solution, cream or gel.

The compounds are preferably administered in doses from about 1 to 100 mg and in particular from about 10 to 200 mg per dosage unit. The daily dose is preferably within the range from 10 to 200 mg/kg of body weight. However, the specific dose for each patient depends on a wide variety of factors, especially including the efficacy of the specific compound used, the age, the body weight, the general state of health, the sex, the diet, the time and mode of administration, the level of excretion, the combination with other medicaments and the acute nature of the particular disease targeted by the therapy. Oral administration is preferred.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, calcium citrate, shellac, hydroxypropylcellulose, acacia, gum tragacanth, gelatine, hydroxypropylmethylcellulose, calcium citrate [sic], dextrin and pectin. Examples of lubricants include magnesium stearate, talc, polyethylene glycol, silica and hardened plant oils. The colorant may be any of those permitted for used in medicaments. Examples of flavour enhancers include cocoa powder, mint in herb form, aromatic powder, mint in oil form, borneol and cinnamon powder.

Obviously, the tablet or granule can be suitably coated with sugar, gelatine or the like.

An injectable form comprising the compound of the present invention as active principle is prepared, where appropriate, by mixing the said compound with a pH regulator, a buffer agent, a suspension agent, a solubiliser, a stabiliser, an isotonic agent and/or a preserving agent, and by converting the mixture into a form for intravenous, subcutaneous or intramuscular injection, according to a standard process. Where appropriate, the injectable form obtained can be freeze-dried via a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilisers include castor oil solidified with polyoxyethylene, polysorbate 80, nicotinamide, polyethoxylated sorbitan monolaurate and the ethyl ester of castor oil fatty acid.

In addition, the stabiliser encompasses sodium sulfite, sodium metasulfite and ether, while the preserving agent encompasses methyl p-hydroxybenzoate, ethyl p-hydroxybenzoate, sorbic acid, phenyl [sic], cresol and chlorocresol.

The invention is also directed towards medicaments comprising at least one compound of the formula I and/or the pharmaceutically acceptable derivatives, solvates and stereoisomers thereof, and also mixtures thereof in all proportions, and optionally one or more excipients and/or adjuvants.

The compounds of the invention are powerful activators of the PPARα and PPARγ isoforms. As a result of this activity, they have a substantial hypolipidaemiant and hypoglycaemiant effect.

Thus, the invention is also directed towards the use of a compound of the formula I and/or the pharmaceutically acceptable derivatives, solvates and stereoisomers thereof, including mixtures thereof in all proportions, for the preparation of a medicament for the treatment of an individual suffering from a disease or condition mediated by an insufficiency of activity of the PPARα and PPARγ isoforms in their role of regulating lipidaemia and glycaemia.

In particular, the invention is directed towards the use of a compound of the formula I and/or the pharmaceutically acceptable derivatives, solvates and stereoisomers thereof, including mixtures thereof in all proportions, for the preparation of a medicament for the prevention of or treating dyslipidaemia, atherosclerosis and diabetes.

The measurement of the PPAR activation was performed according to a technique described by Lehmann et al. (1995, J. Biol. Chem. 270: 12953-12956).

CV-1 cells (monkey kidney cells) are co-transfected with an expression vector for the chimeric proteins PPARα-Gal4 or PPARγ-Gal4 and with a "reporter" plasmid that allows the expression of the luciferase gene placed under the control of a promoter containing Gal4 response elements.

The cells are plated into 96-well microplates and co-transfected using a commercial reagent with the reporter plasmid (pG5-tk-pGL3) and the expression vector for the chimeric protein (PPARα-Gal4 or PPARγ-Gal4). After incubating for 4 hours, whole culture medium (comprising 10% foetal calf serum) is added to the wells. After 24 hours, the medium is removed and replaced with whole medium comprising the test products (50 μM final). The products are left in contact with the cells for 18 hours. The cells are then lysed and the luciferase activity is measured using a luminometer. A PPAR activation factor can then be calculated by means of the activation of the expression of the reporter gene induced by the product (relative to the control cells that have not received any product).

By way of example, the compound of Example 1, at a concentration of 50 µM, activates the chimeric protein PPARα-Gal4 by factor of 18, and the chimeric protein PPARγ-Gal4 by a factor of 39. In the absence of the binding domain for the PPAR α or γ ligand (vector expressing Gal4 alone), the luciferase activity measured in the presence of this product is zero.

The present invention is illustrated below with the aid of the examples that follow.

The frequency of the NMR machine used to record the proton spectra in the examples given below is 300 MHz.

s denotes a singlet; d a doublet; t a triplet; q a quartet; sept. a septet, and m is a multiplet.

m.p. denotes the melting point.

EXAMPLES

Example 1

Step a:
ethyl3-(3-hexanoyl-4-methoxyphenyl)propanoate 98 ml (0.7 mol) of hexanoyl chloride are added dropwise to a solution of 70 g (0.336 mol) of ethyl3-(4-methoxyphenyl) propanoate in 280 ml of dichloromethane. 89 g (0.67 mol) of aluminium chloride are then added in small amounts, and the mixture is heated for one hour at 50° C. The mixture is poured into cold water and extracted with ether. The organic phase is washed with sodium bicarbonate solution. After drying ($Na_2SO_4$) and evaporating off the solvents, a yellow liquid is obtained, and then distilled: $Bp_{0.4\ mmHg}$=160° C. (74 g; 72%);

$^1$H NMR —$CHCl_3$—δ(ppm): 0.88 (3H, m); 1.21 (3H, m); 1.30 (4H, m); 1.64 (2H, m); 2.57 (2H, m); 2.92 (4H, m); 3.85 (3H, s); 4.10 (2H, m); 6.85 (1H, m); 7.27 (1H, m); 7.45 (1H, m).

Step b: ethyl3-[3-(1-hydroxyhexyl)-4-methoxyphenyl)propanoate $NaBH_4$ (7.6 g; 0.2 mol) is added in small amounts to 61 g (0.2 mol) of ethyl3-(3-hexanoyl-4-methoxyphenyl)propanoate, as a solution in 500 ml of ethanol. The mixture is heated for 1 hour at 80° C. After 16 hours at room temperature, the mixture is concentrated under vacuum and poured into saturated sodium chloride solution. The resulting mixture is extracted with ether and the organic phase is dried over sodium sulfate. Evaporation of the solvents gives 58 g of product in a 94% yield.

$^1$H NMR —$CHCl_3$—δ (ppm): 0.87 (3H, m); 1.22 (3H, m); 1.28 (4H, m); 1.69 (1H, m); 1.73 (3H, m); 2.56 (3H, m); 2.87 (2H, m); 3.81 (3H, s); 4.11 (2H, m); 4.80 (1H, broad m); 6.78 (1H, m); 7.03 (1H, m); 7.11 (1H, m).

Step c:
ethyl3-(3-hexyl-1-enylmethoxyphenyl)propanoate

A solution of 58 g (0.188 mol) of ethyl3-[3-(1-hydroxyhexyl)-4-methoxyphenyl)propanoate and 2.8 g (14.7 mmol) of para-toluenesulfonic acid in 500 ml of toluene is heated for 3 hours. The water-toluene azeotrope is removed using Dean-Stark apparatus. After cooling, the organic phase is washed with water, separated out by settling of the phases, and dried ($Na_2SO_4$). Evaporation under vacuum of the solvent gives 54.6 g (100%) of an orange oil.

$^1$H NMR —$CHCl_3$—δ (ppm): 0.92 (3H, m); 1.23 (3H, m); 1.40 (4H, m); 2.22 (2H, m); 2.58 (2H, m); 2.87 (2H, m); 3.81 (3H, s); 4.12 (2H, m); 6.02-6.37 (1H, m); 6.58-6.83 (2H, m); 7.00 (1H, m); 7.11-7.30 (1H, m).

Step d:
ethyl3-(3-hexyl-4-methoxyphenyl)propanoate 54.6 g (0.188 mol) of ethyl3-(3-hexyl-1-enyl-4-methoxyphenyl)propanoate are hydrogenated with 0.8 g of palladium-on-charcoal in 150 ml of ethanol under pressure (200 bar). After filtration of the catalyst and evaporation of the solvent, 45.7 g of product are collected (83%).

$^1$H NMR —$CHCl_3$—δ (ppm): 0.88 (3H, m); 1.24 (3H, m); 1.31 (6H, m); 1.55 (2H, m); 2.57 (4H, m); 2.87 (2H, m); 3.78 (3H, s); 4.12 (2H, m); 6.74 (1H, m); 6.88-7.04 (2H, m)

Step e: 3-(3-hexyl-4-methoxyphenyl)propanoic acid

A mixture of 45.7 g (0.156 mol) of the compound obtained in step d) and 300 ml of ethanol, 13 g (0.232 mol) of potassium hydroxide and 150 ml of water is heated for 75 minutes at the reflux point of the solvents. The solvents are evaporated off, and the residue is taken up in water and extracted with ether. The aqueous phase is acidified and then extracted with ether. Concentration of the solvents gives a yellow oil which crystallises (36 g; 87%).

$^1$H NMR —$CHCl_3$—δ (ppm): 0.88 (3H, m); 1.30 (6H, m); 1.54 (2H, m); 2.56 (2H, m); 2.63 (2H, m); 2.87 (2H, m); 3.79 (3H, s); 6.75 (1H, m); 6.91-7.04 (2H, m).

Step f: 5-hexyl-6-methoxyindan-1-one 18.5 g (69.9 mmol) of 3-(3-hexyl-4-methoxyphenyl)propanoic acid dissolved in 100 ml of xylene are added to a mixture of 100 g of polyphosphoric acid and 100 ml of xylene heated to 80° C. The mixture is then heated at 135° C. for 1 hour 30 minutes. The mixture is poured into water and extracted with ethyl acetate. The organic phase is washed with sodium bicarbonate solution. The solvents of the organic phase are dried ($Na_2SO_4$) and evaporated off, and the residue is purified by flash chromatography (9 g; 52%).

$^1$H NMR —$CHCl_3$—δ (ppm): 0.88 (3H, m); 1.31 (6H, m); 1.57 (2H, m); 2.66 (4H, m); 3.03 (2H, m); 3.84 (3H, s); 7.13 (1H, s); 7.21 (1H, s).

Step g: 5-hexyl-6-hydroxyindan-1-one 5.6 g (22.7 mmol) of 5-hexyl-6-methoxyindan-1-one, 9.4 g of aluminium chloride and 125 ml of toluene are refluxed for 15 minutes. The mixture is poured into water and extracted with ether. The organic phase is dried ($Na_2SO_4$) and the solvents are evaporated off. The residue is purified by flash chromatography (4.5 g; 85%).

$^1$H NMR —$CHCl_3$—δ (ppm): 0.88 (3H, m); 1.32 (6H, m); 1.65 (2H, m); 2.67 (4H, m); 3.03 (2H, m); 5.54 (1H, s); 7.15 (1H, s); 7.21 (1H, s).

Step h: ethyl4-(6-hexyl-3-oxoindan-5-yloxy)butyrate 3.6 ml of ethyl4-bromobutyrate dissolved in 15 ml of ethanol are added to a mixture of sodium ethoxide (1.6 g, 0.0233 mol) and 5-hexyl-6-hydroxyindan-1-one (4.5 g, 0.0194 mol) in 45 ml of ethanol. The reaction medium is heated for 5 hours at reflux. The mixture is poured into water and extracted with ether. The organic phase is dried (Na$_2$SO$_4$) and the solvents are evaporated off (5.9 g; 60%).

$^1$H NMR —CHCl$_3$—δ (ppm): 0.88 (3H, m); 1.25 (3H, m); 1.31 (6H, m); 1.59 (2H, m); 2.13 (2H, m); 2.51 (2H, m); 2.67 (4H, m); 3.02 (2H, m); 4.01 (2H, m); 4.14 (2H, m); 7.10 (1H, s); 7.21 (1H, s).

Step i: 4-(6-hexyl-3-oxoindan-5-yloxy)butyric acid

A mixture of 70 ml of ethanol, 2.7 g (0.048 mol) of potassium hydroxide, 5.9 g (0.017 mol) of ethyl4-(6-hexyl-3-oxoindan-5-yloxy)butyrate and 35 ml of water is heated for 90 minutes at the reflux point of the solvents. The solvents are evaporated off and the residue is placed in water and extracted with ether. The aqueous phase is acidified and then extracted with ether. Concentration of the solvents gives 3.6 g of product, which is purified by flash chromatography (80/20 cyclohexane/ethyl acetate): 1.5 g of crude product. Recrystallisation from hexane gives 1.3 g, m.p. 88° C., 24%.

$^1$H NMR-DMSO—δ(ppm): 0.84 (3H, m); 1.27 (6H, m); 1.53 (2H, m); 1.95 (2H, m); 2.40 (2H, m); 2.60 (4H, m); 2.97 (2H, m); 4.02 (2H, m); 7.02 (1H, s); 7.33 (1H, s); 12.13 (1H, broad s).

Example 2

Ethyl4-[3-methylene-6-hexylindan-5-yloxy]butyrate 5.4 g (15.3 mmol) of methyltriphenylphosphate [sic] bromide are added to a suspension of 1.75 g (14.9 mmol) of potassium tert-butoxide in 20 ml of tetrahydrofuran. The reaction medium is stirred for 1 hour at 25° C. and then cooled to 0° C. A solution of 4.5 g (12.9 mmol) of ethyl4-(6-hexyl-3-oxoindan-5-yloxy)butyrate is added. The mixture is stirred for 16 hours at 25° C., poured into water and extracted with ether. The organic phase is dried (Na$_2$SO$_4$) and concentrated under reduced pressure (oil). Purification by flash chromatography (80/20 heptane/ethyl acetate) gives an orange oil (3.5 g; 79%).

$^1$H NMR-DMSO—δ (ppm): 0.84 (3H, m); 1.16 (3H, m); 1.27 (6H, m); 1.48 (2H, m); 1.98 (2H, m); 2.45 (4H, m); 2.71 (2H, m); 2.78 (2H, m); 3.99 (2H, m); 4.06 (2H, m); 4.93 (1H, m); 5.42 (1H, m); 7.01 (1H, s); 7.04 (1H, s).

Example 12

4-(3-methylene-6-hexylindan-5-yloxy)butyric acid

A mixture of 20 ml of ethanol, 0.975 mg (155 mmol) of potassium hydroxide, 1.2 g (35 mmol) of ethyl4-(3-methylene-6-hexylindan-5-yloxy)butyrate and 10 ml of water is heated for 5 hours at the reflux point of the solvents. The ethanol is evaporated off, the residue is taken up in water and the impurities are extracted with ether. The aqueous phase is acidified and then extracted with ether. Concentration of the solvents gives 1.1 g of product, which is purified by flash chromatography (50/50 heptane/ethyl acetate) to give a solid m.p.: 90° C. (0.8 g; 72%).

$^1$H NMR-DMSO—δ (ppm): 0.87 (3H, m); 1.31 (6H, m); 1.57 (2H, m); 2.12 (2H, m); 2.16 (2H, m); 2.63 (4H, m); 3.22 (2H, m); 4.07 (2H, m); 6.14 (1H, m); 6.80 (1H, m); 7.19 (1H, s); 7.26 (1H, s).

Example 18

Step a: 5-hexyl-6-methoxy-2,2-dimethylindan-1-one 5 g (0.02 mol) of 5-hexyl-6-methoxyindan-1-one dissolved in 20 ml of dimethylformamide are added dropwise to a suspension of 1.8 g (0.04 mol) of sodium hydride in 20 ml of dimethylformamide at 25° C. The mixture is stirred for 15 minutes at this temperature, and 11.4 g (0.1 mol) of methyl iodide are then added, while maintaining the temperature below 30° C. The reaction medium is stirred for 16 hours at 25° C. A further 0.9 g (0.0375 mol) of sodium hydride is added, and 15 minutes later 11.4 g (0.1 mol) of methyl iodide are added and the mixture is stirred for 2 hours at 25° C. The mixture is then heated for 1 hour at 50° C. It is poured into water and extracted with ether. The organic phase is dried (Na$_2$SO$_4$) and then evaporated under reduced pressure. The orange oil obtained is purified by flash chromatography (dichloromethane, 3.54 g; 65%).

$^1$H NMR —CHCl$_3$—δ (ppm): 0.97 (3H, m); 1.30 (6H, s); 1.41 (6H, m); 1.67 (2H, m); 2.74 (2H, m); 2.98 (2H, s); 3.93 (3H, s); 7.22 (1H, s); 7.34 (1H, s).

Step b: 5-hexyl-6-hydroxy-2,2-dimethylindan-1-one 1.93 g (7 mmol) of 5-hexyl-6-methoxy-2,2-dimethylindan-1-one, 2.84 g (21 mmol) of aluminium chloride and 40 ml of toluene are heated for 15 minutes at reflux. The mixture is poured into water and extracted with ether. The organic phase is dried (Na$_2$SO$_4$) and the solvent evaporated off. The residue is purified by flash chromatography (dichloromethane, 2.8 g; 90%).

$^1$H NMR —CHCl$_3$—δ (ppm): 0.88 (3H, m); 1.21 (6H, s); 1.33 (6H, m); 1.64 (2H, m); 2.67 (2H, m); 2.88 (2H, s); 5.73 (1H, broad s); 7.16 (1H, s); 7.19 (1H, s).

Step c: ethyl4-(6-hexyl-2,2-dimethyl-3-oxoindan-5-yloxy)butyrate

A mixture of 1.3 g (5 mmol) of 5-hexyl-6-hydroxy-2,2-dimethylindan-1-one, 40 ml of acetone and 2.5 g (7.5 mmol) of caesium carbonate is heated for 30 minutes at 56° C. 1.46 g (7.5 mmol) of ethyl4-bromobutyrate are added dropwise, and the mixture is then heated at reflux for 7 hours.

The resulting mixture is poured onto 1 N hydrochloric acid solution and extracted with ether. The organic phase is dried (Na$_2$SO$_4$) and the solvents are evaporated off: brown oil (2 g; 100%).

$^1$H NMR —CHCl$_3$—δ(ppm): 0.88 (3H, m); 1.20 (6H, s); 1.25 (3H, m); 1.32 (6H, m); 1.58 (2H, m); 2.13 (2H, m); 2.51 (2H, m); 2.64 (2H, m); 2.87 (2H, s); 4.02 (2H, m); 4.14 (2H, m); 7.09 (1H, s); 7.15 (1H, s).

Example 19

4-(6-hexyl-2,2-dimethyl-3-oxoindan-5-yloxy)butyric acid

A mixture of 60 ml of ethanol, 0.4 g (7.2 mmol) of potassium hydroxide, 1.8 g (4.8 mmol) of ethyl4-(6-hexyl-2,2-dimethyl-3-oxoindan-5-yloxy)butyrate and 20 ml of water is heated for 2 hours at the reflux point of the solvents. The solvents are evaporated off and the residue is placed in water and extracted with ether. The aqueous phase is acidified and then extracted with ether. Concentration of the solvents gives 1.46 g of product, which is purified by flash chromatography (95/5 dichloromethane/methanol): 1.18 g; m.p.: 82° C.; 71%.

$^1$H NMR —CHCl$_3$—δ (ppm): 0.88 (3H, m); 1.21 (6H, s); 1.31 (6H, m); 1.58 (2H, m); 2.15 (2H, m); 2.59 (2H, m); 2.64 (2H, m); 2.88 (2H, s); 4.04 (2H, m); 7.11 (1H, s); 7.16 (1H, s).

N.B.: acid H not observed.

Example 24

4-[6-hexyl-3-(hydroxyimino)-5-indanyloxy]butyric acid

A mixture of 50 mg (0.157 mmol) of 4-(6-hexyl-3-oxo-5-indanyloxy)butyric acid, 13 mg (0.188 mmol) of hydroxylamine hydrochloride and 32 mg (0.393 mmol) of sodium acetate in 3 ml of 85% ethanol is heated at reflux for 1 hour. After cooling, the mixture is poured into 50 ml of ice-cold water. The solid formed is isolated by filtration, washed with water and dried to give 26.3 mg (50%) of the expected product.

The compounds of Tables A and B below were prepared by following the same types of procedures as in the preceding examples.

TABLE A

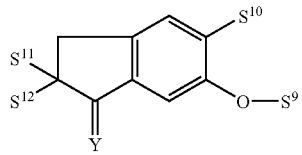

| Example m.p./° C. | Y | $S^{10}$ | $S^9$ | $S^{11}$ | $S^{12}$ | $^1$H NMR(300 MHz) |
|---|---|---|---|---|---|---|
| 1 | O | —$C_6H_{13}$ | —$(CH_2)_3$—COOH | H | H | ($CDCl_3$)=0.87(3H, m); 1.31(2H, m); 2.15(2H, m); 2.50-2.64(6H, m); 3.02(2H, m); 4.04(2H, m); 7.06-7.24(2H, 2s)-(OH not visible) |
| 2 | $CH_2$ | —$C_6H_{13}$ | —$(CH_2)_3$—COOEt | H | H | (DMSO-d6)=0.84(3H, m); 1.16(3H, m); 1.27(6H, m); 1.48(2H, m); 1.98(2H, m); 2.48(2H, m); 2.63-2.89(4H, m); 3.86-4.19(4H, m); 4.93(1H, m); 5.42(1H, s); 7.01(1H, s); 7.04(1H, s) |
| 3 | O | —$C_6H_{13}$ | —$CH_2$—C$_6$H$_4$—COOCH$_3$ (para) | H | H | ($CDCl_3$)=0.87(3H, m); 1.26-1.45(6H, m); 1.48-1.74(2H, m+2H, s); 2.55-2.85(4H, m); 3.04(2H, m); 3.92(3H, s); 5.15(2H, m); 7.18(1H, s); 7.26(1H, s); 7.51(2H, m); 8.06(2H, m). |
| 4 | O | —$C_6H_{13}$ | —$CH_2$—C$_6$H$_4$—COOCH$_3$ (meta) | H | H | ($CDCl_3$)=0.85(3H, m); 1.12-1.46(6H, m); 1.47-1.78(2H, m+2H, s); 2.55-2.84(4H, m); 3.04(2H, m); 3.92(3H, s); 5.12(2H, m); 7.19(1H, s); 7.26(1H, s); 7.39-7.71(2H, m); 7.89-8.22(2H, m). |
| 5 | O | —$C_6H_{13}$ | —$C(CH_3)_2$—COOEt | H | H | ($CDCl_3$)=0.88(3H, m); 1.15-1.44(3H, m+4H, m); 1.62(6H, s); 2.65(4H, m); 3.01(2H, m); 4.24(2H, m); 6.90(1H, s); 7.22(1H, s). |
| 6 | O | —$C_6H_{13}$ | —$(CH_2)_4$—$C(CH_3)_2$—COOEt | H | H | ($CDCl_3$)=0.88(3H, m); 1.19-1.81(3H, m+6H, s+16H, m); 2.67(4H, m); 3.02(2H, m); 4.17(2H, m); 7.17(1H, s); 7.21(1H, s). |
| 7, (194) | O | —$C_6H_{13}$ | —$CH_2$—C$_6$H$_4$—COOH (para) | H | H | ($CDCl_3$)=0.87(3H, m); 1.14-1.90(8H, m); 2.55-2.91(4H, m); 3.05(2H, m); 5.18(2H, s); 7.18(1H, s); 7.27(1H, s); 7.54(2H, m); 8.11(2H, m). |
| 8, (90) | O | —$C_6H_{13}$ | —$C(CH_3)_2$—COOH | H | H | ($CDCl_3$)=0.88(3H, m); 1.32(6H, m); 1.48-1.82(2H, m+6H, s); 2.67(4H, m); 3.03(2H, m); 7.07(1H, s); 7.24(1H, s). |
| 9, (190) | O | —$C_6H_{13}$ | —$(CH_2)_3$—COO$^-$Na$^+$ | H | H | (DMSO-d6)=0.88(3H, m); 1.31(6H, m); 1.57(2H, m); 1.99(2H, m); 2.44(2H, m); 2.64(4H, m); 3.02(2H, m); 4.06(2H, m); 7.07(1H, s), 7.37(1H, s) |
| 10 | O | —$C_6H_{13}$ | —$(CH_2)_4$—$C(CH_3)_2$—COOH | H | H | ($CDCl_3$)=0.88(3H, m); 1.09-1.91(6H, s+14H, m); 2.67(4H, m); 3.02(2H, m); 3.98(2H, m); 7.10(1H, s); 7.20(1H, s). |
| 11 | O | —$C_6H_{13}$ | —$(CH_2)_2$—$C(CH_3)_2$—COOEt | H | H | ($CDCl_3$)=0.88(3H, m); 1.11-1.46(3H, m+6H, s+6H, m); 1.47-1.72(4H, m); 2.09(2H, m); 2.66(4H, m); 3.02(2H, m); 4.11(2H, m); 7.09(1H, s); 7.20(1H, s). |

TABLE A-continued

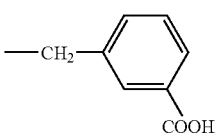

| Example m.p./°C. | Y | S¹⁰ | S⁹ | S¹¹ | S¹² | ¹H NMR(300 MHz) |
|---|---|---|---|---|---|---|
| 12, (90) | CH₂ | —C₆H₁₃ | —(CH₂)₃—COOH | H | H | (CDCl₃)=0.87(3H, m); 1.31(6H, m); 1.57(2H, m); 2.13(4H, m); 2.63(4H, m); 3.22(2H, m); 4.07(2H, m); 6.80(1H, s); 7.19(1H, s). |
| 13, (178-180) | O | —C₆H₁₃ | —CH₂—C₆H₄—COOH (meta) | H | H | (DMSO-d6)=0.80(3H, m); 1.24(6H, m); 1.57(2H, m); 2.55-2.84(4H, m); 2.98(2H, m); 5.26(2H, s); 7.10-8.17(6H, aromatic, m). |
| 14 | O | —C₆H₁₃ | —CH=CH—CH₂—COOEt | H | H | (CDCl₃)=0.88(3H, m); 1.26(3H, m); 1.32(6H, m); 1.60(2H, m); 2.70(4H, m); 3.05(2H, m); 3.28(2H, m); 4.16(2H, m); 5.10(1H, m); 6.52(1H, m); 7.15-7.37(2H, 2s). |
| 15, (98, 100) | O | —C₆H₁₃ | —CH₂—CH₂—C(CH₃)₂—COOH | H | H | (CDCl₃)=0.88(3H, m); 1.15-1.47(6H, s+4H, m); 1.61(2H, m); 2.13(4H, m); 2.67(4H, m); 3.02(2H, m); 4.06(2H, m); 7.12(1H, s); 7.20(1H, s). |
| 16 | O | —C₆H₁₃ | —CH=CH—CH₂—COOH | H | H | (CDCl₃)=0.87(3H, m); 1.15-1.48(6H, m); 1.60(2H, m); 2.58-2.81(4H, m); 3.06(2H, m); 3.34(2H, m); 5.08(1H, m); 6.55(1H, m); 7.16-7.39(2H, 2s). |
| 17 | O | —C₆H₁₃ | —CH₂—C(CH₃)₂—COOEt | H | H | (CDCl₃)=0.87(3H, m); 1.21(3H, m); 1.32(6H, s); 1.10-1.42(6H, m); 1.55(2H, m); 2.50-2.78(4H, m); 3.02(2H, m); 3.98(2H, s); 4.13(2H, m); 7.11(1H, s); 7.20(1H, s). |
| 18 | O | —C₆H₁₃ | —(CH₂)₃—COOEt | CH₃ | CH₃ | (CDCl₃)=0.88(3H, m); 1.10-1.43(3H, m+6H, s+4H, m); 1.60(2H, m); 2.16(2H, m); 2.39-2.77(4H, m); 2.64(2H, m); 2.87(2H, s); 4.02(2H, m); 4.14(2H, m); 7.09(1H, s); 7.15(1H, s). |
| 19, (90) | O | —C₆H₁₃ | —(CH₂)₃—COOH | CH₃ | CH₃ | (CDCl₃)=0.88(3H, m); 1.10-1.44(6H, s+6H, m); 1.58(2H, m); 2.62(4H, m); 2.88(2H, s); 4.04(2H, m); 7.11(1H, s); 7.16(1H, s). |
| 20 | O | —C₆H₁₃ | —CH₂—C(CH₃)₂—COOH | H | H | (CDCl₃)=0.88(3H, m); 1.28(4H, m); 1.37(6H, s); 1.54(4H, m); 2.65(4H, m); 3.03(2H, m); 4.00(2H, s); 7.12(1H, s); 7.21(1H, s). |
| 21 | O | —C₆H₁₃ | —(CH₂)₃—C(CH₃)₂—COOEt | H | H | (CDCl₃)=0.87(3H, m); 1.06-1.43(3H, m+6H, s+6H, m); 1.43-1.88(6H, m); 2.65(4H, m); 3.02(2H, m); 3.94(2H, m); 4.12(2H, m); 7.08(1H, s); 7.20(1H, s). |
| 22, (80) | O | —C₆H₁₃ | —(CH₂)₃—C(CH₃)₂—COOH | H | H | (CDCl₃)=0.88(3H, m); 1.25(6H, s); 1.31(4H, m); 1.43-1.91(8H, m); 2.67(4H, m); 3.02(2H, m); 3.97(2H, m); 7.09(1H, s); 7.20(1H, s). |
| 23 | O | —C₆H₁₃ | —(CH₂)₄—C(CH₃)(Et)—COOEt | H | H | (CDCl₃)=0.60-0.96(6H, m); 0.96-1.97(21H, m); 2.64(4H, m); 3.02(2H, m); 3.72-4.20(4H, m); 7.09(1H, s); 7.20(1H, s). |

TABLE B

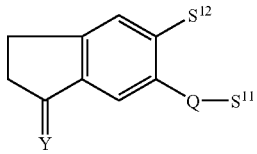

| Example | Y | Q | S¹¹ | S¹² | m.p. (° C.) | ¹H NMR(300 MHz) |
|---|---|---|---|---|---|---|
| 24 | N-OH | O | —(CH₂)₃—COOH | —C₆H₁₃ | 148 | (DMSO-d6): 0.84(3H, m); 1.27(6H, m); 1.49(2H, m); 1.94(2H, m); 2.40(2H, m); 2.53(2H, m); 2.74(2H, m); 2.86(2H, m); 3.97(2H, m); 6.96(1H, s); 7.08(1H, s); 10.64(1H, broad s); 12.11 (1H, broad s) |
| 25 | N-OH | NH | —(CH₂)₃—COOH | —CH₂-(2-methoxyphenyl) | — | (DMSO-d6): 1.78(2H, m); 2.27(2H, m); 2.70(2H, m); 2.73(2H, m); 3.06(2H, m); 3.74(2H, s); 3.79(3H, s); 4.86(1H, broad m); 6.64 (1H, s); 6.73(1H, s); 6.86 (1H, m); 7.02(2H, m); 7.21 (1H, m); 10.51(1H, broad s); 12.07(1H, broad s). |

Example 30

Step a: 3-(3-iodo-4-methoxyphenyl)propionic acid

A mixture of 3-(4-methoxyphenyl)propionic acid (18 g; 0.1 mol), ICl (30 g; 0.18 mol) and acetic acid (200 ml) is heated at +90° C. for 4 hours.

After concentration, the residue is taken up in ethyl acetate and washed with 10% $Na_2S_2O_3$ solution (200 ml), and then with 1N sodium hydroxide. The aqueous phase, separated out by settling of the phases, is acidified to pH 1 and then extracted with ethyl acetate.

After drying ($Na_2SO_4$), evaporation of the solvents gives a beige powder (27.5 g, 90%).

¹H NMR-CDCl₃—δ(ppm): 2.63 (t, 2H); 2.85 (t, 2H); 3.84 (s, 3H); 6.74 (d, 1H); 7.14 (dd, 1H); 7.62 (d, 1H).

Step b: 5-iodo-6-methoxyindan-1-one

Polyphosphoric acid (160 g; 1.63 mol) is preheated to +80° C., and 3-(3-iodo-4-methoxyphenyl)propionic acid (10 g, 32.6 mmol) is then added in four portions. The reaction mass is stirred for 40 minutes at +80° C. A mixture (600 g) of ice+water is then added and the resulting mixture is extracted three times with ethyl acetate. The combined organic phases are successively washed with water, with 1N sodium hydroxide and with brine, and then dried ($Na_2SO_4$). Trituration of the evaporation residue (7.0 g) in a mixture of Et₂O/pentane (30 ml/15 ml) gives a brown powder (3.6 g).

The protocol is repeated twice for amounts of 5 g and 11.7 g of 3-(3-iodo-4-methoxyphenyl)propionic acid to give, respectively, 1.2 g and 3.7 g of the expected product.

A second trituration of the total (8.5 g) in a mixture of ether/pentane (15 ml/4 ml) gives the pure expected product (7.7 g). The corresponding mother liquors are concentrated and purified by chromatography. Trituration in ether gives a second crop (1.1 g).

m.p.=140° C.

¹H NMR-CDCl₃—δ(ppm): 2.65-2.72 (m, 2H); 3.01-3.09 (m, 2H); 3.0 (s, 3H); 7.09 (s, 1H); 7.96 (s, 1H).

Step c: 6-hydroxy-5-iodoindan-1-one

AlCl₃ (10.66 g; 80.0 mmol) is added to a mixture of 5-iodo-6-methoxyindan-1-one (7.68 g; 26.66 mol) in toluene (130 ml).

After heating for 15 minutes at +80° C., the crude product is cooled and poured into ice-cold water. The precipitate obtained is filtered off by suction, washed with water and dried (6.36 g, 87% yield).

m.p.=260° C.

¹H NMR-DMSOd⁶—δ(ppm): 2.53-2.60 (m, 2H); 2.91-2.98 (m, 2H); 6.99 (s, 1H); 7.96 (s, 1H); 10.65 (s, OH).

Step d: ethyl 4-(6-iodo-3-oxoindan-5-yloxy)butanoate

A mixture of 6-hydroxy-5-iodoindan-1-one (6.36 g, 23.2 mmol), caesium carbonate (15.12 g, 46.4 mmol) and ethyl4-bromobutyrate (9.05 g, 46.4 mmol) in acetone (60 ml) is heated at reflux pendant 1 hour 15 minutes.

The reaction mass is poured into ice-cold 0.5N hydrochloric acid. After extraction (EtOAc), washing with water and then drying ($Na_2SO_4$), chromatography on silica of the evaporation residue gives 5.28 g of the expected product (59% yield).

¹H NMR-DMSOd⁶—δ(ppm): 1.17 (t, 3H); 1.99 (m, 2H); 2.52 (t, 2H); 2.57-2.65 (m, 2H); 2.95-3.03 (m, 2H); 4.06 (q, 2H); 4.10 (t, 2H); 7.04 (s, 1H); 8.07 (s, 1H).

Step e: 4-[6-(cyclohexylmethyl)-3-oxoindan-5-yloxy]butyric acid

A 0.5N solution of (cyclohexylmethyl)zinc bromide (1.42 ml, 0.708 mmol) in THF is added to a mixture of ethyl4-(6-iodo-3-oxoindan-5-yloxy)butanoate (250 mg, 0.644 mmol)

and dichlorobis(triphenylphosphine)palladium II (23 mg) in DMF (3 ml) at room temperature.

The mixture is stirred under nitrogen for 1 hour at room temperature and then poured into ice-cold water. After extraction with ether, washing with water and drying (Na$_2$SO$_4$), the evaporation residue (290 mg) is purified by chromatography on silica (80/20 heptane/EtOAc).

138 mg of the expected product are obtained (yield: 60%).

(2H, m); 2.58 (2H, m); 2.97 (2H, m); 4.01 (2H, m); 7.02 (1H, s); 7.27 (1H, s); 12.12 (1H, s).

The compounds of Table C below are prepared from the product obtained from step d) of the preparation of Example 30, or from the product obtained from step f) of the preparation of Example 66 illustrated below, following a procedure identical to that of Example 30.

TABLE C

Structure: indan-1-one with L substituent and O—(CH$_2$)$_3$—COOH group

| Example | L | m.p. (° C.) | $^1$H NMR(300 MHz) |
|---|---|---|---|
| 26 | —(CH$_2$)$_2$—C$_6$H$_5$ | — | (CDCl$_3$): 1.98-2.31(2H, m); 2.44-2.78(4H, m); 2.80-3.18(6H, m); 3.96-4.22(2H, m); 6.87-7.75(7H, m) |
| 27 | —(CH$_2$)$_2$—CH(CH$_3$)$_2$ | 84 | (DMSO-d6): 0.91(6H, d, J=6.41Hz); 1.34-1.47(2H, m); 1.56(1H, sept., J=6.41Hz); 1.96(2H, m); 2.29-2.45(2H, m); 2.54-2.69(4H, m); 2.87-3.06(2H, m); 4.02(2H, m); 7.02(1H, s); 7.33(1H, s); 12.12(1H, s). |
| 28 | —CH$_2$—(2-methoxyphenyl) | 130 | (DMSO-d6); 1.92(2H, m); 2.23(2H, m); 2.57(2H, m); 2.92(2H, m); 3.76(3H, s); 3.92(2H, s); 4.02(2H, m); 6.61-7.40(6H, m); 12.10(1H, s) |
| 29 | —CH$_2$—(4-fluorophenyl) | 130 | (DMSO-d6); 1.92(2H, m); 2.31(2H, m); 2.58(2H, m); 2.96(2H, m); 3.86-4.08(2H, s+2H, m); 6.80-7.56(6H, m); 12.11(1H, s) |
| 30 | —CH$_2$—cyclohexyl | 130 | (DMSO-d6); 0.77-1.24(5H, m); 1.37-1.73(6H, m); 1.95(2H, m); 2.40(2H, m); 2.52(2H, m); 2.58(2H, m); 2.97(2H, m); 4.01(2H, m); 7.02(1H, s); 7.27(1H, s); 12.12(1H, s). |
| 31 | —(CH$_2$)$_4$—C(CH$_3$)$_2$—CN | 100 | (DMSO-d6): 1.27(6H, s); 1.35-1.68(6H, m); 1.97(2H, m); 2.41(2H, m); 2.53-2.76(4H, m); 2.97(2H, m); 4.02(2H, m); 7.03(1H, s); 7.35(1H, s); 12.13(1H, s) |
| 32 | —(CH$_2$)$_4$—CN | 150 | (DMSO-d6): 1.46-1.75(4H, m); 1.97(2H, m); 2.40(2H, m); 2.51(2H, m); 2.54-2.78(4H, m); 2.98(2H, m); 4.02(2H, m); 7.04(1H, s); 7.35(1H, s); 12.12(1H, s) |
| 33 | —CH$_2$—CH$_2$—C≡CEt | 120 | (DMSO-d6): 1.00(3H, m); 1.85-2.17(4H, m); 2.40(4H, m); 2.60(2H, m); 2.78(2H, m); 2.97(2H, m); 4.03(2H, m); 7.04(1H, s); 7.38(1H, s); 12.14(1H, broad s). |
| 34 | —CH$_2$—CH$_2$—C≡C—CH$_3$ | 135 | (DMSO-d6): 1.70(3H, s); 1.96(2H, m); 2.40(4H, m); 2.60(2H, m); 2.78(2H, m); 2.98(2H, m); 4.03(2H, m); 7.04(1H, s); 7.37(1H, s); 12.15(1H, broad s). |

The above product is taken up in methanol (2.5 ml) and treated with 1N sodium hydroxide (0.77 ml) for 3 hours 30 minutes at room temperature. The reaction medium is diluted with water and then extracted with ethyl acetate. The aqueous phase is acidified to pH 1 by addition of 1N hydrochloric acid, and then extracted with ethyl ether. This ether phase is concentrated and the residue is then dispersed in a 50/50 mixture of heptane/diisopropyl ether (yield: 71%).

m.p.=130° C. $^1$H NMR-DMSO d$^6$—δ(ppm): 0.77-1.24 (5H, m); 1.37-1.73 (6H, m); 1.95 (2H, m) 2.40 (2H, m); 2.52

Example 37

Step a: 5-bromo-6-nitroindan-1-one

Fuming nitric acid (166 ml) is cooled to −15° C., and 5-bromoindan-1-one (25 g, 0.118 mol) is then added portionwise. After stirring for 4 hours 30 minutes at between −10° C. and −15° C., the reaction mass is poured into ice-cold water (1600 ml).

The precipitate is filtered off by suction, washed with water and taken up in dichloromethane to be dried over Na$_2$SO$_4$.

The evaporation residue (25.8 g) is purified by crystallisation from ethanol (15.3 g, yield: 51%). m.p.=130° C.

$^1$H NMR-CDCl$_3$—δ(ppm): 2.75-2.82 (m, 2H); 3.18-3.25 (m, 2H); 7.89 (s, 1H); 8.10 (s, 1H).

Step b: 5-hex-1-ynyl-6-nitroindan-1-one

1-Hexyne (7.3 g, 89.5 mmol) is added to a mixture, under nitrogen and at room temperature, of 5-bromo-6-nitroindan-1-one (15.3 g, 59.7 mmol), dichlorobis(triphenylphosphine) palladium II (0.83 g, 1.19 mmol), CuI (1.14 g, 5.97 mmol) and triethylamine (14.8 ml) in THF (72 ml), at a rate such that the temperature of the reaction mixture does not exceed 40° C. After stirring for 1 hour between 35 and 40° C., catalyst (0.83 g) and CuI (1.14 g) are added, and the mixture is stirred for a further 1 hour 30 minutes between 35° C. and 40° C. The mixture is poured onto ether, the insoluble matter is filtered off, the filtrate is concentrated and the evaporation residue is purified by chromatography on alumina (8.2 g, yield: 53%).

$^1$H NMR-CDCl$_3$—δ(ppm): 0.93 (t, 3H); 1.39-1.70 (m, 4H); 2.44-2.52 (m, 2H); 2.72-2.80 (m, 2H); 3.13-3.21 (m, 2H); 7.64 (s, 1H); 8.24 (s, 1H).

Step c: 6-amino-5-hex-1-ynylindan-1-one

A mixture of 5-hex-1-ynyl-6-nitroindan-1-one (8.2 g, 31.8 mmol), NH$_4$Cl (0.84 g) and Fe (8.88 g, 0.159 mol) in ethanol (97 ml) and water (32 ml) is heated at reflux for 45 minutes. After concentrating to dryness, the residue is taken up in ether and the insoluble matter is filtered off. The filtrate is washed with water, dried (Na$_2$SO$_4$) and concentrated. Dispersion in heptane gives a solid (6.2 g, yield: 86%).

$^1$H NMR-CDCl$_3$—δ(ppm): 0.95 (t, 3H); 1.41-1.68 (m, 4H); 2.50 (t, 2H); 2.59-2.67 (m, 2H); 2.92-3.00 (m, 2H); 4.25 (broad s, 2H); 6.99 (s, 1H); 7.33 (s, 1H).

Step d: 2,2,2-trifluoro-N-(6-hex-1-ynyl-3-oxoindan-5-yl)acetamide

Trifluoroacetic anhydride (6.88 g, 32.7 mmol) is added dropwise to a mixture of 6-amino-5-hex-1-ynylindan-1-one (6.2 g, 27.3 mmol) in trifluoroacetic acid (37 ml), cooled to between 0° C. and 5° C. The reaction mass is stirred for 1 hour 30 minutes at between 0 and 5° C., and then poured onto ice-cold water. The precipitate is filtered off by suction, washed with water and then dissolved in ether for drying (Na$_2$SO$_4$). Dispersion in heptane of the evaporation residue gives a solid (6.74 g, yield: 76%).

$^1$H NMR-CDCl$_3$—δ(ppm): 0.96 (t, 3H); 1.40-1.71 (m, 4H); 2.55 (t, 2H); 2.67-2.76 (m, 2H); 3.04-3.13 (m, 2H); 7.53 (s, 1H); 8.64 (s, 1H), 8.82 (broad s, NH).

Step e: (6-hex-1-ynyl-3-oxoindan-5-ylamino)acetic acid

A mixture of 2,2,2-trifluoro-N-(6-hex-1-ynyl-3-oxoindan-5yl)acetamide (2.8 g; 8.66 mol), methyl bromoacetate (5.3 g; 34.64 mmol), K$_2$CO$_3$ (4.7 g, 34.64 mmol) and KI (1.44 g, 8.66 mmol) in acetone (84 ml) is heated at reflux for 3 hours. After concentrating to dryness, the residue is taken up in ethyl ether and the insoluble matter is filtered off. The filtrate, once concentrated to dryness, is purified by chromatography on silica. A light brown oil is obtained, which crystallises at room temperature (2.5 g, yield: 73%).

m.p.=80° C. $^1$H NMR-CDCl$_3$—δ(ppm): 0.93 (t, 3H); 1.34-1.65 (m, 4H); 2.43 (t, 2H); 2.69-2.77 (m, 2H); 3.09-3.17 (m, 2H); 3.75 (s, 3H); 3.80 (d, 1H); 5.00 (d, 1H); 7.58 (s, 1H); 7.87 (s, 1H).

A solution of the above solid (2.5 g, 6.32 mmol) in methanol (92 ml) is treated overnight with an aqueous solution (46 ml) of NaOH (0.76 g, 18.96 mmol) at room temperature. The medium is concentrated to dryness and the residue is taken up in water.

After acidification to pH 4.4 (pH-meter) with dilute HCl, the precipitate formed is filtered off and then dissolved in dichloromethane. This organic phase is dried over Na$_2$SO$_4$ and then concentrated to dryness. The solid obtained is dispersed in diisopropyl ether (1.65 g, 92%).

$^1$H NMR-DMSO d$^6$—δ(ppm): 0.91 (t, 3H); 1.37-1.64 (m, 4H); 2.51-2.60 (m, 4H); 2.85-2.95 (m, 2H); 3.92 (s, 2H); 5.66 (broad s, NH); 6.54 (s, 1H); 7.37 (s, 1H).

Example 36

(6-Hexyl-3-oxoindan-5-ylamino)acetic acid

A solution in ethanol (50 ml) of the derivative from Example 48 (0.26 g, 0.91 mmol) is treated with H$_2$ (3 bar) in the presence of 10% Pd/C (26 mg). After filtering off the catalyst and evaporation of the solvent, the solid obtained is crystallised from diisopropyl ether (0.15 g, yield: 57%).

m.p.=144° C. $^1$H NMR-CDCl$_3$—δ(ppm): 0.89 (t, 3H); 1.23-1.47 (m, 6H); 1.58-1.72 (m, 2H); 2.58 (t, 2H); 2.62-2.70 (m, 2H); 2.96-3.05 (m, 2H); 4.04 (s, 2H); 5.99 (broad s, NH); 6.82 (s, 1H); 7.18 (s, 1H).

Example 39

[(6-Hex-1-ynyl-3-oxoindan-5-yl)methylamino]acetic acid

A mixture of the derivative from Example 48 (1.37 g, 4.8 mmol), K$_2$CO$_3$ (2.61 g, 19.2 mmol) and CH$_3$I (10.9 g, 76.8 mmol) in acetone (45 ml) is heated at reflux for 5 hours. CH$_3$I (10.9 g) is added and the mixture is stirred overnight at 50° C. CH$_3$I (10.9 g) is added and the mixture is heated at reflux for a further 4 hours 30 minutes. CH$_3$I (10.9 g), K$_2$CO$_3$ (1.3 g) and DMF (10 ml) are added, and the mixture is stirred for a further 3 days at room temperature. The reaction medium is then concentrated to dryness, the residue is taken up in ethyl ether and the insoluble matter is filtered off. The filtrate is concentrated to dryness and purified by chromatography on silica. A light brown oil is obtained (0.94 g, yield: 62%).

A solution of the oil obtained above (0.94 g, 3 mmol) in methanol (43 ml) is treated overnight with an aqueous solution (21 ml) of NaOH (0.36 g, 9 mmol). The medium is concentrated to dryness and the residue is taken up in water. After acidification to pH 4.4 (pH-meter) with dilute HCl, the medium is extracted with ether. The ether phase is dried over Na$_2$SO$_4$, filtered and concentrated.

The evaporation residue is dispersed in diisopropyl ether (0.5 g, 55%).

m.p.=160° C. $^1$H NMR-CDCl$_3$—δ(ppm): 0.93 (3H, m); 1.32-1.71 (4H, m); 2.46 (2H, m); 2.69 (2H, m); 2.91 (3H, s); 3.03 (2H, m); 3.99 (2H, s); 7.37 (1H, s); 7.49 (1H, s).

Example 40

[(6-Hexyl-3-oxoindan-5yl)methylamino]acetic acid

A solution in ethanol (50 ml) of the derivative from Example 50 (0.27 g, 0.91 mmol) is treated with H$_2$ (3 bar) in the presence of 10% Pd/C (27 mg). After filtering off the catalyst and evaporation of the solvent, the solid obtained is taken up several times in boiling pentane. Evaporation of the pentane gives the expected product as a light yellow solid (80 mg, yield: 30%).

m.p.=70° C. $^1$H NMR-CDCl$_3$—δ(ppm): 0.88 (3H, m); 1.31 (6H, m); 1.64 (2H, m); 2.54-2.87 (4H, m+3H, s); 3.06 (2H, m); 3.70 (2H, s); 7.32 (1H, s); 7.53 (1H, s).

The derivatives of Table D below are prepared according to the procedures for the preparation of the derivatives of Examples 38, 39, 41 and 42:

$^1$H NMR-CDCl$_3$—δ(ppm): 0.88 (t, 3H); 1.23-1.45 (m, 6H); 1.57-1.72 (m, 2H); 2.71-2.80 (m, 4H); 3.10-3.18 (m, 2H); 7.43 (s, 1H); 7.59 (s, 1H).

Step b: 5-hexyl-6-mercaptoindan-1-one

A suspension of NaH (60% in petroleum jelly, 0.72 g, 18.0 mmol) in THF (28 ml) is cooled to 0° C. and a solution of triisopropylsilanethiol (3.42 g, 18.0 mmol) in THF (28 ml) is

TABLE D

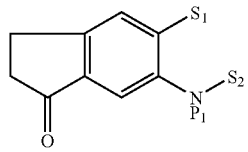

| Example | S$^1$ | P$_1$ | S$^2$ | m.p. (° C.) | $^1$H NMR(300 MHz) |
|---|---|---|---|---|---|
| 35 | —C≡C—(CH$_2$)$_3$—CH$_3$ | H | —(CH$_2$)$_3$—COOH | — | (CDCl$_3$): 0.91(3H, m); 1.32-1.67(4H, m) 1.88(2H, m); 2.21-2.50(2H, m); 2.74(2H, m); 3.14(2H, m); 3.38(1H, m); 4.19(1H, m); 7.37-7.76(2H.2s). |
| 36 | —C$_6$H$_{13}$ | H | —(CH$_2$)$_3$—COOH | 110 | (CDCl$_3$): 0.88(3H.m); 1.15-1.48(6H, m); 1.61(2H, m); 2.00(2H, m); 2.33-2.58(4H, m); 2.65(2H, m); 2.99(2H, m); 3.25(2H, m); 5.42(2H, broad s); 6.90(1H, s); 7.13(1H, s) |
| 37 | —C≡C—C$_4$H$_9$ | H | —CH$_2$—COOH | 80 | (CDCl$_3$): 0.96(3H, m); 1.33-1.75(4H, m); 2.52(2H, m); 2.67(2H, m); 2.98(2H, m); 4.04(2H, s); 4.27(2H, broad s); 6.76(1H, s); 7.37(1H, s). |
| 38 | —C$_6$H$_{13}$ | H | —CH$_2$—COOH | 144 | (CDCl$_3$): 0.89(3H, m); 1.11-1.51(6H, m); 1.66(2H, m); 2.43-2.79(4H, m); 3.00(2H, m); 4.04(2H, s); 5.98(2H, broad s); 6.82(1H, s); 7.18(1H, s) |
| 39 | —C≡C—C$_4$H$_9$ | CH$_3$ | —CH$_2$—COOH | 160 | (CDCl$_3$): 0.93(3H, m); 1.32-1.71(4H, m); 2.46(2H, m); 2.69(2H, m); 2.91(3H, s); 3.03(2H, m); 3.99(2H, s); 7.37(1H, s); 7.49(1H, s) |
| 40 | —C$_6$H$_{13}$ | CH$_3$ | —CH$_2$—COOH | 70 | (CDCl$_3$): 0.88(3H, m); 1.31(6H, m); 1.64(2H, m); 2.54-2.87(4H, m+3H, s); 3.06(2H, m); 3.70(2H, s); 7.32(1H, s); 7.53(1H.s). |
| 41 | —C$_6$H$_{13}$ | —CH$_3$ | —(CH$_2$)$_3$—COOH | — | (CDCl$_3$): 0.88(3H, m); 1.11-1.46(6H, m); 1.61(2H, m); 1.82(2H, m); 2.39(2H, m); 2.51-2.79(3H, s+4H, m); 2.92(2H, m); 3.05(2H, m); 7.30(1H, s); 7.48(1H, s). |

Example 42

Step a: 6-hexyl-3-oxoindan-5-yl 1,1,1-trifluoromethanesulfonate

A mixture of 5-hexyl-6-hydroxyindan-1-one (4.5 g, 19.4 mmol) in pyridine (10 ml) is cooled to 10° C., and trifluoromethanesulfonic anhydride (6.01 g, 21.3 mmol) is then slowly added. After stirring for 1 hour at room temperature, the crude reaction product is poured into a mixture of 32% HCl (15 ml) and ice. After extraction with ether, the organic phase obtained is washed with water, dried (Na$_2$SO$_4$) and concentrated. The evaporation residue (7.08 g) is purified by flash chromatography (10/90 ethyl acetate/heptane). 6.57 g of the expected product are obtained (yield: 93%).

then added. After stirring for 30 minutes at 0° C., tetrakis(triphenylphosphine)palladium (1.6 g) is added, followed by addition of a solution of the above triflate (6.54 g, 18.0 mmol) in benzene (57 ml). The reaction mixture is then heated at reflux for 2 hours 30 minutes. It is cooled, poured onto ice and extracted with ether. The organic phase is washed with water and dried (Na$_2$SO$_4$). The crude product (10.0 g) from evaporation is purified by flash chromatography on silica (5/95 ethyl acetate/heptane) to give 5.17 g of the expected silyl product (yield: 71%).

$^1$H NMR-CDCl$_3$—δ(ppm): 0.88 (t, 3H); 1.05 (d, 18H); 1.19-1.45 (m, 9H); 1.56-1.69 (m, 2H); 2.62-2.69 (m, 2H); 2.91-2.99 (m, 2H); 3.01-3.08 (m, 2H); 7.27 (s, 1H); 7.79 (s, 1H).

A solution of the above silyl derivative (5.17 g, 12.8 mmol) in THF (25 ml) is cooled to 0° C. and 1M tetrabutylammonium fluoride solution (18 ml, 18 mmol) is then added. After stirring for 5 minutes at 0° C., the crude reaction product is poured into a mixture of 11% hydrochloric acid and ice, and extracted with ether. The organic phase is washed with water and then dried (Na$_2$SO$_4$). The evaporation residue (6.3 g) is dispersed in heptane and then filtered off by suction. 1.9 g of the expected product are obtained (yield: 60%).

m.p.=100° C. $^1$H NMR-CDCl$_3$—δ(ppm): 0.89 (t, 3H); 1.26-1.46 (m, 6H); 1.56-1.69 (m, 2H); 2.62-2.74 (m, 4H); 3.02-3.08 (m, 2H); 3.39 (s, 5H); 7.25 (s, 1H); 7.64 (s, 1H).

Step c: ethyl4-(6-hexyl-3-oxoindan-5-ylsulfanyl)butyrate

A mixture of the above thiol (0.3 g, 1.2 mmol), Cs$_2$CO$_3$ (0.41 g, 1.26 mmol), and ethyl4-bromobutyrate (0.259 g, 1.33 mmol) in acetone (4 ml) is heated at 55° C. for 2 hours. The crude reaction product is diluted with ether, washed with water and dried (Na$_2$SO$_4$). The evaporation residue is purified by flash chromatography on silica (95/5 heptane/ethyl acetate). 0.37 g of the expected product is obtained (yield: 85%).

$^1$H NMR-CDCl$_3$—δ(ppm): 0.88 (m, 3H); 1.24 (t, 3H); 1.25-1.45 (m, 6H); 1.61 (m, 2H); 1.97 (m, 2H); 2.46 (t, 2H); 2.66 (m, 2H); 2.75 (m, 2H); 2.99 (t, 2H); 3.06 (m, 2H); 4.13 (q, 2H); 7.26 (s, 1H); 7.60 (s, 1H).

Step d: 4-(6-hexyl-3-oxoindan-5-ylsulfanyl)butyric acid

A mixture of the product from step c (50 mg, 0.137 mmol), KOH (12 mg, 0.214 mmol), water (0.5 ml) and methanol (1 ml) is stirred overnight at room temperature. The crude reaction product is diluted with water and then acidified with 1N HCl. The precipitate is filtered off by suction and dried under vacuum (P$_2$O$_5$). 35 mg of the expected product are obtained (yield: 76%).

$^1$H NMR-CDCl$_3$—δ(ppm): 0.88 (3H, m); 1.19-1.47 (6H, m); 1.61 (2H, m); 1.98 (2H, m); 2.53 (2H, m); 2.68 (2H, m); 2.76 (2H, m); 2.91-3.15 (4H, m); 7.25 (1H, s); 7.61 (1H, s).

Example 43

4-(6-Hexyl-3-oxoindan-5-sulfonyl)butyric acid

A solution of the product from Example 51 (0.1 g, 0.276 mmol) in dichloromethane (1 ml) is cooled to 0° C. and m-chloroperbenzoic acid (0.149 g, 70% pure, 0.60 mmol) is then added. The reaction mixture is stirred for 30 minutes at 0° C. and then for 2 hours 30 minutes at room temperature. The insoluble matter is filtered off. The filtrate is washed with aqueous sodium bicarbonate solution and then with water, and dried (Na$_2$SO$_4$). 0.104 g (yield: 95%) of the sulfonyl product is obtained in the form of an oil.

$^1$H NMR-CDCl$_3$—δ(ppm): 0.88 (m, 3H); 1.22 (t, 3H); 1.27-1.38 (m, 4H); 1.44 (m, 2H); 1.70 (m, 2H); 1.99 (m, 2H); 2.44 (t, 2H); 2.74 (m, 2H); 3.05 (m, 2H); 3.15-3.27 (m, 4H); 4.09 (q, 2H); 7.49 (s, 1H); 8.39 (s, 1H).

The above sulfone is treated for 18 hours with a mixture consisting of KOH (20 mg, 0.356 mmol), methanol (2 ml) and water (1 ml). After dilution with water, the medium is extracted with ethyl ether. The aqueous phase is acidified to pH 1 and then extracted with ethyl ether. After drying (Na$_2$SO$_4$), the evaporation residue is chromatographed on silica (1/1 heptane/ethyl acetate). The oil obtained (32 mg) is dispersed in pentane. The desired product is obtained in the form of a solid (21 mg, yield: 24%).

m.p.=100° C. $^1$H NMR-DMSO-d$^6$—δ(ppm): 0.86 (3H, m); 1.19-1.47 (6H, m); 1.52-1.80 (4H, m); 2.33 (2H, m); 2.69 (2H, m); 3.01 (2H, m); 3.17 (2H, m); 3.37 (2H, m); 7.75 (1H, s); 8.03 (1H, s); 12.18 (1H, broad s).

The derivatives of Table E below are prepared using the same procedures as those employed for the preparation of the derivative of Example 42 starting with the product of step c:

TABLE E

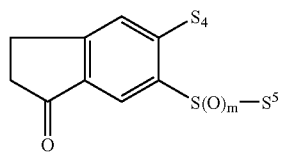

| Example | m | S$^4$ | S$^5$ | m.p. (° C.) | NMR |
|---|---|---|---|---|---|
| 42 | 0 | —C$_6$H$_{13}$ | —(CH$_2$)$_3$—COOH | 100 | (CDCl$_3$): 0.88(3H, m); 1.19-1.47(6H, m); 1.61(2H, m); 1.98(2H, m); 2.53(2H, m); 2.68(2H, m); 2.76(2H, m); 2.91-3.15(4H, m); 7.25(1H, s); 7.61(1H, s) |
| 43 | 2 | —C$_6$H$_{13}$ | —(CH$_2$)$_3$—COOH | 100 | (DMSO-d6): 0.86(3H, m); 1.19-1.47(6H, m); 1.52-1.80(4H, m); 2.33(2H, m); 2.69(2H, m); 3.01(2H, m); 3.17(2H, m); 3.37(2H, m); 7.75(1H, s); 8.03(1H, s); 12.18(1H, broad s). |
| 44 | 0 | —C$_6$H$_{13}$ | —CH$_2$—COOH | 110 | (DMSO-d6): 0.86(3H, m); 1.18-1.44(6H, m); 1.57(2H, m); 2.69(2H, m); 2.73(2H, m) 3.01(2H, m); 3.84(2H, s); 7.41(1H, s); 7.50(1H, s); 12.80(1H, broad s). |

TABLE E-continued

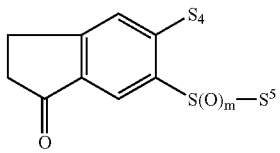

| Example | m | S⁴ | S⁵ | m.p. (°C.) | NMR |
|---|---|---|---|---|---|
| 45 | 0 | —$C_6H_{13}$ | —$CH_2$—[phenyl-COOH (meta)] | 150 | (DMSO-d6): 0.83(3H, m); 1.15-1.37(6H, m); 2.53-2.76(2H, m); 2.58(2H, m); 2.66(2H, m); 3.00(2H, m); 4.33(2H, s); 7.32-7.46(2H, m); 7.49-7.60(2H, m); 7.77(1H, m); 7.92(1H, m); 12.95(1H, broad s). |
| 46 | 0 | —$C_6H_{13}$ | —$CH_2$—[phenyl-COOH (para)] | 135 | (DMSO-d6): 0.84(3H, m) 1.11-1.36(6H, m); 1.47(2H, m); 2.58(2H, m); 2.65(2H, m); 3.00(2H, m); 4.33(2H, s); 7.33-7.48(3H, m); 7.55(1H, s); 7.84(2H, m); 12.89(1H, broad s). |
| 47 | 0 | —$C_6H_{13}$ | —$(CH_2)_4$—C(CH$_3$)(CH$_3$)—COOH | 70 | (DMSO-d6): 0.86(3H, m); 1.05(6H, s); 1.16-1.66(14H, m); 2.68(2H, m); 2.70(2H, m); 2.97(4H, m); 7.39(1H, s); 7.45(1H, s); 12.03(1H, broad s). |

Example 48

Step a: 3-hex-1-ynyl-4-methoxybenzaldehyde

A mixture of 3-iodo-4-methoxybenzaldehyde (5.2 g, 20 mmol), tetrakis(triphenylphosphine)palladium (0.29 g), CuI (0.38 g, 2 mmol) and triethylamine (5 ml) in THF (25 ml) is cooled to +10° C., and 1-hexyne (3.5 ml, 30.5 mmol) is then added. The cooling bath is removed, and the temperature of the reaction mixture rises slowly to +30° C. before decreasing slowly. 3 hours after the end of the addition, the crude reaction product is concentrated to dryness, and the residue obtained is purified by flash chromatography on silica (15/85 ethyl acetate/heptane). 4.1 g (yield: 95%) of the expected product are obtained.

$^1$H NMR-CDCl$_3$—δ(ppm): 0.94 (t, 3H); 1.41-1.67 (m, 4H); 2.47 (t, 2H); 3.94 (s, 3H); 6.96 (d, 1H); 7.77 (dd, 1H); 7.89 (d, 1H); 9.83 (s, 1H).

Step b: 4-(3-hex-1-ynyl-4-methoxyphenyl)but-3-enoic acid

A mixture of the product of step a (6.6 g, 30.46 mmol), carboxyethyltriphenylphosphonium bromide (15.2 g, 36.6 mmol), THF (30 ml) and DMSO (50 ml) is cooled to +5° C., and NaH (60% in petroleum jelly, 2.92 g, 73.0 mmol) is then added in two portions. The reaction mixture is stirred overnight at room temperature, cooled to +5° C. and then hydrolysed by addition of 200 ml of water. The aqueous phase is basified by addition of 1N sodium hydroxide, extracted with ether, acidified to pH 1 by addition of 35% hydrochloric acid, and then extracted with ether. The resulting ether phase is washed with water, dried (Na$_2$SO$_4$) and concentrated. Flash chromatography on silica (50/50 ethyl acetate/heptane) of the obtained residue gives the expected product (5.15 g, yield: 62%).

m.p.=102° C. $^1$H NMR-CDCl$_3$—δ(ppm): 0.94 (t, 3H); 1.41-1.67 (m, 4H); 2.46 (t, 2H); 3.26 (d, 2H); 3.86 (s, 3H); 6.14 (dt, 1H); 6.40 (d, 1H); 6.78 (d, 1H); 7.22 (dd, 1H); 7.41 (d, 1H).

Step c: 6-hexyl-7-methoxy-3,4-dihydro-2H-naphthalen-1-one

A mixture of the product from step b (4.5 g, 16.52 mmol) and 10% Pd/C (0.45 g) in ethanol (120 ml) is treated with H$_2$ (3 bar). After filtration on Hyflow, the filtrate is concentrated to dryness (4.58 g).

$^1$H NMR-CDCl$_3$—δ(ppm): 0.88 (t, 3H); 1.23-1.42 (m, 6H); 1.48-1.62 (m, 2H); 1.86-1.99 (m, 2H); 2.36 (t, 2H); 2.56 (t, 2H); 2.59 (t, 2H); 3.79 (s, 3H); 6.75 (d, 1H); 6.94 (s, 1H); 6.95 (d, 1H).

The above oil is taken up in methanesulfonic acid (60 ml) and stirred overnight at room temperature. After hydrolysis with ice-cold water (120 ml), the aqueous phase is extracted with dichloromethane. The organic phase is washed with water, dried (Na$_2$SO$_4$) and concentrated (4.3 g).

$^1$H NMR-CDCl$_3$—δ(ppm): 0.87 (t, 3H); 1.21-1.39 (m, 6H); 1.49-1.62 (m, 2H); 2.04-2.15 (m, 2H); 2.56-2.64 (m, 4H); 2.86 (t, 2H); 3.84 (s, 3H); 6.99 (s, 1H); 7.44 (s, 1H).

Step d: 6-hexyl-7-hydroxy-3,4-dihydro-2H-naphthalen-1-one

A mixture of the product obtained in step c (4.3 g, 16.45 mmol) and AlCl$_3$ (5.48 g, 41.1 mmol) in toluene (86 ml) is heated at reflux for 30 minutes. The mixture is cooled to +5° C. and then hydrolysed with ice-cold water (200 ml). The aqueous phase, separated out by settling of the phases, is extracted twice with ethyl ether. The combined organic phases are washed with water, dried (Na$_2$SO$_4$) and then concentrated. The solid residue obtained (4.22 g) is recrystallised from cyclohexane. 3.95 g of the expected product are obtained.

m.p.=125° C. ¹H NMR-CDCl₃—δ(ppm): 0.86 (t, 3H); 1.22-1.44 (m, 6H); 1.56-1.69 (m, 2H); 2.04-2.15 (m, 2H); 2.63 (t, 2H); 2.65 (t, 2H); 2.85 (t, 2H); 6.99 (s, 1H); 7.74 (s, 1H).

Step e: 4-(3-hexyl-8-oxo-5,6,7,8-tetrahydronaphtalen-2-yloxy)butyric acid

A mixture of the product from step d (100 mg, 0.406 mmol), K₂CO₃ (120 mg, 0.88 mmol), KI (cat.) and methyl4-chlorobutyrate (140 mg, 1.02 mmol) in acetone (2 ml) is heated at reflux for 8 hours. 1N sodium hydroxide (2 ml) is then added, and the mixture is heated at 60° C. for 2 hours. The reaction mixture is poured into water, acidified to pH 1 and then extracted with ethyl ether. The organic phase is washed with water and concentrated. Recrystallisation from cyclohexane of the residue obtained gives the expected product (40 mg).

m.p.=81° C. ¹H NMR—CDCl₃—δ(ppm): 0.87 (3H, m); 1.12-1.43 (6H, m); 1.53 (2H, m); 2.09 (2H, m); 2.37-2.68 (4H, m); 2.85 (2H, m); 3.23 (2H, m); 3.59 (2H, m); 4.03 (2H, m); 6.99 (1H, s); 7.40 (1H, s).

The derivatives of Table F below are prepared according to the preparation procedure of Example 48:

A solution of the above amine (9.3 g, 41.1 mmol) in trifluoroacetic acid (62 ml) is cooled to −5° C., and trifluoroacetic anhydride (10.35 g, 49.3 mmol) is then added dropwise. The reaction mixture is stirred for 1 hour 30 minutes at between −5 and 0° C. and then for 1 hour at room temperature, and is then poured into ice-cold water (800 ml). The precipitate is filtered off by suction, washed with water and taken up in dichloromethane for drying (Na₂SO₄). After concentration, 9 g (yield: 68%) of the expected product are obtained.

¹H NMR-CDCl₃—δ(ppm): 2.74 (m, 2H); 3.14 (m, 2H); 7.79 (s, 1H); 8.57 (s, 1H).

Step b: 4-[6-(4-fluorobenzyl)-3-oxoindan-5-ylamino]butyric acid

4-Fluorobenzylzinc chloride, as a 0.5 M solution in THF (7.5 ml, 3.75 mmol) is added dropwise to a mixture of the product from step a (0.365 g, 1.13 mmol) and dichlorobis(triphenylphosphine)palladium II (40 mg) in DMF (5 ml). After stirring for 15 hours at room temperature, the reaction mixture is poured into ice-cold water (100 ml). The precipitate is filtered off by suction, washed with water and then taken up in methylene chloride. The insoluble matter is fil-

TABLE F

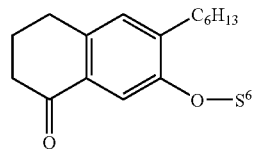

| Example | S⁶ | m.p. (° C.) | NMR(300 MHz) |
|---|---|---|---|
| 48 | —(CH₂)₃—COOH | 81 | (CDCl₃): 0.87(3H, m); 1.12-1.43(6H, m); 1.53(2H, m); 2.09(2H, m); 2.37-2.68(4H, m); 2.85(2H, m); 3.23(2H, m); 3.59(2H, m); 4.03(2H, m); 6.99(1H, s); 7.40(1H, s). |
| 49 | —CH₂—COOH | 174 | (CDCl₃): 0.87(3H, m); 1.14-1.45(6H, m); 1.62(2H, m); 2.09(2H, m); 2.59(2H, m); 2.68(2H, m); 2.86(2H, m); 4.67(2H, s); 7.02(1H, s); 7.33(1H, s) |
| 50 | CH₂-(3-COOH-phenyl) | 150 | (DMSO-d6): 0.80(3H, m); 1.08-1.44(6H, m); 1.55(2H, m); 1.99(2H, m); 2.53(2H, m); 2.62(2H, m); 2.83(2H, m); 5.21(2H, s); 7.14(1H, s); 7.41(1H, s), 7.52(1H, m); 7.68(1H, m); 7.89(1H, m); 8.06(1H, m); 12.99(1H, broad s). |

Example 52

Step a: N-(6-bromo-3-oxoindan-5-yl)-2,2,2-trifluoroacetamide

A mixture of 6-nitro-5-bromo-1-indanone (15.0 g, 58.6 mmol), iron (16.36 g, 292.9 mmol) and NH₄Cl (1.56 g, 29.3 mmol) in ethanol (90 ml) and water (30 ml) is heated at reflux for one hour. The reaction mixture is filtered while hot and the insoluble matter is washed thoroughly with boiling ethanol. After concentrating to dryness, the residue is taken up in dichloromethane, washed with water and dried (Na₂SO₄). The expected product is obtained after concentration (9.3 g, yield: 70%).

m.p.=220° C. ¹H NMR-DMSO d⁶—δ(ppm): 2.54 (m, 2H); 2.92 (m, 2H); 5.49 (s, NH₂); 6.98 (s, 1H); 7.62 (s, 1H).

tered off. The filtrate is dried (Na₂SO₄) and then concentrated. Flash chromatography on silica (2/1 heptane/ethyl acetate) gives the expected coupling product (0.35 g, yield: 88%).

¹H NMR-CDCl₃—δ(ppm): 2.73 (m, 2H); 3.14 (m 2H); 4.02 (s, 2H); 6.98-7.15 (m, 4H); 7.40 (s, 1H); 7.64 (broad s, NH), 8.07 (s, 1H).

The above coupling product (0.35 g, 1.0 mmol) is treated with a mixture of ethyl4-bromobutyrate (0.39 g, 2.0 mmol), K₂CO₃ (4.0 mmol, 0.54 g) and KI (0.16 g, 1 mmol), in acetone (9.6 ml) for 5 hours at reflux.

Ethyl4-bromobutyrate (0.39 g) and KI (0.16 g) are added, and the reaction mass is stirred for a further 4 hours at reflux and then concentrated to dryness. The obtained residue is taken up in ethyl ether and the insoluble matter is filtered off.

The concentrated filtrate is purified by chromatography on silica (2/1 heptane/ethyl acetate). 0.17 g of the expected product is obtained (yield: 36%).

$^1$H NMR-CDCl$_3$—δ(ppm): 1.22 (t, 3H); 1.92 (m, 2H); 2.31 (m, 2H); 2.72 (m, 2H); 2.92 (m, 1H); 3.09 (m, 2H); 3.86 (d, 1H); 3.96 (d, 1H); 4.09 (q, 2H); 4.23 (m, 1H); 6.97-7.13 (m, 4H); 7.18 (s, 1H); 7.55 (s, 1H).

The ester thus obtained (0.17 g, 0.365 mmol) is then treated with a mixture of NaOH (44 mg, 0.11 mol) in methanol (7.3 ml) and water (3.6 ml) for 18 hours at room temperature. The solvents are evaporated off and the residue is taken up in water. After acidification to pH 3.8 (pH-meter) with 1N hydrochloric acid, extraction with ethyl ether and drying (Na$_2$SO$_4$), the evaporation residue obtained (110 mg) is purified by flash chromatography on silica (95/5 dichloromethane/methanol). A yellow solid is obtained (90 mg, 72%).

m.p.=144-145° C. $^1$H NMR-CDCl$_3$—δ(ppm): 1.84 (m, 2H); 2.29 (t, 2H); 2.62-2.69 (m, 2H); 2.96-3.02 (m, 2H); 3.15 (t, 2H); 3.86 (s, 2H); 5.08 (broad s, NH and CO$_2$H); 6.90-7.03 (m, 3H); 7.05-7.15 (m, 3H).

Example 54

4-[6-(4-Fluorophenyl)-3-oxoindan-5-ylamino]butyric acid

A mixture of the product obtained in step a of Example 63 (0.5 g, 1.55 mmol), tetrakis(triphenylphosphine)palladium (46 mg), Na$_2$CO$_3$ (0.33 g, 3.11 mmol), water (1.2 ml), toluene (6.8 ml) and p-fluorophenylboronic acid (0.24 g, 1.72 mmol) is heated at reflux for 3 hours. Catalyst (46 mg), Na$_2$CO$_3$ (66 mg) and p-fluorophenylboronic acid (48 mg) are added, and the reaction mass is stirred for a further one hour at reflux. After addition of ethyl ether, the organic phase is washed with water, dried (Na$_2$SO$_4$) and concentrated. Flash chromatography (1/1 heptane/ethyl acetate) gives a vitreous solid (0.59 g), which is dispersed in a 2/1 mixture of heptane/ethyl acetate to give 0.37 g (yield: 71%) of the desired coupling product.

$^1$H NMR-CDCl$_3$—δ(ppm): 2.73-2.80 (m, 2H); 3.13-3.20 (m, 2H); 7.22-7.27 (m, 2H); 7.31-7.38 (m, 2H); 7.42 (s, 1H); 7.84 (broad s, NH); 8.53 (s, 1H).

The above coupling product (0.37 g, 1.1 mmol) is treated with a mixture of ethyl4-bromobutyrate (0.43 g, 2.2 mmol), K$_2$CO$_3$ (0.6 g, 4.4 mmol) and KI (0.18 g, 1.1 mmol) in acetone (10.6 ml) for 5 hours at reflux. The bromo ester (0.43 g) and KI (0.18 g) are added, and the reaction mass is stirred for a further 4 hours at reflux, followed by concentrating to dryness. The residue obtained is taken up in ethyl ether and the insoluble matter is filtered off. The concentrated filtrate is purified by chromatography on silica (3/1 heptane/ethyl acetate). 0.28 g of the expected product is obtained (56%).

$^1$H NMR—CDCl$_3$—δ(ppm): 1.19 (t, 3H); 1.63-1.79 (m, 2H); 2.06-2.31 (m, 2H); 2.56 (m, 1H); 2.74-2.83 (m, 2H); 3.18-3.25 (m, 2H); 3.80 (m, 1H); 4.04 (q, 2H); 7.09-7.18 (m, 2H); 7.25-7.31 (m, 2H); 7.52 (s, 1H); 7.59 (s, 1H).

The ester thus obtained (0.28 g, 0.62 mmol) is then treated with a mixture of sodium hydroxide (74 mg, 1.85 mmol) in methanol (12.4 ml) and water (6.2 ml) for 18 hours at room temperature. The solvents are evaporated off and the residue is taken up in water. After acidification to pH 4.2 with 1N hydrochloric acid, extraction with ethyl ether and drying (Na$_2$SO$_4$), the evaporation residue obtained (180 mg) is purified by flash chromatography on silica (95/5 dichloromethane/methanol). A yellow solid is obtained (150 mg, 75%).

m.p.=148-150° C. $^1$H NMR-CDCl$_3$—δ(ppm): 1.89 (m, 2H); 2.40 (t, 2H); 2.65-2.72 (m, 2H); 3.00-3.06 (m, 2H); 3.18 (t, 2H); 6.96 (s, 1H); 7.10-7.18 (m, 3H); 7.31-7.39 (m, 2H).

The derivatives of Table G below are prepared by following the procedures for the preparation of the derivatives of Example 52 and Example 54:

TABLE G

| Example | S$^7$ | m.p. (° C.) | $^1$H NMR(300 MHz) |
|---|---|---|---|
| 51 | —C$_6$H$_4$—CF$_3$ (para) | 149-151 | (CDCl$_3$): 1.72-2.04(2H, m); 2.27-2.57(2H, m); 2.57-2.82(2H, m); 2.90-3.10(2H, m); 3.10-3.36(2H, m); 4.49-6.48(2H, broad s); 6.99(1H, s); 7.14(1H, s); 7.35-7.61(2H, m); 7.61-7.86(2H, m). |
| 52 | —CH$_2$—C$_6$H$_4$—F (para) | 144-145 | (CDCl$_3$): 1.84(m, 2H); 2.29(t, 2H); 2.62-2.69(m, 2H); 2.96-3.02(m, 2H); 3.15(t, 2H); 3.86(s, 2H); 5.08(broad s, NH and CO$_2$H); 6.90-7.03(m, 3H); 7.05-7.15(m, 3H). |
| 53 | —CH$_2$—C$_6$H$_4$—OCH$_3$ (ortho) | 165-167 | (CDCl$_3$): 1.74-1.99(2H, m); 2.21-2.40(2H, m); 2.51-2.73(2H, m); 2.88-3.07(2H, m); 3.09-3.24(2H, m); 3.73-3.87(2H, m); 3.88(3H, s); 6.80-6.94(3H, m); 6.96-7.06(1H, m); 7.11-7.23(2H, m). |
| 54 | —C$_6$H$_4$—F (para) | 148-150 | (CDCl$_3$): 1.89(m, 2H); 2.40(t, 2H); 2.65-2.72(m, 2H); 3.00-3.06(m, 2H); 3.18(t, 2H); 6.96(s, 1H); 7.10-7.18(m, 3H); 7.31-7.39(m, 2H). |

TABLE G-continued

Structure: 2,3-dihydro-1H-inden-1-one with S⁷ substituent at 5-position and NH—(CH₂)₃—COOH at 6-position

| Example | S⁷ | m.p. (° C.) | $^1$H NMR(300 MHz) |
|---|---|---|---|
| 55 | —CH₂-(3,4-difluorophenyl) | 132 | (DMSO-d6): 1.76(2H, m); 2.21(2H, m); 2.48(2H, m); 2.89(2H, m); 3.08(2H, m); 3.92(2H, s); 5.27(1H, broad m); 6.66(1H, s); 7.08(2H, m); 7.32(2H, m); 12.06(1H, broad s). |
| 56 | —CH₂-(3,5-difluorophenyl) | 168 | (DMSO-d6): 1.75(2H, m); 2.22(2H, m); 2.52(2H, m); 2.90(2H, m); 3.08(2H, m); 3.96(2H, s); 5.26(1H, broad m); 6.67(1H, s); 6.82-7.24(4H, m); 12.02(1H, broad s). |
| 57 | —CH₂-(4-methylphenyl) | 158 | (DMSO-d6): 1.99(2H, m); 2.41(2H, m); 2.49(3H, s); 2.84(2H, m); 3.18(2H, m); 3.31(2H, m); 4.05(2H, s); 7.09(1H, s); 7.15-7.38(4H, m); 7.43(1H, s) NB: 2H, exchangeable, very broad s from 3.0 to 5.0. |
| 58 | —CH₂-(4-methoxyphenyl) | 160 | (DMSO-d6): 1.76(2H, m); 2.24(2H, m); 2.51(2H, m); 2.86(2H, m); 3.07(2H, m); 3.71(3H, s); 3.83(2H, s); 5.11(1H, broad m); 6.65(1H, s); 6.86(2H, m); 6.99(1H, s); 7.15(2H, m); 12.08(1H, very broad s). |
| 59 | —CH₂-(4-ethoxyphenyl) | 146 | (DMSO-d6): 1.29(3H, m); 1.76(2H, m); 2.24(2H, m); 2.51(2H, m); 2.86(2H, m); 3.07(2H, m); 3.83(2H, s); 3.97(2H, m); 5.11(1H, broad m); 6.65(1H, s); 6.84(2H, m); 6.99(1H, s); 7.12(2H, m); 12.09(1H, very broad s). |
| 60 | bicyclo[2.2.2]octyl | 158 | (DMSO-d6): 0.93-1.71(8H, m); 1.80(2H, m); 1.99(1H, m); 2.31(3H, m); 2.44(2H, m); 2.69(1H, m); 2.92(2H, m); 3.10(2H, m); 4.93(1H, broad m); 6.61(1H, s); 7.21(1H, s); 12.04(1H, broad s). |
| 61 | 2,3-dimethylphenyl | — | (DMSO-d6): 1.65(2H, m); 2.05(3H, s); 2.18(2H, m); 2.59(2H, m); 2.95(2H, m); 3.07(2H, m); 4.21(1H, broad m); 6.78(1H, s); 7.06(1H, s); 7.11(1H, m); 7.21-7.45(3H, m); 12.05(1H, very broad s). |
| 62 | 3,5-dimethylphenyl | — | (DMSO-d6): 1.70(2H, m); 2.23(2H, m); 2.36(3H, s); 2.60(2H, m); 2.95(2H, m); 3.07(2H, m); 4.66(1H, broad m); 6.77(1H, s); 7.15(1H, s); 7.16-7.27(3H, m); 7.37(1H, m); 12.07(1H, very broad s). |
| 63 | 2,4-dimethylphenyl (with additional CH₃) | — | (DMSO-d6): 1.70(2H, m); 2.24(2H, m); 2.26(6H, s); 2.58(2H, m); 2.93(2H, m); 3.09(2H, m); 4.64(1H, broad m); 6.75(1H, s); 7.13(1H, s); 7.14-7.33(3H, m); 12.05(1H, very broad s). |

TABLE G-continued

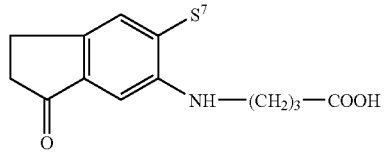

| Example | S⁷ | m.p. (° C.) | ¹H NMR(300 MHz) |
|---|---|---|---|
| 64 | (3-methyl, OCH₃ phenyl) | — | (DMSO-d6): 1.71(2H, m); 2.24(2H, m); 2.58(2H, m); 2.95(2H, m); 3.07(2H, m); 3.79(3H, s); 4.75(1H, broad m); 6.77(1H, s); 6.98(1H, m); 7.18(1H, s); 7.40(1H, m); 7.47-7.73(2H, m); 12.05(1H, very broad s). |
| 65 | (4-methyl, O—CH₃ phenyl) | — | (DMSO-d6): 1.71(2H, m); 2.23(2H, m); 2.58(2H, m); 2.95(2H, m); 3.06(2H, m); 3.80(3H, s); 4.67(1H, broad m); 6.75(1H, s); 7.05(2H, m); 7.13(1H, s); 7.35(2H, m); 12.08(1H, very broad s). |

Example 66

Step a: Ethyl3-(3-bromo-4-methoxyphenyl)propanoate 87.5 g of bromine are added dropwise at 25° C. over 3 hours to a solution of ethyl3-(4-methoxyphenyl)propanoate (113.9 g; 0.545 mol) in 900 ml of chloroform. The mixture is poured into water and the organic phase is separated out by settling of the phases and washed with 10% sodium hydrosulfite solution. After drying and evaporating off the solvents, a yellow oil is collected (154 g; 98%).

¹H NMR —CHCl₃—δ(ppm): 1.22 (3H, m); 2.56 (2H, m); 2.85 (2H, m); 3.85 (3H, s); 4.11 (2H, m); 6.81 (1H, m); 7.09 (1H, m); 7.38 (1H, m).

Step b: 3-(3-Bromo-4-methoxyphenyl)propanoic acid.

154 g (0.535 mol) of ethyl3-(3-bromo-4-methoxyphenyl) propanoate are mixed with 45 g (0.8 mol) of potassium hydroxide, 600 ml of methanol and 300 ml of water. The mixture is heated at reflux for 3 hours, and the methanol is then evaporated off. The solution obtained is washed with ether; the aqueous phase is acidified and extracted with ether. The organic phase is dried (Na₂SO₄), and the solvents are evaporated off: white solid (132.7 g; 96%).

¹H NMR —CHCl₃—δ (ppm): 2.64 (2H, m); 2.87 (2H, m); 3.86 (3H, s); 6.82 (1H, m); 7.10 (1H, m); 7.39 (1H, m); 11.17 (1H, very broad s).

Step c: 3-(3-Bromo-4-methoxyphenyl)propanoyl chloride

A solution of 102.4 g (0.86 mol) of thionyl chloride is added to a solution of 51.8 g (0.2 mol) of 3-(3-bromo-4-methoxyphenyl)propanoic acid in 700 ml of chloroform. The mixture is heated at reflux for 4 hours, and the solvent is then evaporated off. 53 g are obtained.

¹H NMR —CHCl₃—δ (ppm): 2.92 (2H, m); 3.16 (2H, m); 3.87 (3H, s); 6.83 (1H, m); 7.10 (1H, m); 7.37 (1H, m).

Step d: 5-Bromo-6-methoxyindan-1-one 48 g (0.18 mol) of 3-(3-bromo-4-methoxyphenyl)propanoyl chloride are dissolved in 500 ml of dichloromethane. 72 g (0.54 mol) of aluminium chloride are added in small amounts. The reaction medium is stirred for 2 hours and then poured into water and the phases are separated by settling. The organic phase is dried (Na₂SO₄) and the solvent is evaporated off: (39.8 g). The product is triturated in ethanol, filtered off and dried (25 g; 63%)

¹H NMR —CHCl₃—δ (ppm): 2.69 (2H, m); 3.05 (2H, m); 3.91 (3H, s); 7.17 (1H, s); 7.68 (1H, s).

Step e: 5-Bromo-6-hydroxyindan-1-one 46.7 g (0.35 mol) of aluminium chloride are added portionwise to a solution of 28.3 g (0.117 mol) of 5-bromo-6-methoxyindan-1-one in 500 ml of toluene. The reaction mixture is heated at reflux for 15 minutes and is then poured into water and the phases are separated by settling (sparingly soluble product).

The suspended solid is filtered off and the solvents are evaporated off. The solid residue is purified by flash chromatography (98/2 CH₂Cl₂/MeOH), and 22 g of solid are obtained (83%); m.p.=210° C.

¹H NMR —CHCl₃—δ (ppm): 2.69 (2H, m); 3.06 (2H, m); 5.73 (1H, s); 7.33 (1H, s); 7.63 (1H, s).

Step f: ethyl4-(6-bromo-3-oxoindan-5-yloxy)butyrate

A mixture of 4.2 g (0.0185 mol) of 5-bromo-6-hydroxyindan-1-one, 150 ml of acetone and 9 g (0.0276 mol) of caesium carbonate is heated for 30 minutes at 56° C. 5.4 g (0.227 mol) of ethyl4-bromobutyrate are added dropwise and the mixture is then heated at reflux for 7 hours.

The resulting mixture is poured into 1N hydrochloric acid solution and extracted with ether. The organic phase is dried (Na₂SO₄) and the solvents are evaporated off. The residue is triturated in hexane: solid, m.p.=95° C. (5 g; 79%).

¹H NMR —CHCl₃— δ (ppm): 1.25 (3H, m); 2.17 (2H, m); 2.57 (2H, m); 2.70 (2H, m); 4.09 (2H, m); 4.14 (2H, m); 7.16 (1H, s); 7.69 (1H, s).

Step g: ethyl4-[3-oxo-6-(4-trifluorormethylphenyl)indan-5-yloxy]butyrate

A mixture of 1.2 g (3.5 mmol) of ethyl4-(6-bromo-3-oxoindan-5-yloxy)butyrate, 25 ml of toluene, 3.9 ml of sodium bicarbonate solution (at 2 mol per litre), 5 ml of ethanol, 0.8 g (42 mmol) of 4-(trifluoromethyl)phenylboronic acid and 77 mg (0.007 mmol) of tetrakis(triphenylphosphine)palladium (0) is heated at reflux for 2 hours. The mixture is poured into a mixture of 30 ml of water, 8 ml of aqueous ammonia and 10 ml of sodium carbonate solution (2 mol per litre). The resulting mixture is extracted with ether and, after drying and evaporation, 1.4 g of product purified by flash chromatography (98/2 dichloromethane/methanol) (1.22 g, 84%) are collected.

¹H NMR —CHCl₃— δ (ppm): 1.23 (3H, m); 2.04 (2H, m); 2.36 (2H, m); 2.74 (2H, m); 3.11 (2H, m); 4.04 (2H, m); 4.10 (2H, m); 7.28 (1H, s); 7.39 (1H, s); 7.56-7.85 (4H, m).

Step h: 4-[3-oxo-6-(4-trifluoromethylphenyl)indan-5-yloxy]butyric acid 1.2 g (3 mmol) of ethyl4-[3-oxo-6-(4-trifluoromethylphenyl)indan-5-yloxy]butyrate are mixed with 250 mg (45 mmol) of potassium hydroxide, 40 ml of methanol and 10 ml of water. The mixture is heated at reflux for 2 hours and the methanol is then evaporated off. The solution obtained is washed with ether; the aqueous phase is acidified and extracted with dichloromethane. The organic phase is dried (Na₂SO₄) and the solvents are evaporated off: yellow solid (0.95 g). Purification of the compound by flash chromatography (98/2 dichloromethane/methanol) [lacuna] (0.56 g; 50%).

¹H NMR-CHCl₃— δ (ppm): 2.05 (2H, m); 2.42 (2H, m); 2.75 (2H, m); 3.11 (2H, m); 4.06 (2H, m); 7.28 (1H, s); 7.39 (1H, s); 7.55-7.77 (4H, m)

N.B.: acid H not observed.

Examples 67 to 69

The additional Examples 67 to 69, prepared from the compound obtained as an intermediate in step f) of Example 66, are collated in Table H below.

TABLE H

![structure]

| Example | S⁸ | S⁹ | ¹H NMR(300 MHz) |
|---|---|---|---|
| 67 | 4-fluorophenyl | H | (DMSO-d6): 1.76-2.04(2H, m); 2.21-2.35(2H, m); 2.59-2.73(2H, m); 2.94-3.12(2H, m); 3.95-4.16(2H, m); 7.15-7.33(3H, m); 7.45-7.64(3H, m); 12.13(1H, broad s). |
| 68 | 4-trifluoromethylphenyl | C₂H₅ | (CDCl₃): 0.99-1.23(3H, m); 1.80-2.02(2H, m); 2.13-2.32(2H, m); 2.50-2.71(2H, m); 2.86-3.09(2H, m); 3.78-4.11(4H, m); 7.07-7.21(2H, m); 7.42-7.68(4H, m). |
| 69 | 3,4-dichlorophenyl | H | (CDCl₃): 1.95-2.17(2H, m); 2.37-2.58(2H, m); 2.67-2.86(2H, m); 3.05-3.22(2H, m); 3.95-4.18(2H, m); 7.27-7.30(1H, m); 7.32-7.40(2H, m); 7.45-7.52(1H, m); 7.60-7.64(1H, m). |

Example 70

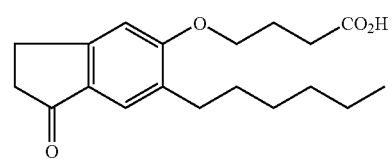

Step a:

A suspension of 6-hydroxy-5-methoxy-1-indanone (1.5 g; 8.42 mmol) in pyridine (4 ml) is cooled to 0° C., followed by addition of trifluoromethanesulfonic anhydride (1.6 ml; 9.51 mmol; 1.1 eq). The mixture is stirred for 1 hour and then poured into ice-cold 2N hydrochloric acid. The aqueous phase is extracted three times with ethyl acetate. The combined organic phases are washed with brine, dried and concentrated.

Flash chromatography (30% EtOAc/heptane) gives the expected product (1.34 g, yield: 51%) as a beige powder.

¹H NMR-CDCl₃—δ (ppm): 2.63-2.79 (2H, m); 3.04-3.22 (2H, m); 4.00 (3H, s); 7.06 (1H, s); 7.58 (1H, s).

Step b:

Hexylzinc bromide, as a 0.5N solution in tetrahydrofuran (14 ml; 7 mmol; 1.63 eq), is added quickly to a mixture, under nitrogen and at room temperature, of the product obtained from step a (1.34 g; 4.32 mmol) and dichlorobis(triphenylphosphine)palladium II (110 mg) in dry DMF (20 ml).

The reaction is slightly exothermic and the temperature of the reaction mixture rises to 37° C. After stirring for 35 minutes, the mixture is poured into ice-cold water (100 ml) comprising 1 N hydrochloric acid (10 ml) and ether.

The insoluble matter is filtered off and the aqueous phase is extracted two more times with ether. The combined organic phases are washed with water, dried and concentrated.

Flash chromatography (20% EtOAc/heptane) gives the expected product (0.2 g, yield: 19%) in the form of a beige powder.

¹H NMR-CDCl₃—δ (ppm): 0.76-0.98 (3H, m); 1.15-1.41 (4H, m); 1.45-1.71 (4H, m); 2.49-2.74 (4H, m); 2.98-3.17 (2H, m); 3.89 (3H, s); 6.83 (1H, s); 7.52 (1H, s).

Step c:

A mixture in toluene (5 ml) of the product obtained from step b (0.2 g; 0.81 mmol) and AlCl₃ (0.27 g; 2.0 mmol; 2.5 eq) is heated in a bath at 100° C. for 2 hours. The mixture is poured into ice-cold water comprising concentrated hydrochloric acid and diethyl ether. The aqueous phase is extracted two more times with diethyl ether. The combined organic phases are washed with water, dried and concentrated. A beige powder is obtained (0.14 g).

¹H NMR-CDCl₃—δ (ppm): 0.76-0.96 (3H, m); 1.16-1.45 (4H, m); 1.48-1.71 (4H, m); 2.54-2.72 (4H, m); 2.96-3.13 (2H, m); 6.74-6.89 (1H, broad s); 6.82 (1H, s); 7.55 (1H, s).

Step d: 4-(6-Hexyl-1-oxoindan-5-yloxy)butyric acid

A mixture of the product obtained from step c (0.14 g, 0.60 mmol), ethyl4-bromobutyrate (0.18 g; 0.92 mmol; 1.5 eq) and caesium carbonate (0.30 g; 0.92 mmol; 1.5 eq) in acetone (2 ml) is heated at reflux for 7 hours. The mixture is then poured into water and diethyl ether. The aqueous phase is extracted twice with diethyl ether. The combined organic phases are washed with water, dried and concentrated.

Flash chromatography (30% EtOAc/heptane) gives the product in the form of a brown oil (50 mg, yield: 24%).

This product is taken up in methanol (2 ml) and treated with 1 N sodium hydroxide (0.4 ml) for one hour. The mixture is poured into ice-cold 1 N hydrochloric acid and diethyl ether. The aqueous phase is extracted two more times with diethyl ether. The combined organic phases are washed with water and dried. The evaporation residue is recrystallised from cyclohexane. The expected product is obtained in the form of colourless bright crystals (16.7 mg).

m.p.=122° C. ¹H NMR-CDCl₃—δ (ppm): 0.76-0.97 (3H, m); 1.11-1.92 (8H, m); 2.06-2.29 (2H, m); 2.48-2.73 (6H, m); 2.92-3.12 (2H, m); 3.96-4.24 (2H, m); 6.81 (1H, s); 7.52 (1H, s).

Among the compounds that are especially preferred are:

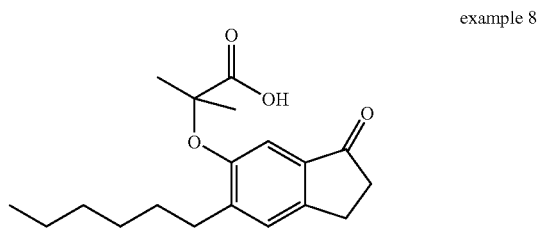

example 8

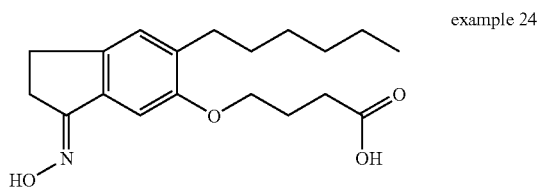

example 24

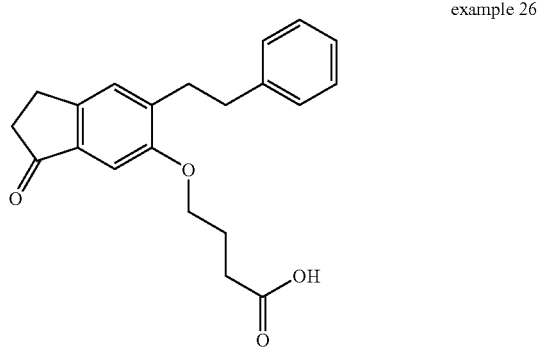

example 26

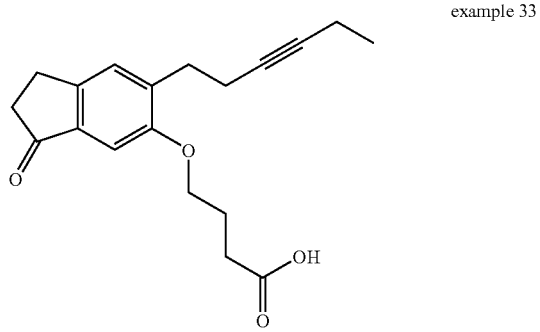

example 33

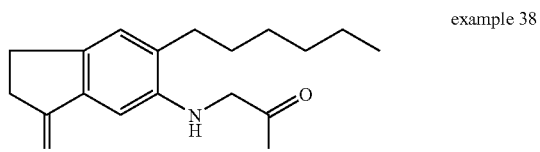

example 38

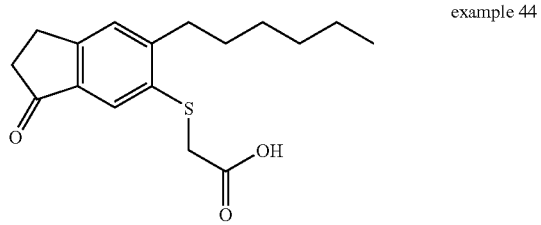

example 44

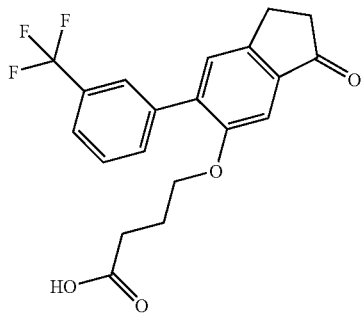
chemistry 55
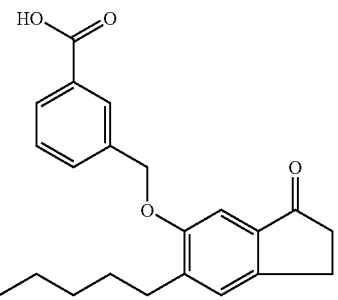
example 13
Compounds 71-176 were prepared according to the same types of procedures as in the preceding examples.
| No. | structure | MW | mass | NMR |
|---|---|---|---|---|
| 71 | 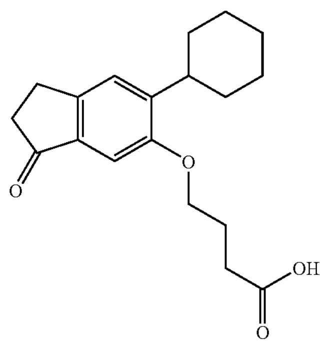 | 316.40 | | $^1$H NMR(300 MHz, CDCl$_3$) ppm: 1.3(m, 6H), 1.8(m, 4H), 2.2(dd, J=13.0, 6.2Hz, 2H), 2.6(m, 4H), 3.0(m, 3H), 4.0(t, J=5.8Hz, 2H), 7.1(s, 1H) 7.3(s, 1H) |
| 72 | 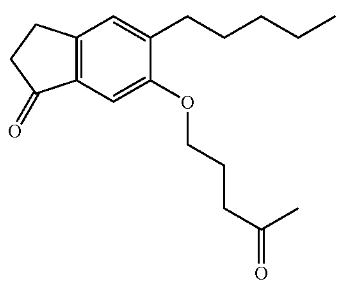 | 302.41 | | $^1$H NMR(300 MHz, DMSO-D$_6$) ppm: 0.8(t, J=6.5Hz, 3H), 1.2(m, 4H), 1.4(m, 2H), 1.9(m, 2H), 2.4(m, 6H), 2.9(m, 2H), 3.9(t, J=6.1Hz, 2H), 6.9(s, 1H), 7.2(s, 1H) 12.0(s, 1H) |
| 73 | 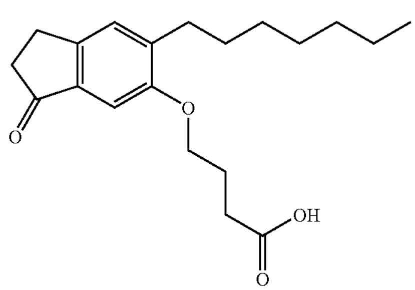 | 332.44 | ES+ 333.3 ES− 331.3 | |

-continued

| No. | structure | MW | mass | NMR |
|---|---|---|---|---|
| 74 | 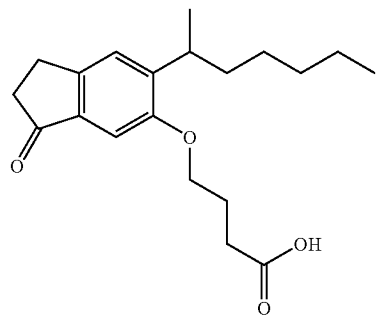 | 332.44 | ES+ 333.3<br>ES− 331.3 | |
| 75 | 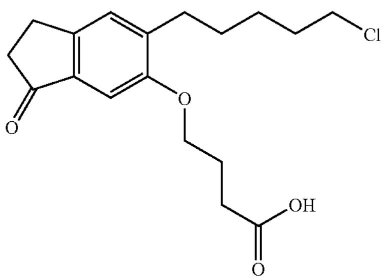 | 338.83 | ES+ 339.2/341.2<br>ES− 337.2/339.2 | |
| 76 | 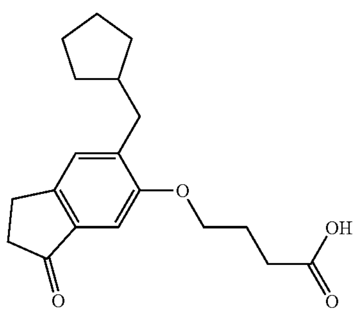 | 316.40 | ES+ 317.3<br>ES− 315.3 | |
| 77 | 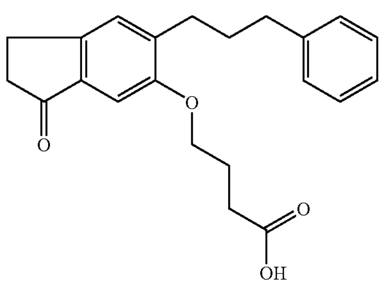 | 352.43 | | $^1$H NMR(300 MHz, DMSO-D$_6$) ppm: 1.3(m, 8H), 1.7(m, 2H), 2.0(m, 2H), 2.5(m, 5H), 3.0(m, 2H), 3.3(m, 4H), 4.0(t, J=6.1Hz, 2H), 7.0(s, 1H), 7.3(s, 1H), 12.1(s, 1H) |
| 78 | 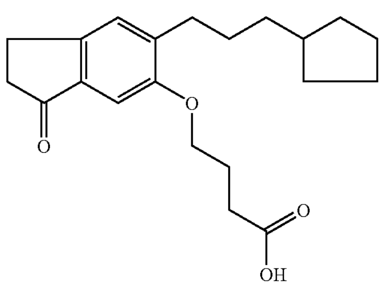 | 344.45 | | $^1$H NMR(300 MHz, CDCl$_3$) ppm: 1.9(m, 2H), 2.1(m, 2H), 2.6(m, 8H), 3.0(m, 2H), 4.0(m, 2H), 7.2(m, 7H) |

-continued

| No. | structure | MW | mass | NMR |
|---|---|---|---|---|
| 79 | 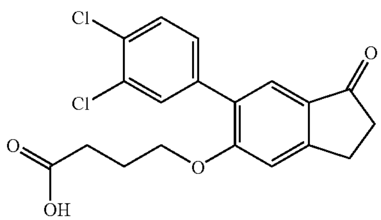 | 379.24 | ES+ 379.3/381.3 | |
| 80 | 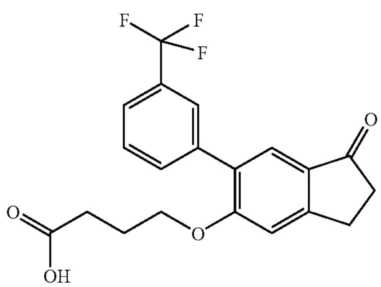 | 378.35 | ES+ 379.2 | |
| 81 | 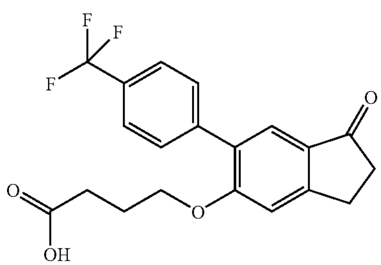 | 378.35 | ES+ 379.2 | |
| 82 | 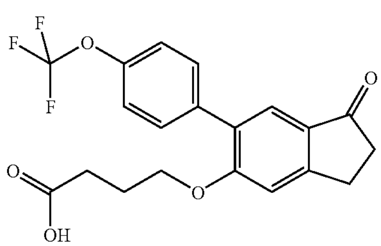 | 394.34 | ES+ 395.3 | |
| 83 | 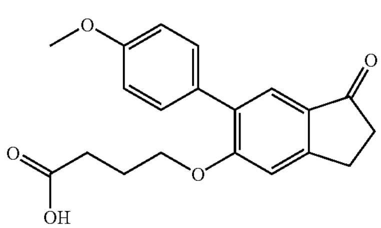 | 340.37 | ES+ 341.3 | |
| 84 | 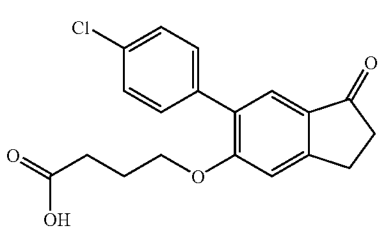 | 344.79 | ES+ 345.2/347.2<br>ES− 343.2/345.2 | |

| No. | structure | MW | mass | NMR |
|---|---|---|---|---|
| 85 | 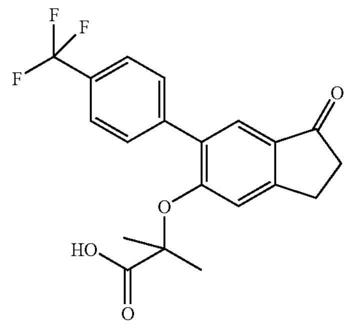 | 378.35 | ES+ 379.3 | |
| 86 | 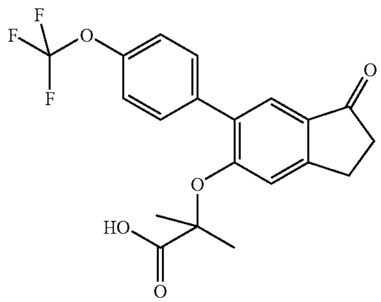 | 394.34 | ES− 393.3 | |
| 87 | 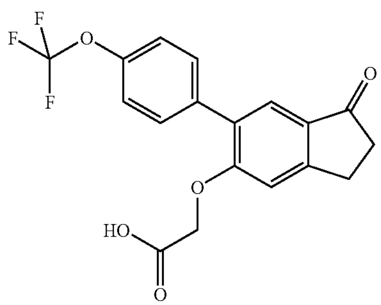 | 366.29 | ES− 365.3 | |
| 88 | 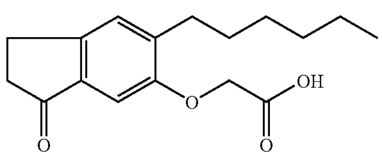 | 290.36 | | $^1$H NMR(300 MHz, CDCl$_3$) ppm: 0.9(t, J=6.6Hz, 3H), 1.3(m, 6H), 1.6(m, 2H), 2.7(m, 4H), 3.0(m, 2H), 4.8(s, 2H), 7.1(s, 1H), 7.3(s, 1H) |
| 89 | 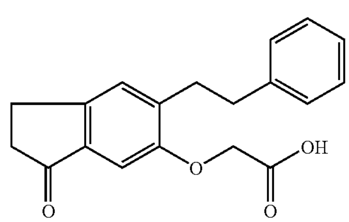 | 310.35 | | $^1$H NMR(300 MHz) ppm: 2.6(m, 2H), 2.9(m, 6H), 4.7(d, J=6.3Hz, 2H), 7.1(m, 7H) |
| 90 | 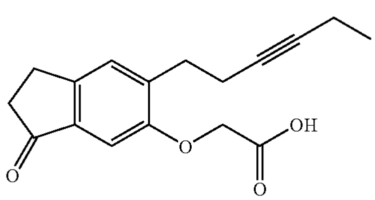 | 286.33 | ES+ 287.3<br>ES− 285.3 | |

-continued

| No. | structure | MW | mass | NMR |
|-----|-----------|-----|------|-----|
| 91 | 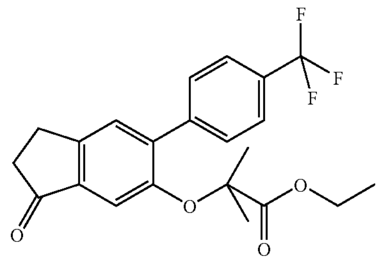 | 406.40 | ES+ 407.2 | |
| 92 | 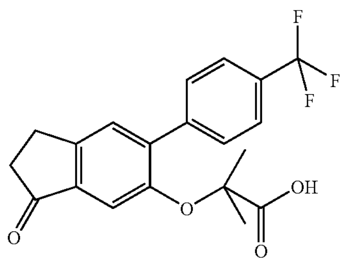 | 378.35 | ES- 377.2 | |
| 93 | 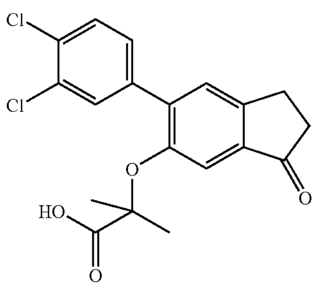 | 379.24 | ES- 377.1/379.1/381.1 | |
| 94 | 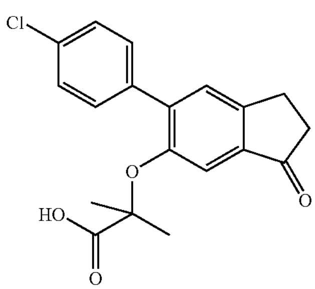 | 344.79 | ES- 343.3/345.3 | |
| 95 | 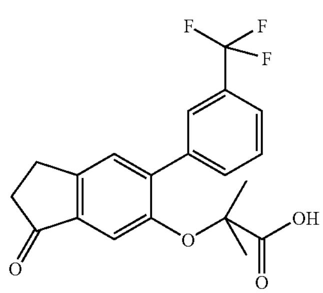 | 378.35 | ES- 377.2 | |

-continued

| No. | structure | MW | mass | NMR |
|---|---|---|---|---|
| 96 | 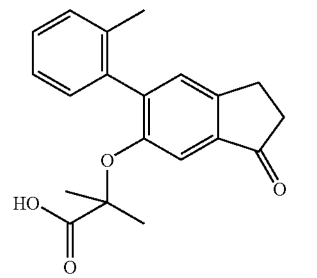 | 324.38 | ES+ 325.2<br>ES− 323.2 | |
| 97 | 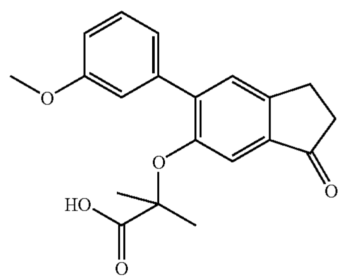 | 340.37 | ES− 339.2 | |
| 98 | 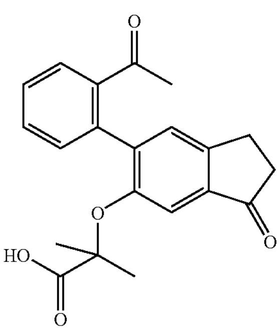 | 352.39 | ES+ 353.2<br>ES− 351.2 | |
| 99 | 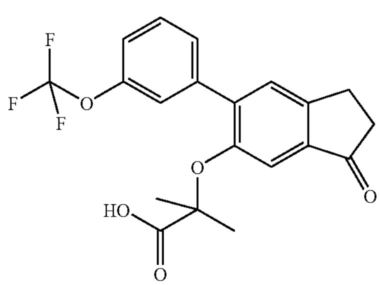 | 394.34 | ES− 393.2 | |
| 100 | 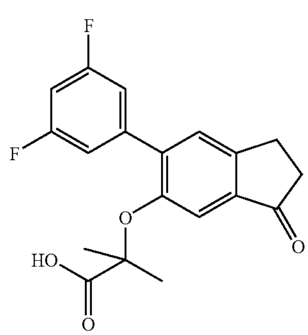 | 346.33 | ES+ 347.2<br>ES− 345.2 | |

-continued

| No. | structure | MW | mass | NMR |
|---|---|---|---|---|
| 101 | 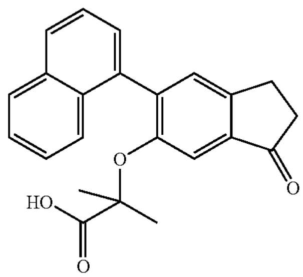 | 360.41 | ES+ 361.2<br>ES− 359.2 | |
| 102 | 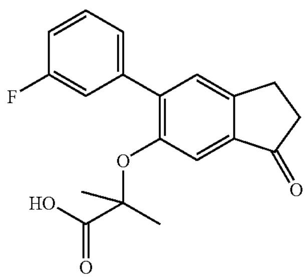 | 328.34 | ES+ 329.2<br>ES− 327.2 | |
| 103 | 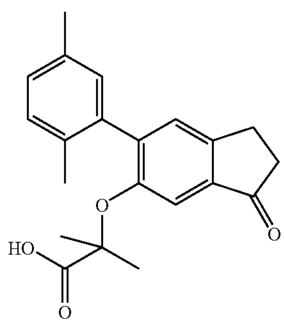 | 338.40 | ES+ 339.2<br>ES− 337.2 | |
| 104 | 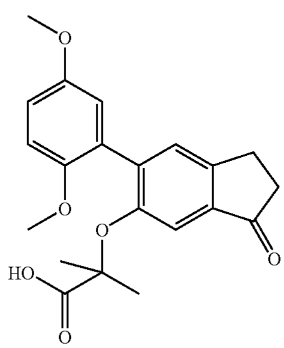 | 370.40 | ES+ 371.2<br>ES− 369.2 | |
| 105 | 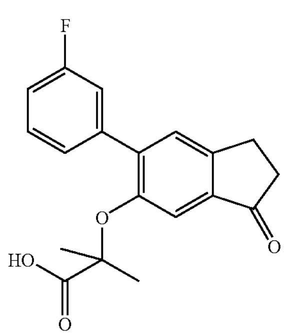 | 328.34 | ES+ 329.2<br>ES− 327.2 | |

-continued

| No. | structure | MW | mass | NMR |
|---|---|---|---|---|
| 106 | 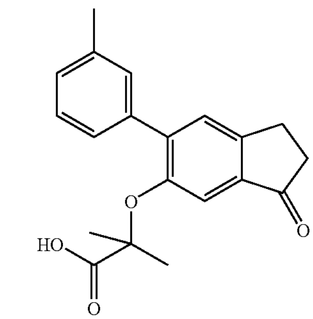 | 324.38 | ES+ 325.2<br>ES− 323.2 | |
| 107 | 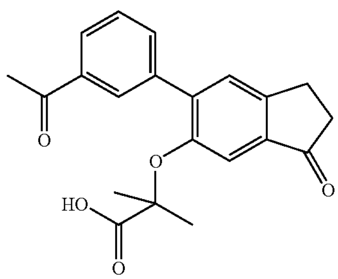 | 352.39 | ES− 351.2 | |
| 108 | 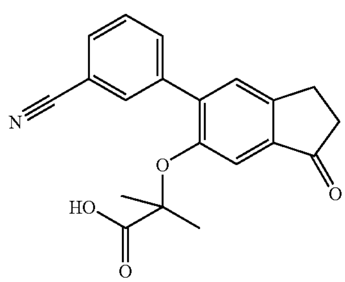 | 335.36 | ES− 334.2 | |
| 109 | 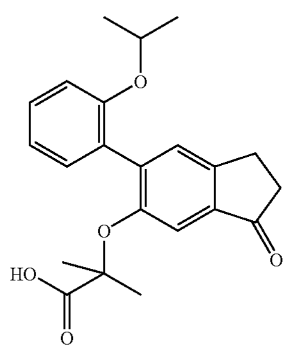 | 346.33 | ES− 345.2 | |
| 110 | 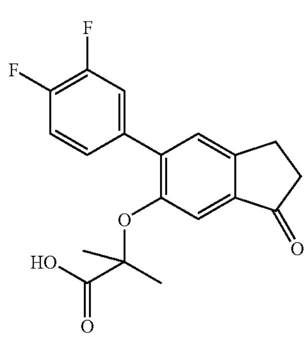 | 346.33 | ES− 345.2 | |

-continued
| No. | structure | MW | mass | NMR |
|---|---|---|---|---|
| 111 | 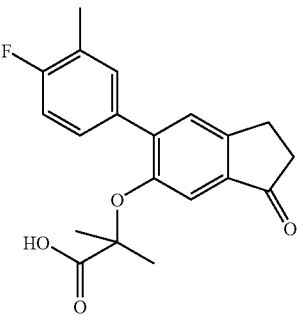 | 342.37 | ES− 341.2 | |
| 112 | 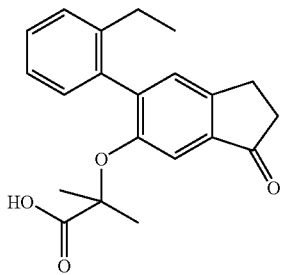 | 338.40 | ES+ 339.2<br>ES− 337.2 | |
| 113 | 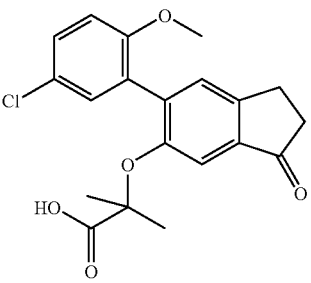 | 374.82 | ES− 373.1/375.1 | |
| 114 | 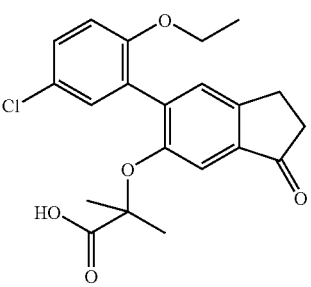 | 388.85 | ES− 387.2/389.2 | |
| 115 | 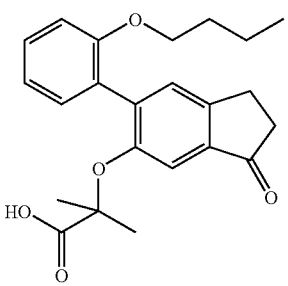 | 382.46 | ES+ 383.2<br>ES− 381.2 | |

| No. | structure | MW | mass | NMR |
|-----|-----------|-----|------|-----|
| 116 | 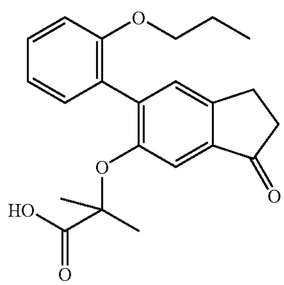 | 368.43 | ES+ 369.2 ES− 367.2 | |
| 117 | 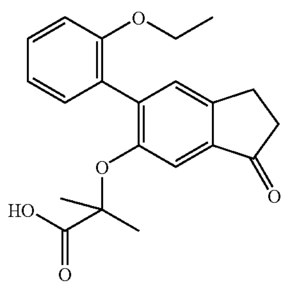 | 354.40 | ES+ 355.2 ES− 353.2 | |
| 118 | 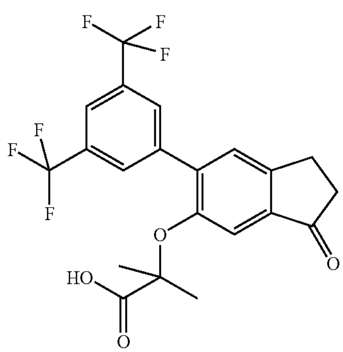 | 446.34 | ES− 445.2 | |
| 119 | 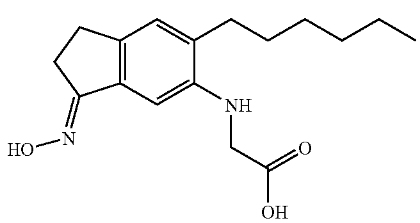 | 304.39 | ES+ 305.3 ES− 303.3 | |
| 120 | 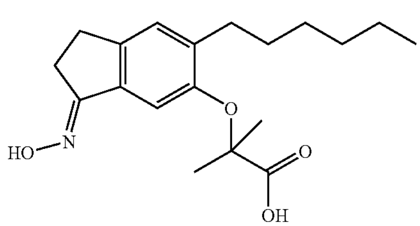 | 333.43 | ES+ 334.3 ES− 332.3 | |

| No. | structure | MW | mass | NMR |
|---|---|---|---|---|
| 121 | 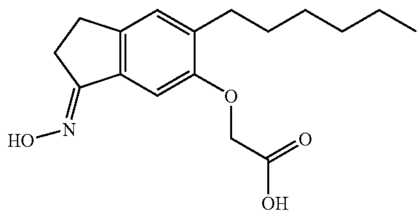 | 305.37 | | $^1$H NMR(300 MHz, CDCl$_3$) ppm: 0.9(t, J=6.6Hz, 3H), 1.3(m, 6H), 1.6(m, 2H), 2.7(m, 2H), 3.0(m, 4H), 4.8(s, 2H), 7.0(s, 1H), 7.1(s, 1H), 7.3(s, 1H) |
| 122 | 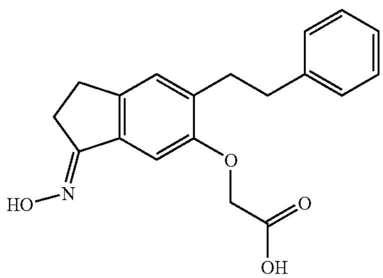 | 325.36 | | $^1$H NMR(300 MHz) ppm: 2.9(m, 8H), 4.8(s, 2H), 7.0(s, 1H), 7.3(m, 7H), 10.8(s, 1H) |
| 123 | 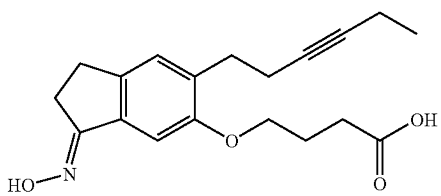 | 329.40 | | $^1$H NMR(300 MHz, DMSO-d$_6$) ppm: 1.0(t, J=7.4Hz, 3H), 2.0(m, 4H), 2.4(m, 4H), 2.8(m, 6H), 4.0(t, J=6.3Hz, 2H), 7.0(s, 1H), 7.1(s, 1H), 10.7(s, 2H) |
| 124 | 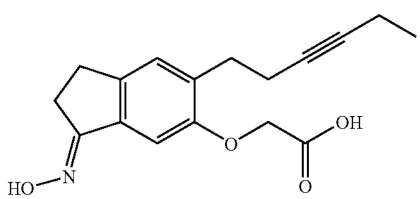 | 301.34 | ES+ 302.3<br>ES− 300.3 | |
| 125 | 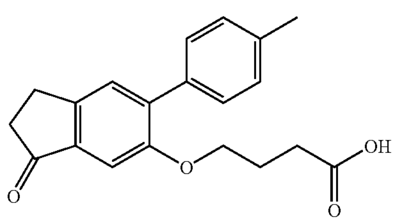 | 324.38 | ES+ 325.2<br>ES− 323.2 | |
| 126 | 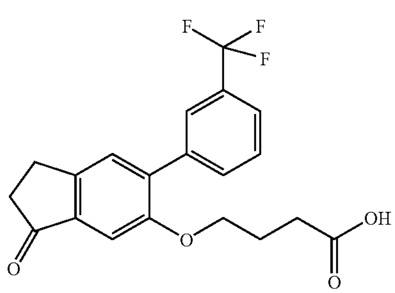 | 378.35 | ES+ 379.3<br>ES− 377.3 | |

-continued
| No. | structure | MW | mass | NMR |
|---|---|---|---|---|
| 127 | 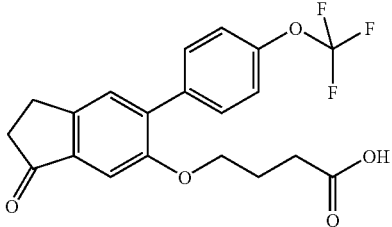 | 394.34 | ES+ 395.3 | |
| 128 | 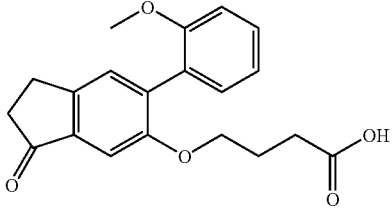 | 340.37 | ES+ 341.3<br>ES− 339.3 | |
| 129 | 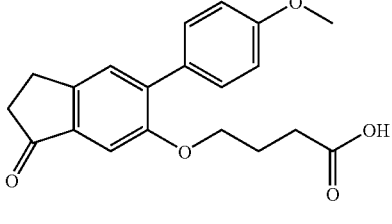 | 340.37 | ES+ 341.3 | |
| 130 | 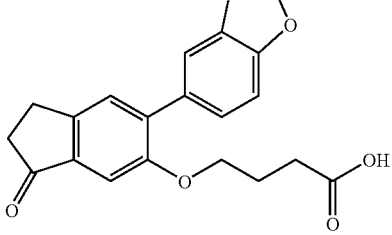 | 354.36 | ES+ 355.3 | |
| 131 | 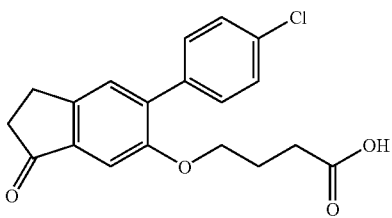 | 344.79 | ES− 343.3/345.3 | |
| 132 | 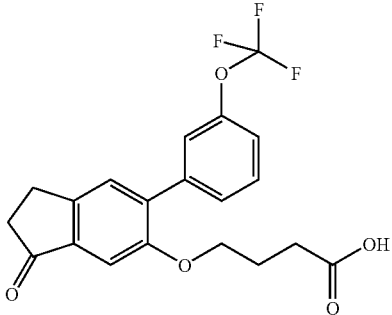 | 394.34 | ES+ 395.2<br>ES− 393.2 | |

-continued
| No. | structure | MW | mass | NMR |
|---|---|---|---|---|
| 133 | 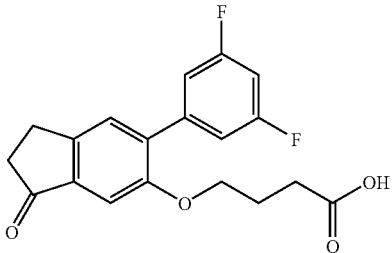 | 346.33 | ES− 345.2 | |
| 134 | 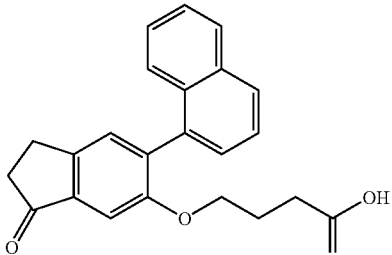 | 360.41 | ES− 359.2 | |
| 135 | 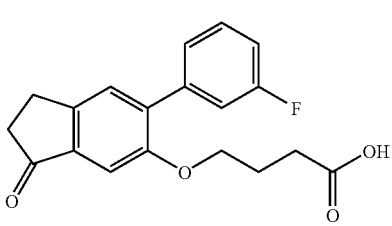 | 328.34 | ES− 327.2 | |
| 136 | 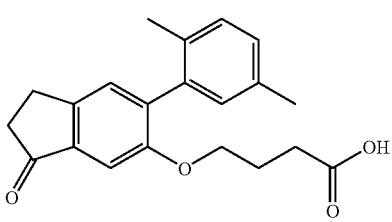 | 338.40 | ES+ 339.2<br>ES− 337.2 | |
| 137 | 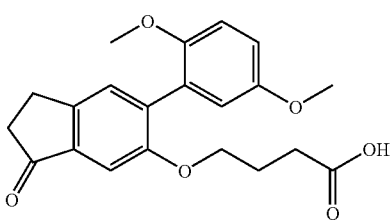 | 370.40 | ES+ 371.2<br>ES− 369.2 | |
| 138 | 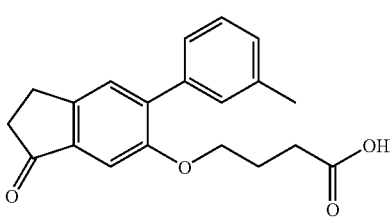 | 324.38 | ES+ 325.2<br>ES− 323.2 | |

| No. | structure | MW | mass | NMR |
|---|---|---|---|---|
| 139 | 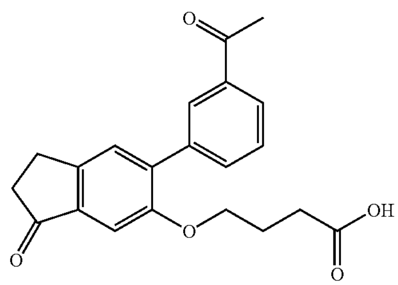 | 352.39 | ES− 351.2 | |
| 140 | 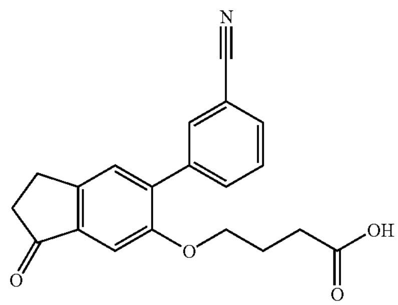 | 335.36 | ES+ 336.2<br>ES− 334.2 | |
| 141 | 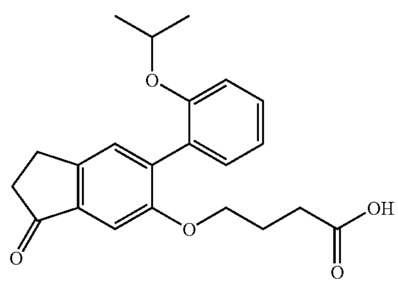 | 368.43 | ES+ 369.2<br>ES− 367.2 | |
| 142 | 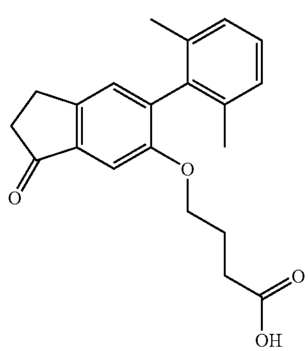 | 338.40 | ES+ 339.2 | |
| 143 | 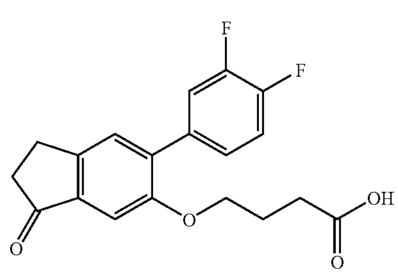 | 346.33 | ES− 345.2 | |

-continued

| No. | structure | MW | mass | NMR |
|---|---|---|---|---|
| 144 | 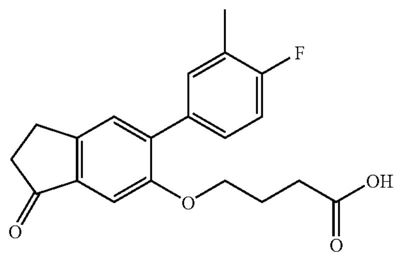 | 342.37 | ES+ 343.2<br>ES− 341.2 | |
| 145 | 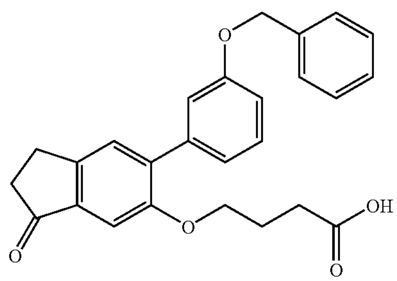 | 416.47 | ES− 415.2 | |
| 146 | 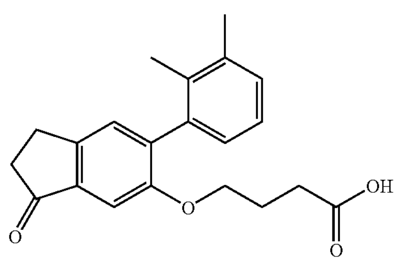 | 338.40 | ES+ 339.2<br>ES− 337.2 | |
| 147 | 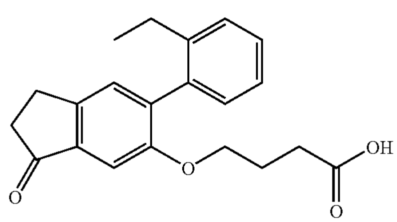 | 338.40 | ES+ 339.2<br>ES− 337.2 | |
| 148 | 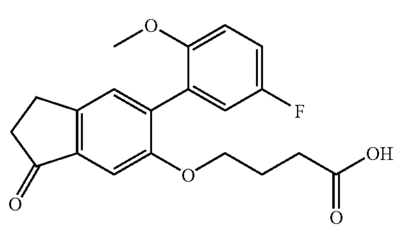 | 358.36 | ES+ 359.2<br>ES− 357.2 | |
| 149 | 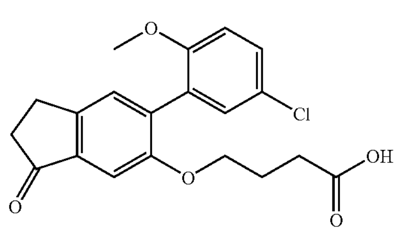 | 374.82 | ES− 373.1/375.1 | |

-continued

| No. | structure | MW | mass | NMR |
|---|---|---|---|---|
| 150 | 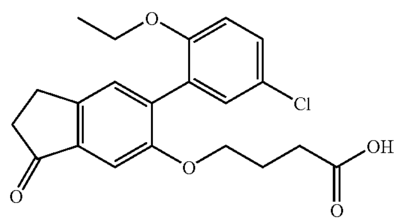 | 388.85 | ES− 387.2/389.2 | |
| 151 | 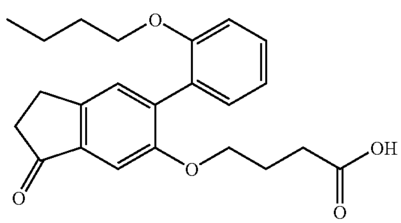 | 382.46 | ES+ 383.2<br>ES− 381.2 | |
| 152 | 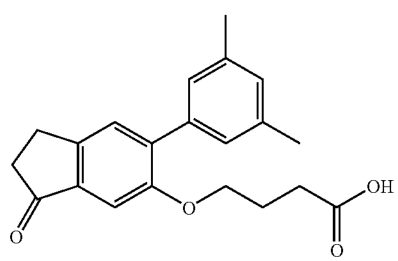 | 338.40 | ES+ 339.2<br>ES− 337.2 | |
| 153 | 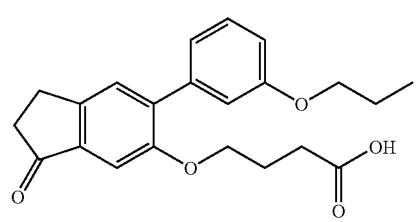 | 368.43 | ES− 367.2 | |
| 154 | 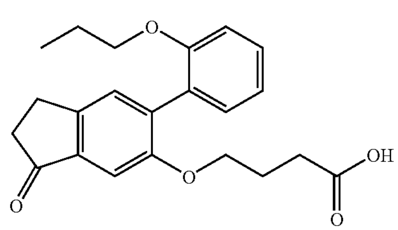 | 368.43 | ES+ 369.2<br>ES− 367.2 | |
| 155 | 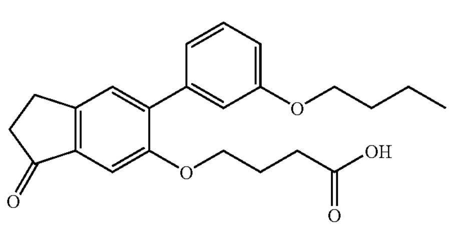 | 382.46 | ES− 381.2 | |

| No. | structure | MW | mass | NMR |
|---|---|---|---|---|
| 156 | 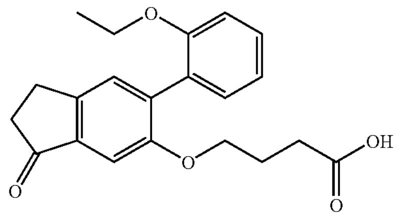 | 354.40 | ES+ 355.2<br>ES− 353.2 | |
| 157 | 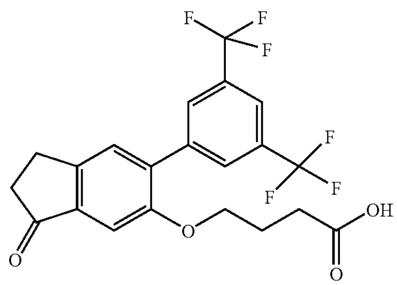 | 446.34 | ES− 445.2 | |
| 158 | 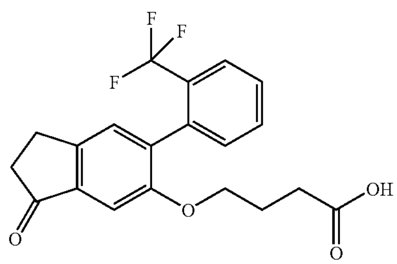 | 378.35 | ES+ 379.2<br>ES− 377.2 | |
| 159 | 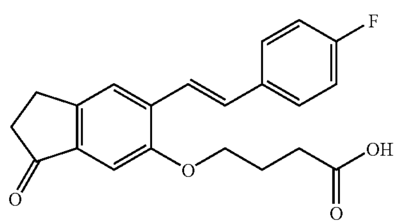 | 354.38 | ES− 353.2 | |
| 160 | 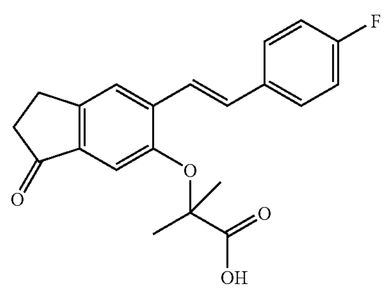 | 354.38 | ES− 353.2 | |
| 161 | 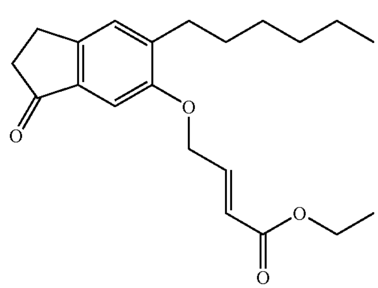 | 344.45 | | $^1$H NMR(300 MHz, CDCl$_3$) ppm: 0.9(m, 3H), 1.3(m, 7H), 1.6(m, 2H), 2.7(m, 4H), 3.0(m, 2H), 4.2(q, J=7.2Hz, 2H), 4.7(m, 2H), 6.2(d, J=15.8Hz, 1H), 7.1(m, 2H), 7.1(m, 2H), 7.2(s, 1H) |

-continued

| No. | structure | MW | mass | NMR |
|---|---|---|---|---|
| 162 | 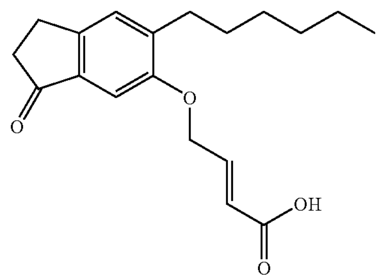 | 316.40 | | $^1$H NMR(300 MHz, CDCl$_3$) ppm: 0.9(m, 3H), 1.5(m, 9H), 2.7(m, 4H), 3.0(m, 2H), 4.8(m, 2H), 6.2(d, J=15.4Hz, 1H), 7.2(m, 3H) |
| 163 | 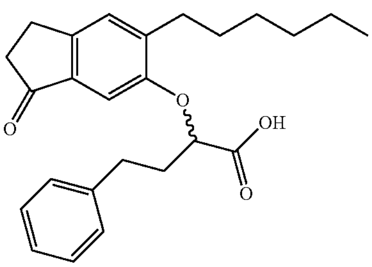 | 394.51 | ES+ 395.3 ES− 393.3 | |
| 164 | 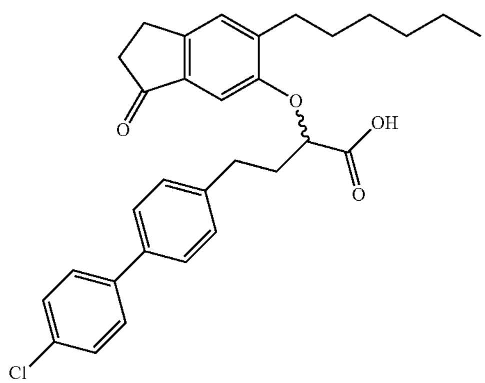 | 505.05 | ES− 503.2/505.2 | |
| 165 | 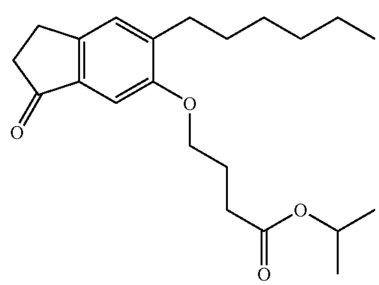 | 360.49 | ES+ 361.3 | |
| 166 | 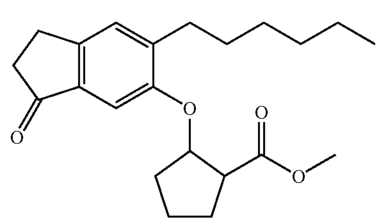 | 358.48 | ES+ 359.3 | |

-continued

| No. | structure | MW | mass | NMR |
|---|---|---|---|---|
| 167 | 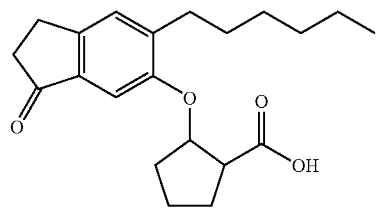 | 344.45 | ES+ 345.2 | |
| 168 | 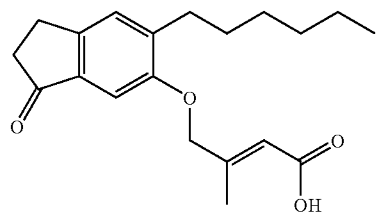 | 330.42 | ES+ 331.2 | |
| 169 | 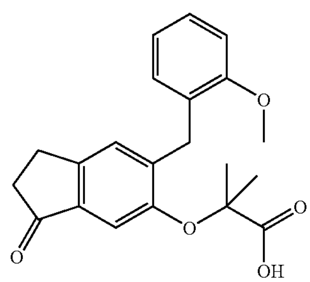 | 354.40 | ES+ 355.2<br>ES− 353.2 | |
| 170 | 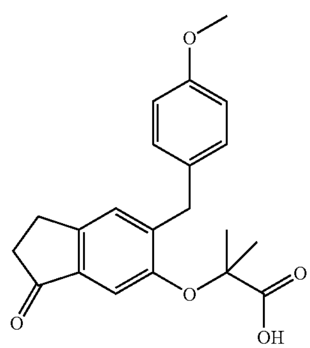 | 354.40 | ES− 353.2 | |
| 171 | 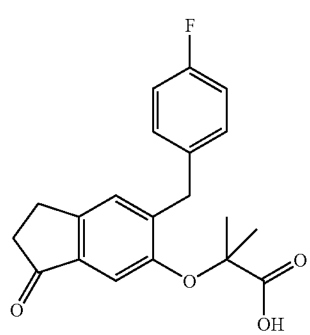 | 343.37 | ES+ 343.2<br>ES− 341.2 | |

-continued

| No. | structure | MW | mass | NMR |
|---|---|---|---|---|
| 172 | 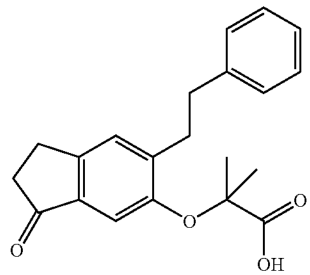 | 338.40 | ES+ 339.2<br>ES− 337.2 | |
| 173 | 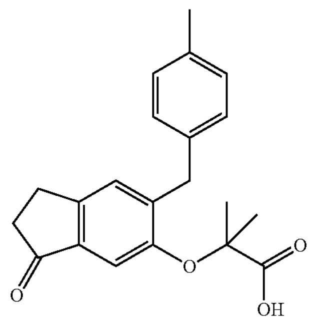 | 338.40 | ES+ 339.2<br>ES− 337.2 | |
| 174 | 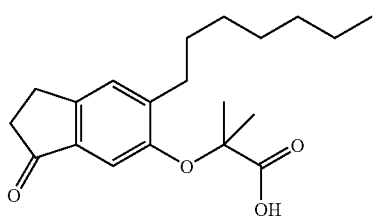 | 332.44 | ES+ 333.3<br>ES− 331.3 | |
| 175 | 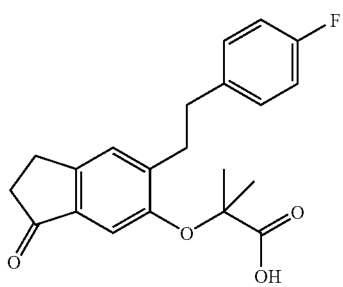 | 356.39 | ES+ 357.3<br>ES− 355.2 | |
| 176 | 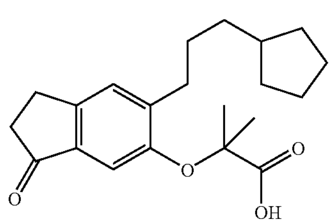 | 344.45 | ES+ 345.3<br>ES− 343.3 | |

ES− = [M − H]
ES+ = [M + H]

The invention claimed is:

1. A compound of formula I:

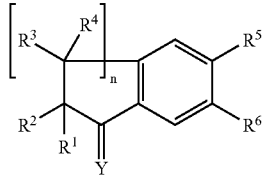

in which:

n is 1;

Y represents O; N—OR$^9$, in which R$^9$ represents H or a saturated hydrocarbon-based aliphatic group; CR$^{10}$R$^{11}$, in which R$^{10}$ and R$^{11}$, which may be identical or different, represent H or a saturated hydrocarbon-based aliphatic group;

R$^1$ and R$^2$, in which may be identical or different, represent H or a saturated aliphatic hydrocarbon-based chain; or alternatively R$^1$ and R$^2$ together form an optionally substituted saturated aliphatic hydrocarbon-based chain;

R$^3$ and R$^4$, which may be identical or different, take any of the meanings given above for R$^1$ and R$^2$, or alternatively R$^1$ and R$^4$ borne by the carbon alpha to CR$^1$R$^2$ represent nothing and a double bond links the CR$^1$R$^2$ carbon to the alpha CR$^3$R$^4$ carbon;

one of R$^5$ and R$^6$ represents W, and the other represents Z, which is a saturated or unsaturated aliphatic hydrocarbon-based radical; an optionally substituted, saturated, unsaturated and/or aromatic carbocyclic or heterocyclic radical; a radical -alk-Cy, in which alk represents an alkylene chain and Cy represents an optionally substituted saturated, unsaturated and/or aromatic heterocyclic or carbocyclic radical;

W represents —XL-CO$_2$R$^7$;

L represents a saturated or unsaturated aliphatic hydrocarbon-based chain, which is optionally substituted and/or optionally interrupted by optionally substituted arylene;

X represents O; NR$^8$, in which R$^8$ represents H; a saturated aliphatic hydrocarbon-based group; a group —CO—R' or —SO$_2$—R', in which R' takes any of the meanings given below for R$^7$ with the exception of H; or R$^8$ represents an optionally substituted aromatic carbocyclic group; or X represents S(O)$_m$, in which m is 0, 1 or 2;

R$^7$ represents H; a saturated or unsaturated aliphatic hydrocarbon-based group; an optionally substituted, saturated, unsaturated and/or aromatic carbocyclic group; an optionally substituted, saturated, unsaturated and/or aromatic heterocyclic group;

or a pharmaceutically acceptable salt, or solvate thereof.

2. A compound according to claim 1, wherein R$^1$, R$^2$, R$^3$ and R$^4$ are independently a hydrogen atom or alkyl.

3. A compound according to claim 1, wherein R$^7$ represents H or alkyl.

4. A compound according to claim 1, wherein L represents alkylene, alkenylene or -alk°-Ar°, in which alk° represents alkylene and Ar° represents optionally substituted phenylene.

5. A compound according to claim 4, wherein L represents

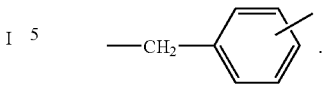

6. A compound according to claim 1, wherein Z represents alkyl optionally substituted by one or more radicals T; alkenyl optionally substituted by one or more radicals T; alkynyl optionally substituted by one or more radicals T; phenyl optionally substituted by one or more radicals T; cycloalkyl optionally substituted by one or more radicals T; monocyclic or bicyclic heteroaryl optionally substituted by one or more radicals T; -alk$^1$-Cy$^1$, in which alk$^1$ represents alkylene, and Cy$^1$ represents phenyl optionally substituted by one or more radicals T, or alternatively Cy$^1$ represents cycloalkyl, optionally substituted by one or more radicals T; T is an optionally halogenated alkyl; optionally halogenated alkoxy; a halogen atom; or cyano.

7. A compound according to claim 1, wherein R$^1$, R$^2$, R$^3$ and R$^4$ represent a hydrogen atom; Y represents O; R$^5$ represents (C$_1$-C$_{10}$)alkyl; (C$_2$-C$_{10}$) alkynyl; -alk$^1$-Cy$^1$, in which alk$^1$ represents (C$_1$-C$_3$)alkylene and Cy$^1$ represents phenyl optionally substituted by one or more radicals T, in which T is an optionally halogenated alkyl; optionally halogenated alkoxy; a halogen atom; or cyano; R$^6$ represents W, in which X represents O or NH; and L represents (C$_1$-C$_3$)alkylene.

8. A compound according to claim 6, wherein X represents NH; and R$^5$ represents (C$_1$-C$_{10}$)alkyl.

9. A compound according to claim 6, wherein X represents O; and R$^5$ represents (C$_1$-C$_{10}$)alkyl; (C$_2$-C$_{10}$)alkynyl; or -alk$^1$-Cy$^1$, in which alk$^1$ represents (C$_1$-C$_3$)alkylene and Cy$^1$ represents phenyl.

10. A compound according to claim 6, wherein Z represents alkyl, optionally substituted by cyano; phenyl, optionally substituted by trifluoromethyl, with halogen, with alkyl or with alkoxy; phenylalkyl, in which phenyl is substituted by one or more halogen atoms, alkyl or alkoxy; alkynyl; or cycloalkylalkyl.

11. A compound according to claim 1, which is one of the following compounds

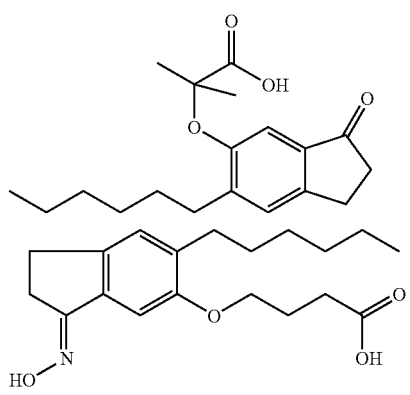

101

-continued

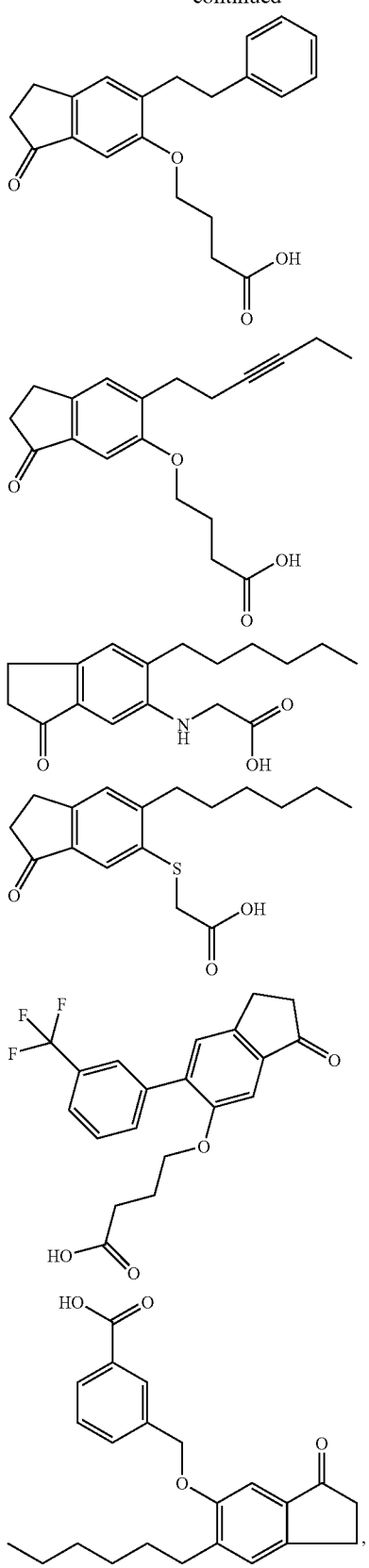

or a pharmaceutically acceptable salt, or solvate thereof.

102

12. A pharmaceutical composition comprising a compound of formula I according to claim 1 and a pharmaceutically acceptable vehicle.

13. A method of activating the PPARα and PPRγ isoforms in regulation of lipidaemia and glycaemia comprising administering an effective amount of a pharmaceutical composition according to claim 12.

14. A method for treating dyslipidaemia, atherosclerosis or diabetes comprising administering a subject in need thereof an effective amount of a pharmaceutical composition according to claim 12.

15. A process for preparing a compound of formula I according to claim 1, comprising reacting a compound of formula II:

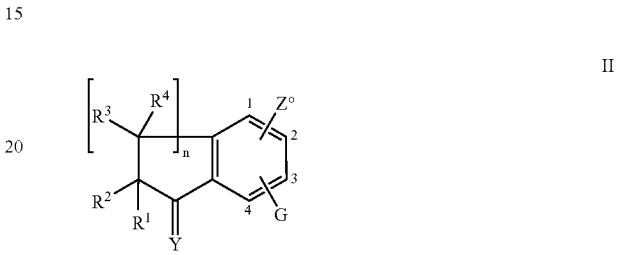

in which
$R^1$, $R^2$, $R^3$, $R^4$, n and Y are as defined for formula I, G represents —XH, in which X is S or O, NHCOCF$_3$ or NHR$^8$, R$^8$ being as defined for formula I; and Z° is a radical that is a precursor of Z, or alternatively Z° represents Z, Z being as defined for formula I, Z° and G being in positions 2 and 3 of the phenyl nucleus;
with a compound of formula III:

Gp-L-CO$_2$R$^7$     III in which R$^7$ and L are as defined for formula I and Gp represents a leaving group, in the presence of a base.

16. A process for preparing a compound of formula I according to claim 1, in which Z represents Cy, in which Cy denotes an optionally substituted aryl or heteroaryl group, comprising reacting a compound of formula IVa:

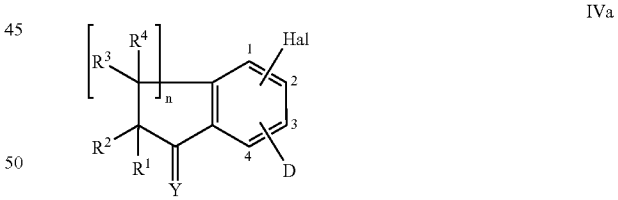

in which D represents —NHCOCF$_3$ or —X-L-CO$_2$R$^7$, and L, R$^7$, Y, X, R$^1$, R$^2$, R$^3$, R$^4$ and n are as defined for formula I, and Hal represents a halogen atom, —Hal and D being in position 2 or 3,
with an arylboronic or heteroarylboronic acid of formula V:

Cy B(OH)$_2$     (V)

in which Cy optionally bears one or more substituents,
in the presence of a palladium 0 complex and a mineral or organic base.

17. A process for preparing a compound of formula I according to claim 1, in which Z represents —CH$_2$-π, in which π represents alkyl; alkenyl; alkynyl; Cy$^1$, wherein Cy$^1$ is as defined for Cy for formula I; or -alk²-Cy¹, wherein alk² represents alkylene and Cy¹ is as defined above, comprising reacting a compound of formula IVa:

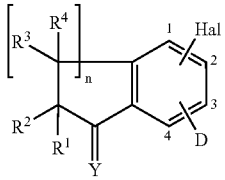

IVa in which D represents —NHCOCF₃ or —X-L-CO₂R⁷, and L, R⁷, Y, X, R¹, R², R³, R⁴ and n are as defined for formula I, and Hal represents a halogen atom, —Hal and D being in position 2 or 3,
with a compound of formula VII (π-CH₂-)ZnBr or (π-CH₂)ZnCl    VII in which π is as defined above,
in the presence of a palladium complex.

18. A process for preparing a compound of formula I according to claim 1 in which Y represents N—OH, comprising reacting a compound of formula I in which Y=O with a hydroxylamine salt in the presence of an alkali metal salt.

19. A process for preparing a compound of formula I in which Y represents $CR^{10}R^{11}$, in which $R^{10}$ and $R^{11}$ are as defined for formula I, comprising reacting a compound of formula I in which Y represents O with a compound of formula IX $(C_6H_5)P^+CR^{10}R^{11}H, Br^-$    IX in the presence of a base.

20. A compound of formula I:

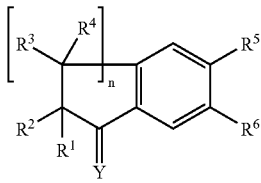

I in which:
n is 1;
Y represents O; N—OR⁹, in which R⁹ represents H or a saturated hydrocarbon-based aliphatic group; $CR^{10}R^{11}$, in which $R^{10}$ and $R^{11}$, which may be identical or different, represent H or a saturated hydrocarbon-based aliphatic group;
R¹ and R², which may be identical or different, represent H or a saturated aliphatic hydrocarbon-based chain; or alternatively R¹ and R² together form an optionally substituted saturated aliphatic hydrocarbon-based chain;
R³ and R⁴, which may be identical or different, take any of the meanings given above for R¹ and R², or alternatively R¹ and R⁴ borne by the carbon alpha to CR¹R² represent nothing and a double bond links the
CR¹R² carbon to the alpha CR³R⁴ carbon; or alternatively one of R⁵ and R⁶ represents W, and the other represents Z, which is a saturated or unsaturated aliphatic hydrocarbon-based radical; an optionally substituted, saturated, unsaturated and/or aromatic carbocyclic or heterocyclic radical; a radical -alk-Cy, in which alk represents an alkylene chain and Cy represents an optionally substituted saturated, unsaturated and/or aromatic heterocyclic or carbocyclic radical;
W represents —XL-CO₂R⁷;
L represents a saturated or unsaturated aliphatic hydrocarbon-based chain, which is optionally substituted and/or optionally interrupted by optionally substituted arylene;
X represents O; NR⁸, in which R⁸ represents H; a saturated aliphatic hydrocarbon-based group; a group —CO-R' or —SO₂—R', in which R' takes any of the meanings given below for R⁷ with the exception of H; or R⁸ represents an optionally substituted aromatic carbocyclic group; or X represents $S(O)_m$, in which m is 0, 1 or 2;
R⁷ represents H; a saturated or unsaturated aliphatic hydrocarbon-based group; an optionally substituted, saturated, unsaturated and/or aromatic carbocyclic group; an optionally substituted, saturated, unsaturated and/or aromatic heterocyclic group;

or a pharmaceutically acceptable salt thereof.

21. A compound according to claim 20, which is one of the following compounds

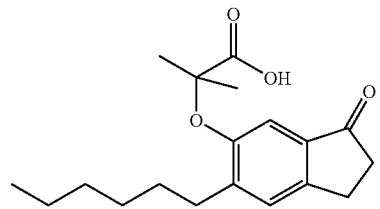

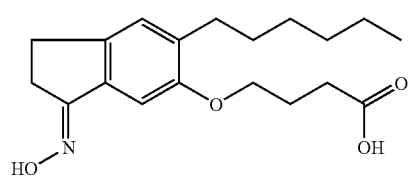

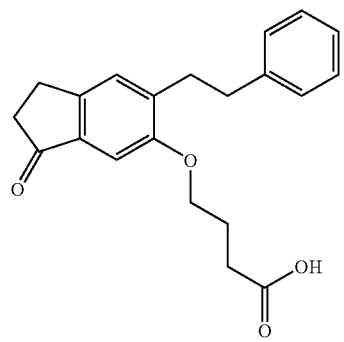

-continued

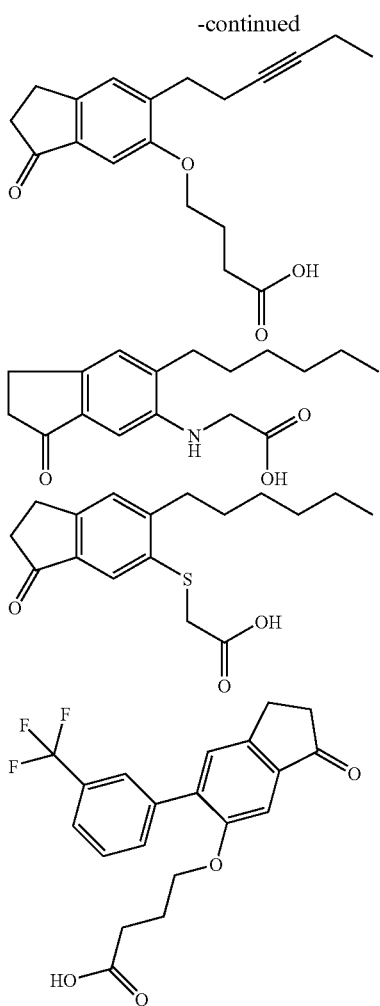

-continued

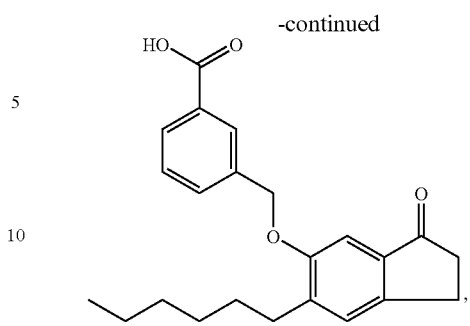

or a pharmaceutically acceptabLe salt thereof.

22. A composition comprising stereoisomers of a compound according to claim 20.

23. A composition comprising a mixture of isomers of a compound according to claim 20.

24. A composition comprising stereoisomers of a compound according to claim 21.

25. A composition comprising a mixture of isomers of a compound according to claim 21.

26. A pharmaceutical composition comprising a compound of formula I according to claim 20 and a pharmaceutically acceptable vehicle.

27. A method of activating the PPARα and PPRγ isoforms in regulation of lipidaemia and glycaemia comprising administering an effective amount of a pharmaceutical composition according to claim 26.

28. A method for treating dyslipidaemia, atherosclerosis or diabetes comprising administering a subject in need thereof an effective amount of a pharmaceutical composition according to claim 26.

29. A pharmaceutical composition comprising a compound of formula I according to claim 21 and a pharmaceutically acceptable vehicle.

* * * * *